US010925957B2

United States Patent
Ross et al.

(10) Patent No.: US 10,925,957 B2
(45) Date of Patent: *Feb. 23, 2021

(54) SYNERGISTIC CO-ADMINISTRATION OF COMPUTATIONALLY OPTIMIZED BROADLY REACTIVE ANTIGENS FOR H1N1 INFLUENZA

(71) Applicants: Oregon Health & Science University, Portland, OR (US); Sanofi Pasteur, Inc., Swiftwater, PA (US)

(72) Inventors: Ted Milburn Ross, Watkinsville, GA (US); Tim Alefantis, Springbrook Township, PA (US); Donald Martin Carter, Jr., Athens, GA (US); Christopher Austin Darby, Port Saint Lucie, FL (US); Harold Kleanthous, Chelmsford, MA (US)

(73) Assignees: OREGON HEALTH & SCIENCE UNIVERSITY, Portland, OR (US); SANOFI PASTEUR, INC., Swiftwater, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/258,094

(22) Filed: Jan. 25, 2019

(65) Prior Publication Data

US 2019/0175721 A1 Jun. 13, 2019

Related U.S. Application Data

(63) Continuation of application No. 15/537,081, filed as application No. PCT/US2015/066882 on Dec. 18, 2015, now Pat. No. 10,220,086.

(60) Provisional application No. 62/094,772, filed on Dec. 19, 2014.

(51) Int. Cl.
```
A61K 39/145      (2006.01)
A61K 39/12       (2006.01)
A61K 39/00       (2006.01)
```

(52) U.S. Cl.
CPC ........... *A61K 39/145* (2013.01); *A61K 39/12* (2013.01); *A61K 2039/55505* (2013.01); *A61K 2039/55566* (2013.01); *A61K 2039/70* (2013.01); *C12N 2760/16123* (2013.01); *C12N 2760/16134* (2013.01)

(58) Field of Classification Search
CPC .............. A61K 39/145; A61K 39/12; A61K 2039/55505; A61K 2039/55566; A61K 2039/70; C12N 2760/16123; C12N 2760/16134; A61P 43/00; A61P 37/04; A61P 31/16
See application file for complete search history.

(56) References Cited

U.S. PATENT DOCUMENTS

| | | | |
|---|---|---|---|
| 9,212,207 B2 * | 12/2015 | Ross | A61K 39/145 |
| 9,309,290 B2 * | 4/2016 | Ross | C07K 14/005 |
| 9,555,095 B2 * | 1/2017 | Ross | A61K 39/145 |
| 9,566,328 B2 * | 2/2017 | Ross | C07K 14/005 |
| 10,017,544 B2 * | 7/2018 | Ross | C07K 14/005 |
| 10,220,086 B2 * | 3/2019 | Ross | A61K 39/12 |
| 2010/0221284 A1 | 9/2010 | Eichhorn et al. | |
| 2014/0147459 A1 * | 5/2014 | Ross | C07K 14/005 |
| | | | 424/186.1 |
| 2014/0227309 A1 | 8/2014 | Smith et al. | |
| 2016/0279226 A1 * | 9/2016 | Ross | A61K 39/145 |
| 2017/0114102 A1 | 4/2017 | Ross et al. | |

FOREIGN PATENT DOCUMENTS

| | | |
|---|---|---|
| WO | 2010125461 A1 | 11/2010 |
| WO | 2013/148164 A1 | 10/2013 |
| WO | 2016/201127 A1 | 12/2016 |
| WO | 2017/053413 A1 | 3/2017 |

OTHER PUBLICATIONS

International Search Report and Written Opinion dated May 20, 2016 from International Application No. PCT/US2015/066882 (Authorized Officer, Shane Thomas), pp. 1-14.
Extended European Search Report dated Apr. 30, 2018 from European Patent Application No. 15871236.4, 12 pages.
Giles et al., "Antibody Breadth and Protective Efficacy Are Increased by Vaccination with Computationally Optimized Hemagglutinin but Not with Polyvalent Hemagglutinin-Based H5N1 Virus-Like Particle Vaccines", Clinical and Vaccine Immunology, Feb. 2012, vol. 19, No. 2, pp. 128-139.
Crevar et al., "Cocktail of H5N1 COBRA HA vaccines elicit protective antibodies against H5N1 viruses from multiple clades", Human Vaccines & Immunotherapeutics. Mar. 2015, vol. 11, No. 3. pp. 572-583.
Wang et al., "DNA Prime and Virus-like Particle Boost From a Single H5N1 Strain Elicits Broadly Neutralizing Antibody Responses Against Head Region of H5 Hemagglutinin", The Jourial of Infectious Diseases. Mar. 1, 2014, vol. 209. No. 5. Pages 676-685.
Office Action dated Apr. 7, 2020 for Japanese Application No. 2017-533485, 8 pages with English translation.
Bandell et al. "Protective efficacy of live-attenuated influenza vaccine (multivalent, Ann Arbor strain): a literature review addressing interference", Expert Review of Vaccines, 2011, vol. 10, No. 8, pp. 1131-1141.

(Continued)

*Primary Examiner* — Rachel B Gill
(74) *Attorney, Agent, or Firm* — MH2 Technology Law Group, LLP

(57) ABSTRACT

Co-administration (for example, immunogenic cocktail compositions and/or prime boost regimens) of computationally optimized H1N1 influenza hemagglutinin (HA) polypeptides is provided. Coadministration of the optimized H1N1 influenza hemagglutinin (HA) polypeptides facilitates synergistic neutralization of viral infection and provides for improved protective immunity (for example, a broad reactive immune response) to diverse and multiple H1N1 influenza virus strains, including both seasonal and pandemic strains.

28 Claims, 14 Drawing Sheets

Specification includes a Sequence Listing.

(56) References Cited

OTHER PUBLICATIONS

Vemula et al., "Broadly Protective Adenovirus-Based Multivalent Vaccines against Highly Pathogenic Avian Influenza Viruses for Pandemic Preparedness", PLOS ONE, 2013, vol. 8, No. 4, e62496, pp. 1-12.

Quan et al., "A bivalent influenza VLP vaccine confers complete inhibition of virus replication in lungs", Vaccine, 2008, vol. 26, pp. 3352-3361.

Communication pursuant to Article 94(3) dated Oct. 5, 2020 for European Application No. 15871236.4, 6 pages.

Giles et al., "A Computationally Optimized Hemagglutinin Virus-Like Particle Vaccine Elicits Broadly Reactive Antibodies that Protect Nonhuman Primates from H5N1 Infection", 2012, The Journal of Infectious Diseases, vol. 205, No. 10, pp. 1562-1570.

\* cited by examiner

H1N1 COBRA Prime/Boost

FIG. 1A

H1N1 COBRA Prime/Boost

FIG. 1B

H1N1 COBRA Prime/Boost

H1N1 COBRA Prime/Boost

Cocktail H1N1 COBRA

FIG. 2A

Cocktail H1N1 COBRA

FIG. 2B

Cocktail H1N1 COBRA

☒ X1/X6/P1
▨ Mock

HAI Titer Log 2 vs Virus: PR/34, Weiss/43, FM/47, Den/57, NJ/76, USSR/77, Braz/78, Chile/83, Sing/86, TX/91, Bei/95, NC/99, SI/06, Bris/07, CA/09

FIG. 2C

Week 8

▨ X3/P1 +X6/P1

HAI Titer Log 2 vs Virus: PR/34, Weiss/43, FM/47, Den/57, NJ/76, Braz/78, Chile/83, Sing/86, TX/91, Bei/95, NC/99, SI/06, Bris/07, CA/09

FIG. 2D

SEQUENCE LISTING

```
<160> NUMBER OF SEQ ID NOS: 4

<210> SEQ ID NO 1
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Lys Ala Arg Leu Leu Val Leu Leu Cys Ala Leu Ala Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Glu Ser Leu Leu Ser Ala Arg Ser Trp Ser Tyr Ile
                85                  90                  95

Val Glu Thr Pro Asn Ser Glu Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Thr Lys Gly Val Thr Ala Ala Cys Ser His Ala Gly Lys Ser Ser
145                 150                 155                 160

Phe Tyr Arg Asn Leu Leu Trp Leu Thr Lys Lys Gly Gly Ser Tyr Pro
                165                 170                 175

Lys Leu Ser Lys Ser Tyr Val Asn Asn Lys Gly Lys Glu Val Leu Val
            180                 185                 190

Leu Trp Gly Val His His Pro Ser Thr Ser Thr Asp Gln Gln Ser Leu
        195                 200                 205

Tyr Gln Asn Glu Asn Ala Tyr Val Ser Val Ser Ser Asn Tyr Asn
    210                 215                 220

Arg Arg Phe Thr Pro Glu Ile Ala Glu Arg Pro Lys Val Arg Gly Gln
225                 230                 235                 240

Ala Gly Arg Met Asn Tyr Tyr Trp Thr Leu Leu Glu Pro Gly Asp Thr
                245                 250                 255

Ile Ile Phe Glu Ala Thr Gly Asn Leu Ile Ala Pro Trp Tyr Ala Phe
            260                 265                 270

Ala Leu Ser Arg Gly Ser Gly Ser Gly Ile Ile Thr Ser Asn Ala Ser
        275                 280                 285

Met His Glu Cys Asn Thr Lys Cys Gln Thr Pro Gln Gly Ala Ile Asn
```

290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Asn
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Arg Asn Asn Ala Lys Glu Ile Gly Asn Gly
465                 470                 475                 480

Cys Phe Glu Phe Tyr His Lys Cys Asp Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
            565

<210> SEQ ID NO 2
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Glu Ala Arg Leu Leu Val Leu Leu Cys Ala Phe Ala Ala Thr Asn
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

-continued

```
Asn Pro Glu Cys Glu Leu Leu Ile Ser Lys Glu Ser Trp Ser Tyr Ile
                 85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Thr Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
```

```
                500                 505                 510
Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
        530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 3
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Glu Ala Arg Leu Leu Val Leu Leu Cys Ala Phe Ala Ala Thr Asn
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Ser Leu Phe Ser Lys Glu Ser Trp Ser Tyr Ile
                85                  90                  95

Ala Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Lys Gly Val Thr Ala Ser Cys Ser His Asn Gly Lys Ser Ser
145                 150                 155                 160

Phe Tyr Arg Asn Leu Leu Trp Leu Thr Glu Lys Asn Gly Leu Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Gly Asp Gln Arg Ala Ile
        195                 200                 205

Tyr His Thr Glu Asn Ala Tyr Val Ser Val Val Ser Ser His Tyr Ser
    210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285
```

Met Asp Glu Cys Asp Ala Lys Cys Gln Thr Pro Gln Gly Ala Ile Asn
290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Arg Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 4
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Glu Ala Arg Leu Leu Val Leu Leu Cys Ala Phe Ala Ala Thr Asn
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Ile
50                  55                  60

Ala Pro Leu Gln Leu Gly Lys Cys Asn Ile Ala Gly Trp Ile Leu Gly
65                  70                  75                  80

```
Asn Pro Glu Cys Glu Ser Leu Leu Ser Lys Arg Ser Trp Ser Tyr Ile
             85                  90                  95

Val Glu Thr Pro Asn Ser Glu Asn Gly Thr Cys Tyr Pro Gly Asp Phe
        100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Asn
        130                 135                 140

Thr Thr Lys Gly Val Thr Ala Ala Cys Ser His Ala Gly Lys Ser Ser
145                 150                 155                 160

Phe Tyr Arg Asn Leu Leu Trp Leu Thr Lys Lys Asn Gly Ser Tyr Pro
            165                 170                 175

Asn Leu Ser Lys Ser Tyr Val Asn Asn Lys Gly Lys Glu Val Leu Val
            180                 185                 190

Leu Trp Gly Val His His Pro Ser Asn Ile Glu Asp Gln Gln Ser Leu
        195                 200                 205

Tyr Gln Asn Glu Asn Ala Tyr Val Ser Val Val Ser Ser Asn Tyr Asn
210                 215                 220

Arg Arg Phe Thr Pro Glu Ile Ala Lys Arg Pro Lys Val Arg Asp Gln
225                 230                 235                 240

Glu Gly Arg Met Asn Tyr Tyr Trp Thr Leu Leu Glu Pro Gly Asp Thr
            245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
            275                 280                 285

Met His Glu Cys Asp Thr Lys Cys Gln Thr Pro Gln Gly Ala Ile Asn
        290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Val Thr Gly Leu Arg
            325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
            355                 360                 365

His His Gln Asn Glu Gln Gly Ser Gly Tyr Ala Ala Asp Gln Lys Ser
        370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Asn
            405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
            435                 440                 445

Glu Arg Thr Leu Asp Phe His Asp Ser Asn Val Lys Asn Leu Tyr Glu
450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
            485                 490                 495
```

```
Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
        530                 535             540

Val Ser Leu Gly Ala Ile Ser Phe Trp Met Cys Ser Asn Gly Ser Leu
545                 550                 555                 560

Gln Cys Arg Ile Cys Ile
                565
```

SYNERGISTIC CO-ADMINISTRATION OF COMPUTATIONALLY OPTIMIZED BROADLY REACTIVE ANTIGENS FOR H1N1 INFLUENZA

CROSS-REFERENCE TO RELATED APPLICATIONS

This application is a continuation of U.S. application Ser. No. 15/537,081, filed 16 Jun. 2017, which is a U.S. National Stage Application of PCT/US2015/066882, filed 18 Dec. 2015, which claims the benefit of, and relies on the filing date of, U.S. provisional patent application No. 62/094,772, filed 19 Dec. 2014, the entire disclosure of which is incorporated herein by reference.

SEQUENCE LISTING

The instant application contains a Sequence Listing which has been submitted electronically in ASCII format and is hereby incorporated by reference in its entirety. Said ASCII copy, created on Dec. 16, 2015, is named 0171.0005-PCT_SL.txt and is 20,224 bytes in size.

BACKGROUND

Influenza is caused by a virus that attacks mainly the upper respiratory tract—the nose, throat and bronchi and rarely also the lungs. The infection usually lasts for about a week. It is characterized by sudden onset of high fever, myalgia, headache and severe malaise, non-productive cough, sore throat, and rhinitis. Most people recover within one to two weeks without requiring any medical treatment. However, in the very young, the elderly and people suffering from medical conditions such as lung diseases, diabetes, cancer, kidney or heart problems, influenza poses a serious risk. In these people, the infection may lead to severe complications of underlying diseases, pneumonia and death. Annual influenza epidemics are thought to result in between three and five million cases of severe illness and between 250,000 and 500,000 deaths every year around the world.

Influenza virus is a member of Orthomyxoviridae family. There are three subtypes of influenza viruses, designated influenza A, influenza B, and influenza C. The influenza virion contains a segmented negative-sense RNA genome, which encodes the following proteins: hemagglutinin (HA), neuraminidase (NA), matrix (MI), proton ion-channel protein (M2), nucleoprotein (NP), polymerase basic protein 1 (PBI), polymerase basic protein 2 (PB2), polymerase acidic protein (PA), and nonstructural protein 2 (NS2). The HA, NA, MI, and M2 are membrane associated, whereas NP, PBI, PB2, PA, and NS2 are nucleocapsid associated proteins. The MI protein is the most abundant protein in influenza particles. The HA and NA proteins are envelope glycoproteins, responsible for virus attachment and penetration of the viral particles into the cell. Specifically, HA binds the influenza virus to cells with sialic acid-containing on surface structures on their membranes.

Both HA and NA proteins are the sources of the major immunodominant epitopes for virus neutralization and protective immunity, making them important components for prophylactic influenza vaccines. The genetic makeup of influenza viruses allows frequent minor genetic changes, known as antigenic drift. Thus, the amino acid sequence of the major antigens of influenza, particularly HA, is highly variable across groups, subtypes and strains. For this reason, current seasonal influenza vaccines need to be revised every 1-3 years to account for mutations in HA and NA proteins (antigenic drift). A further limitation of the current vaccine approach is that the influenza strains used in the vaccine are selected by the WHO/CDC based on the agencies' best guess as to the prevalent influenza strains for the upcoming flu season. Often times, the guess is not accurate and the vaccine strains do not match the seasonal influenza strains, limiting the effectiveness of the seasonal vaccines. Seasonal vaccines are also not designed to provide protection against pandemic strains that can result from antigen shift. Further, as the name suggests, seasonal vaccines must be administered every year.

Pandemic outbreaks of influenza are caused by the emergence of a pathogenic and transmissible virus to which the human population is immunologically naïve. Because the virus is new, the human population has little to no immunity against it. The virus spreads quickly from person-to-person worldwide. Three times in the last century, the influenza A viruses have undergone major genetic changes mainly in their H-component, resulting in global pandemics and large tolls in terms of both disease and deaths. The most infamous pandemic was "Spanish Flu" which affected large parts of the world population and is thought to have killed at least 40 million people in 1918-1919. More recently, two other influenza A pandemics occurred in 1957 ("Asian influenza") and 1968 ("Hong Kong influenza") and caused significant morbidity and mortality globally. In contrast to current influenza epidemics, these pandemics were associated with severe outcomes also among healthy younger persons, albeit not on such a dramatic scale as the "Spanish flu" where the death rate was highest among healthy young adults. More recently, limited outbreaks of a new influenza subtype A (H1N1) directly transmitted from swine to humans have occurred in Mexico in 2009 and are being detected in an increasing number of countries. Currently, the mortality rate associated with swine-origin H1N1 influenza viruses appears to be similar to that of seasonal influenza strains. However, increased surveillance and detection of swine-origin H1N1 influenza could push the mortality rates higher. Due to antigenic drift, and even more dramatic alterations known as antigenic shift, pandemic influenza antigens (e.g., the HA amino acid sequence of the pandemic strain) are highly unpredictable. Thus, vaccines have traditionally been unavailable until the later stages of a pandemic.

There is an unmet need for influenza vaccines that can better address the current problems of antigenic drift, antigenic shift, and virus mismatch by providing broader protection against multiple influenza strains, including both seasonal and pandemic strains. There is also an unmet need for influenza vaccines that provide longer lasting immunity, particularly vaccines that would not have to be administered every year.

SUMMARY

The present invention provides, among other things, co-administration (i.e., prime-boost combinations or composition cocktails) of computationally optimized H1N1 influenza hemagglutinin (HA) polypeptides that, when presented to the immune system can elicit broadly neutralizing antibodies against both seasonal and pandemic H1N1 influenza strains. Without being bound by any particular theory, it is thought that each individual polypeptide elicits different sets of antibodies that bind to different antigenic regions of the HA molecule; but when co-administered (either as a cocktail or as part of a prime-boost regimen), they elicit antibodies that recognize divergent HA head epitopes that synergistically neutralize viral infection and provide for improved protective immunity (e.g., a broad reactive immune response against both seasonal and pandemic strains) to multiple H1N1 influenza virus strains and/or longer lasting immunity. The optimized HA polypeptides were developed through a series of HA protein alignments, and subsequent generation of consensus sequences based on thousands of human and swine H1N1 influenza isolates. In particular embodiments, the protective immunity spans H1N1 strains originating over at least the last 5, 6, 7, 8, 9, 11, 12, 15, 20, etc. years.

Provided herein is an immunogenic composition comprising a combination of at least two recombinant H1N1 influenza hemagglutinin (HA) polypeptides, wherein the combination comprises a first recombinant, optimized H1N1 influenza HA polypeptide comprising an amino acid sequence at least 98%, 98.5%, 99% or 99.5% identical to SEQ ID NO: 1 (P1) and a second recombinant, optimized H1N1 influenza HA polypeptide comprising an amino acid sequence selected from the group consisting of: 1) an amino acid sequence at least 99% or 99.5% identical to SEQ ID NO: 2 (X6), 2) an amino acid sequence at least 99% or 99.5% identical to SEQ ID NO: 3 (X3), and 3) an amino acid sequence at least 96%, 96.5%, 97%, 97.5%, 98%, 98.5%, 99%, or 99.5% identical to SEQ ID NO: 4 (X1).

Also provided herein is an immunogenic composition of at least two recombinant H1N1 influenza hemagglutinin (HA) polypeptides, wherein the combination comprises a first recombinant, optimized H1N1 influenza HA polypeptide comprising an amino acid sequence at least 98%, 98.5%, 99% or 99.5% identical to residues 2-566 of SEQ ID NO: 1 and a second recombinant, optimized H1N1 influenza HA polypeptide comprising an amino acid sequence selected from the group consisting of: 1) an amino acid sequence at least 99% or 99.5% identical to residues 2-565 of SEQ ID NO: 2, 2) an amino acid sequence at least 99% or 99.5% identical to residues 2-566 of SEQ ID NO: 3, and 3) an amino acid sequence at least 96%, 96.5%, 97%, 97.5%, 98%, 98.5%, 99%, or 99.5% identical to residues 2-566 of SEQ ID NO: 4.

In some embodiments, the compositions described herein comprise (i) a first recombinant, optimized H1N1 influenza HA polypeptide comprising an amino acid sequence at least 98%, 98.5%, 99%, or 99.5% identical to SEQ ID NO: 1, and (ii) a second recombinant, optimized H1N1 influenza HA polypeptide comprising an amino acid sequence at least 99 or 99.5% identical to SEQ ID NO: 2. In some embodiments, the compositions comprise at least two different recombinant, optimized H1N1 influenza HA polypeptides, wherein the amino acid sequence of the polypeptides comprises no more than two, or no more than one substitution relative to SEQ ID NO: 1 or SEQ ID NO: 2. In some embodiments, the first and/or second recombinant, optimized H1N1 influenza HA polypeptides lack the N-terminal methionine residue. In some embodiments, the compositions described herein comprise (i) a first recombinant, optimized H1N1 influenza HA polypeptide comprising an amino acid sequence of SEQ ID NO: 1 or residues 2-566 of SEQ ID NO: 1, and (ii) a second recombinant, optimized H1N1 influenza HA polypeptide comprising an amino acid sequence of SEQ ID NO: 2 or residues 2-565 of SEQ ID NO: 2.

In some embodiments, the compositions described herein comprise (i) a first recombinant, optimized H1N1 influenza HA polypeptide comprising an amino acid sequence at least 98%, 98.5%, 99%, or 99.5% identical to SEQ ID NO: 1, and (ii) a second recombinant, optimized H1N1 influenza HA polypeptide comprising an amino acid sequence at least 99% or 99.5% identical to SEQ ID NO: 3. In some embodiments, the compositions comprise at least two different recombinant, optimized H1N1 influenza HA polypeptides, wherein the amino acid sequence of the polypeptides comprises no more than two, or no more than one substitution relative to SEQ ID NO: 1 or SEQ ID NO: 3. In some embodiments, the recombinant H1N1 influenza HA polypeptides lack the N-terminal methionine residue. In some embodiments, the compositions described herein comprise (i) a first recombinant, optimized H1N1 influenza HA polypeptide comprising an amino acid sequence of SEQ ID NO: 1 or residues 2-566 of SEQ ID NO: 1, and (ii) a second recombinant, optimized H1N1 influenza HA polypeptide comprising an amino acid sequence of SEQ ID NO: 3 or residues 2-566 of SEQ ID NO: 3.

In some embodiments, the compositions described herein comprise (i) a first recombinant, optimized H1N1 influenza HA polypeptide comprising an amino acid sequence at least 98%, 98.5%, 99%, or 99.5% identical to SEQ ID NO: 1, and (ii) a second recombinant, optimized H1N1 influenza HA polypeptide comprising an amino acid sequence at least 96%, 96.5%, 97%, 97.5%, 98%, 98.5%, 99%, or 99.5% identical to SEQ ID NO: 4. In some embodiments, the compositions comprise at least two different recombinant, optimized H1N1 influenza HA polypeptides, wherein the amino acid sequence of the polypeptides comprises no more than two, or no more than one substitution relative to SEQ ID NO: 1 or SEQ ID NO: 4. In some embodiments, the recombinant, optimized H1N1 influenza HA polypeptides lack the N-terminal methionine residue. In some embodiments, the compositions described herein comprise (i) a first recombinant, optimized H1N1 influenza HA polypeptide comprising an amino acid sequence of SEQ ID NO: 1 or residues 2-566 of SEQ ID NO: 1, and (ii) a second recombinant, optimized H1N1 influenza HA polypeptide comprising an amino acid sequence of SEQ ID NO: 4 or residues 2-566 of SEQ ID NO: 4.

In some embodiments, the compositions comprise a combination of recombinant H1N1 influenza HA polypeptides consisting of a first recombinant, optimized H1N1 influenza HA polypeptide comprising an amino acid sequence at least 98%, 98.5%, 99%, or 99.5% identical to residues 2-566 of SEQ ID NO: 1 and a second recombinant, optimized influenza HA polypeptide comprising an amino acid sequence at least 99% or at least 99.5% identical to residues 2-565 of SEQ ID NO: 2. In some embodiments, the compositions comprise a combination of recombinant H1N1 influenza HA polypeptides consisting of a first recombinant, optimized influenza HA polypeptide comprising an amino acid sequence at least 98%, 98.5%, 99%, or 99.5% identical to residues 2-566 of SEQ ID NO: 1 and a second recombinant, optimized influenza HA polypeptide comprising an amino acid sequence at least 99% or at least 99.5% identical to amino acids 2-566 of SEQ ID NO: 3. In some embodiments, the compositions comprise a combination of recombinant H1N1 influenza HA polypeptides consisting of a first recombinant, optimized influenza HA polypeptide comprising an amino acid sequence at least 98%, 98.5%, 99%, or 99.5% identical to residues 2-566 of SEQ ID NO: 1 and a second recombinant, optimized influenza HA polypeptide comprising an amino acid sequence at least 96%, 96.5%, 97%, 97.5%, 98%, 98.5%, 99%, or 99.5% identical to amino acids 2-566 of SEQ ID NO: 4. In some embodiments, the compositions described herein consist of (i) a first recombinant, optimized H1N1 influenza HA polypeptide comprising an amino acid sequence of SEQ ID NO: 1 or residues 2-566 of SEQ ID NO: 1, and (ii) a second recombinant, optimized H1N1 influenza HA polypeptide comprising an amino acid sequence of SEQ ID NO: 2 or residues 2-565 of SEQ ID NO: 2. In some embodiments, the compositions described herein comprise (i) a first recombinant, optimized H1N1 influenza HA polypeptide comprising an amino acid sequence of SEQ ID NO: 1 or residues 2-566 of SEQ ID NO: 1, and (ii) a second recombinant, optimized H1N1 influenza HA polypeptide comprising an amino acid sequence of SEQ ID NO: 3 or residues 2-566 of SEQ ID NO: 3. In some embodiments, the compositions described herein comprise (i) a first recombinant, optimized H1N1 influenza HA polypeptide comprising an amino acid sequence of SEQ ID NO: 1 or residues 2-566 of SEQ ID NO: 1, and (ii) a second recombinant, optimized H1N1 influenza HA polypeptide comprising an amino acid sequence of SEQ ID NO: 4 or residues 2-566 of SEQ ID NO: 4.

Isolated nucleic acid molecules and vectors encoding the recombinant H1N1 influenza HA polypeptides are also provided by the present disclosure. Further provided are isolated cells comprising such vectors. Also provided are recombinant influenza viruses comprising the computationally optimized recombinant HA polypeptides described herein.

Also provided are influenza virus-like particles (VLPs), inactivated influenza viruses or virions, and fusion proteins comprising the optimized HA polypeptides disclosed herein, which VLPs and viruses/virions and fusion proteins of the individual HA polypeptides can be mixed or combined into the cocktail described above.

Further provided are compositions that include the cocktails of the optimized influenza HA polypeptides, fusion proteins, viruses/virions or VLPs disclosed herein in a pharmaceutically acceptable carrier. Methods of eliciting an immune response against influenza virus in a subject by administering the disclosed immunogenic compositions of cocktails of HA polypeptides, fusion proteins, virus or VLPs are also provided by the present disclosure.

Also provided are methods of co-administering to a subject the optimized H1N1 influenza HA polypeptides disclosed herein. In certain embodiments, the methods comprise immunizing a subject against H1N1 influenza virus by administering to the subject a composition or compositions comprising the combinations or cocktails of the optimized H1N1 influenza HA polypeptides disclosed herein. Further provided are methods of immunizing a subject against H1N1 influenza virus by administering to the subject a priming vaccine comprising a first optimized H1N1 influenza HA polypeptide as described herein followed by a boosting vaccine comprising a second optimized H1N1 influenza HA polypeptide as described herein, where the second optimized H1N1 influenza HA polypeptide is different than the first optimized H1N1 influenza HA polypeptide. In some embodiments, the priming vaccine is a live, attenuated influenza virus (e.g., temperature sensitive virus). In certain embodiments, the priming vaccine comprises a recombinant, optimized H1N1 influenza HA polypeptide at least 98% identical to SEQ ID NO: 1 (i.e., P1), and the boosting vaccine comprises a recombinant, optimized H1N1 influenza HA polypeptide at least 99% identical to SEQ ID NO: 2, at least 99% identical to SEQ ID NO: 3 or at least 96% identical to SEQ ID NO: 4. (e.g., X6, X3, or X1). In other embodiments, the priming vaccine may comprise a recombinant, optimized H1N1 influenza HA polypeptide at least 99% identical to SEQ ID NO: 2, and the boosting vaccine comprises a recombinant, optimized H1N1 influenza HA polypeptide at least 98% identical to SEQ ID NO: 1, at least 99% identical to SEQ ID NO: 3 or at least 96% identical to SEQ ID NO: 4. In other embodiments, the priming vaccine may comprise a recombinant, optimized H1N1 influenza HA polypeptide at least 99% identical to SEQ ID NO: 3, and the boosting vaccine comprises a recombinant, optimized H1N1 influenza HA polypeptide at least 98% identical to SEQ ID NO: 1, at least 99% identical to SEQ ID NO: 2 or at least 96% identical to SEQ ID NO: 4.

The foregoing and other objects, features, and advantages of the invention will become more apparent from the following detailed description, which proceeds with reference to the accompanying figures.

BRIEF DESCRIPTION OF THE DRAWING

The Drawing included herein, which is comprised of the following Figures, is for illustration purposes only not for limitation.

Figures 1A, 1B:
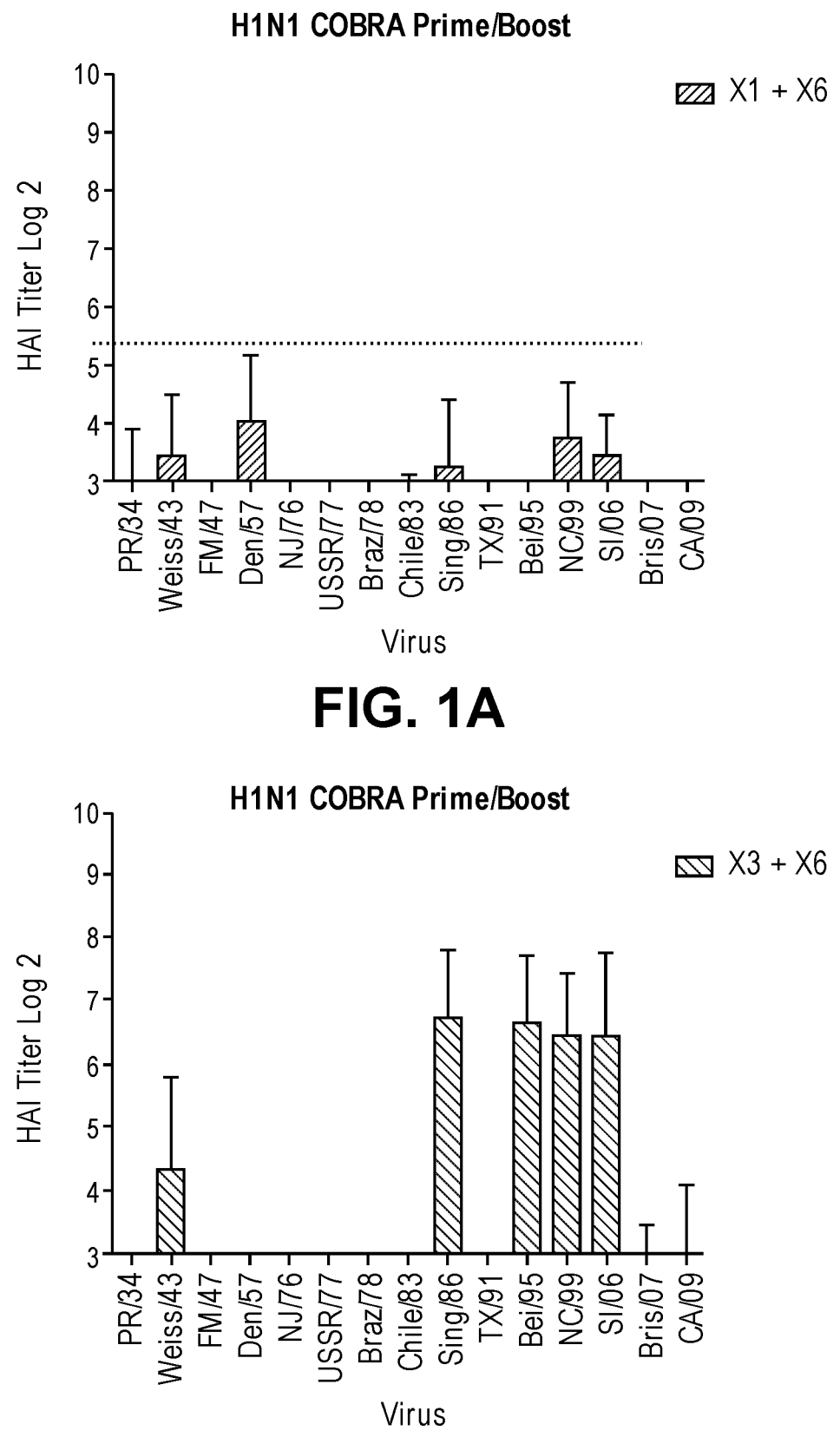
Figures 1E, 1F:
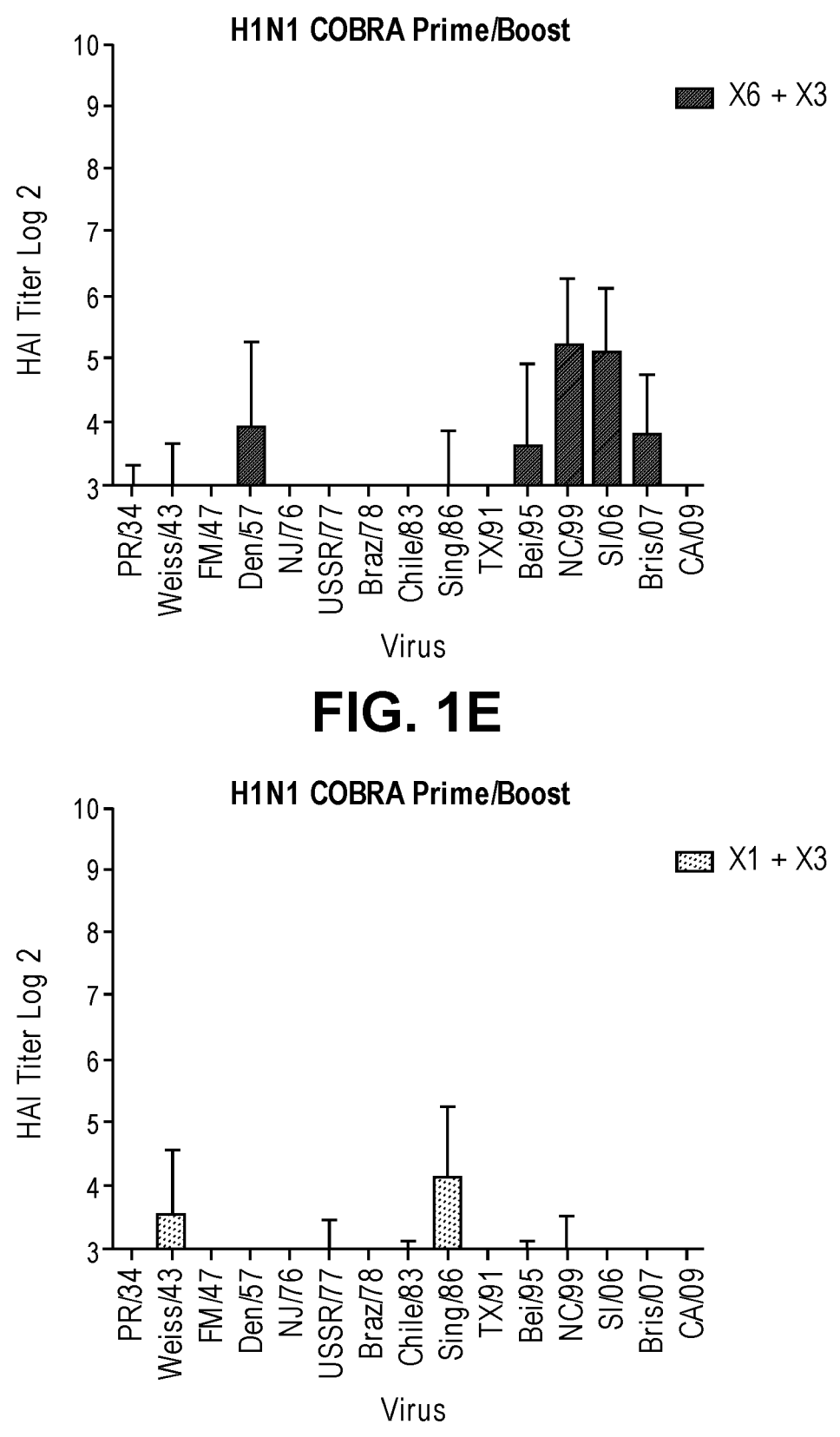

FIGS. 1A-L show hemagglutination-inhibition (HAI) serum antibody titers induced by vaccination of mice with prime-boost regimens using COBRA VLP vaccines. HAI titers were determined against a panel of 17 H1N1 influenza viruses for each group of mice vaccinated with the following prime-boost regimens of the indicated COBRA VLP vaccines. Bars represent the geometric mean titer (±S.E.M.) from antisera collected at day 56. The dotted, horizontal line represents the log 2 value that corresponds to an HAI antibody titer of 1:40.

FIGS. 2A-D show the hemagglutination-inhibition (HAI) serum antibody titers induced by vaccination of mice with cocktails of COBRA VLP vaccines. HAI titers against a panel of 17 H1N1 influenza viruses were determined for each group of mice vaccinated one of the following cocktails of COBRA VLP vaccines: X1/X3, X1/X6, or X3/X6 (A); P1/X6, P1/X3, or P1/X1 (B); X1/X6/P1 (C), or a prime with a cocktail of P1/X3 VLP vaccine followed by a boost with a cocktail of P1/X6 VLP vaccine (D). Bars represent the geometric mean titer (+S.E.M.) from antisera collected at day 56.

DEFINITIONS

Figure 1G:
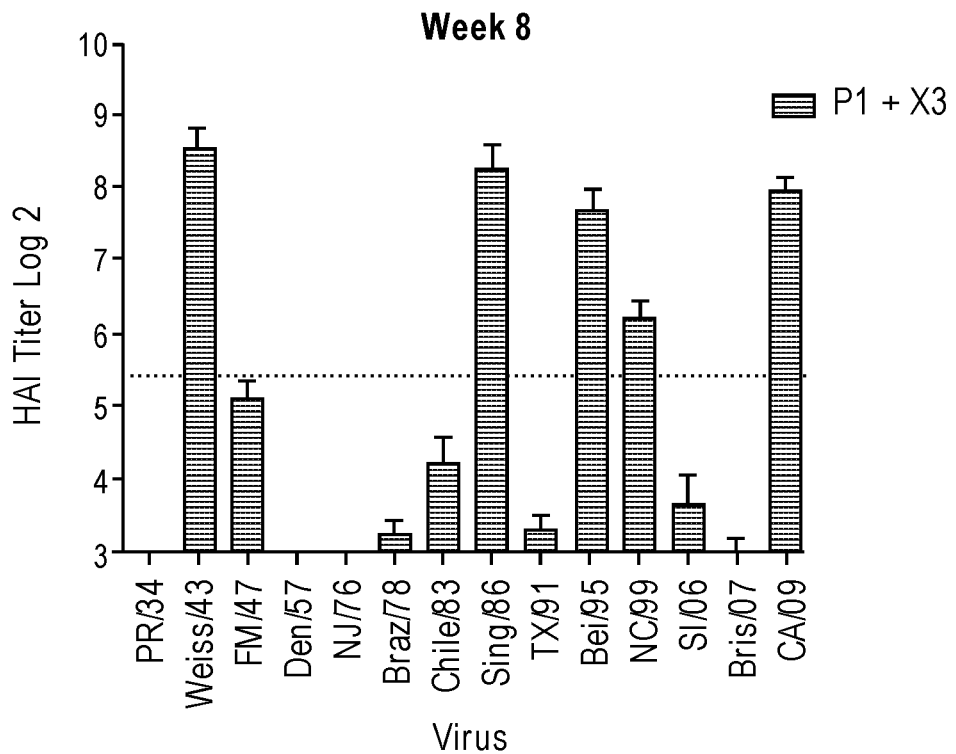

In order for the present invention to be more readily understood, certain terms are first defined below. Additional definitions for the following terms and other terms are set forth through the specification.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Adjuvant: As used herein, the term "adjuvant" refers to a substance or vehicle that non-specifically enhances the immune response to an antigen. Adjuvants can include a suspension of minerals (alum, aluminum salts, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as lipids and costimulatory molecules. Exemplary biological adjuvants include AS04 (Didierlaurent, A. M. et al, *J. Immunol.*, 2009, 183: 6186-6197), IL-2, RANTES, GM-CSF, TNF-α, IFN-γ, G-CSF, LFA-3, CD72, B7-1, B7-2, OX-40L and 41 BBL.

Administer: As used herein, "administering" a composition to a subject means to give, apply or bring the composition into contact with the subject. Administration can be accomplished by any of a number of routes, such as, for example, topical, oral, subcutaneous, intramuscular, intraperitoneal, intravenous, intrathecal and intradermal.

Antibody: As used herein, the term "antibody" refers to a polypeptide that includes canonical immunoglobulin sequence elements sufficient to confer specific binding to a particular target antigen. In some embodiments, as used herein, the term "antibody" also refers to an "antibody fragment" or "antibody fragments", which includes a portion of an intact antibody, such as, for example, the antigen-binding or variable region of an antibody. Examples of "antibody fragments" include Fab, Fab', F(ab')2, and Fv fragments; triabodies; tetrabodies; linear antibodies; single-chain antibody molecules; and CDR-containing moieties included in multi-specific antibodies formed from antibody fragments. Those skilled in the art will appreciate that the term "antibody fragment" does not imply and is not restricted to any particular mode of generation. An antibody fragment may be produced through use of any appropriate methodology, including but not limited to cleavage of an intact antibody, chemical synthesis, recombinant production, etc. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable ($V_H$) domain (located at the tips of the Y structure), followed by three constant domains: $C_H1$, $C_H2$, and the carboxy-terminal $C_H3$ (located at the base of the Y's stem). A short region, known as the "switch", connects the heavy chain variable and constant regions. The "hinge" connects $C_H2$ and $C_H3$ domains to the rest of the antibody. Two disulfide bonds in this hinge region connect the two heavy chain polypeptides to one another in an intact antibody. Each light chain is comprised of two domains—an amino-terminal variable ($V_L$) domain, followed by a carboxy-terminal constant (CO domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the $C_H2$ domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. Amino acid sequence comparisons among antibody polypeptide chains have defined two light chain (κ and λ) classes, several heavy chain (e.g., μ, γ, α, ε, δ) classes, and certain heavy chain subclasses (α1, α2, γ1, γ2, γ3, and γ4). Antibody classes (IgA [including IgA1, IgA2], IgD, IgE, IgG [including IgG1, IgG2, IgG3, IgG4], IgM) are defined based on the class of the utilized heavy chain sequences. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is monoclonal; in some embodiments, an antibody is polyclonal. In some embodiments, an antibody has constant region sequences that are characteristic of mouse, rabbit, primate, or human antibodies. In some embodiments, an antibody sequence elements are humanized, primatized, chimeric, etc., as is known in the art. Moreover, the term "antibody" as used herein, will be understood to encompass (unless otherwise stated or clear from context) can refer in appropriate embodiments to any of the art-known or developed constructs or formats for capturing antibody structural and functional features in alternative presentation. For example, in some embodiments, the term can refer to bi- or other multi-specific (e.g., zybodies, etc.) antibodies, Small Modular ImmunoPharmaceuticals ("SMIPs™"), single chain antibodies, camelid antibodies, and/or antibody fragments. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc.], or other pendant group [e.g., poly-ethylene glycol, etc.]).

Antigen: As used herein, the term "antigen", refers to an agent that elicits an immune response; and/or (ii) an agent that is bound by a T cell receptor (e.g., when presented by an MHC molecule) or to an antibody (e.g., produced by a B cell) when exposed or administered to an organism. In some embodiments, an antigen elicits a humoral response (e.g., including production of antigen-specific antibodies) in an organism; alternatively or additionally, in some embodiments, an antigen elicits a cellular response (e.g., involving T-cells whose receptors specifically interact with the antigen) in an organism. It will be appreciated by those skilled in the art that a particular antigen may elicit an immune response in one or several members of a target organism (e.g., mice, rabbits, primates, humans), but not in all members of the target organism species. In some embodiments, an antigen elicits an immune response in at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the members of a target organism species. In some embodiments, an antigen binds to an antibody and/or T cell receptor, and may or may not induce a particular physiological response in an organism. In some embodiments, for example, an antigen may bind to an antibody and/or to a T cell receptor in vitro, whether or not such an interaction occurs in vivo. In some embodiments, an antigen reacts with the products of specific humoral or cellular immunity, including those induced by heterologous immunogens. In some embodiments of the disclosed compositions and methods, influenza HA H1N1 protein is an antigen.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can be assessed in any of a variety of contexts—including where interacting entities or moieties are studied in isolation or in the context of more complex systems (e.g., while covalently or otherwise associated with a carrier entity and/or in a biological system or cell).

Carrier: As used herein, the term "carrier" refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

Co-administer: As used herein, "co-administer" and "co-administering" refer to the administration of at least two different optimized influenza HA proteins to a subject. In some embodiments, the at least two optimized influenza HA proteins may be administered at the same time as a combination or cocktail. In some embodiments, a first and second optimized influenza HA protein may be administered sequentially (e.g., a first optimized influenza HA protein is administered as a priming vaccine followed by administration of a second optimized influenza HA protein as a boosting vaccine), where the first optimized influenza HA protein is different from the second optimized influenza HA protein.

Codon-optimized: As used herein, a "codon-optimized" nucleic acid sequence refers to a nucleic acid sequence that has been altered such that translation of the nucleic acid sequence and expression of the resulting protein is improved optimized for a particular expression system. A "codon-optimized" nucleic acid sequence encodes the same protein as a non-optimized parental sequence upon which the "codon-optimized" nucleic acid sequence is based. For example, a nucleic acid sequence may be "codon-optimized" for expression in mammalian cells (e.g., CHO cells, human cells, mouse cells etc.), bacterial cells (e.g., *E. coli*), insect cells, yeast cells or plant cells.

Comparable: The term "comparable", as used herein, refers to two or more agents, entities, situations, sets of conditions, etc. that may not be identical to one another but that are sufficiently similar to permit comparison there between so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

Determine: Many methodologies described herein include a step of "determining". Those of ordinary skill in the art, reading the present specification, will appreciate that such "determining" can utilize any of a variety of techniques available to those skilled in the art, including for example specific techniques explicitly referred to herein. In some embodiments, a determination involves manipulation of a physical sample. In some embodiments, a determination involves consideration and/or manipulation of data or information, for example utilizing a computer or other processing unit adapted to perform a relevant analysis. In some embodiments, a determination involves receiving relevant information and/or materials from a source. In some embodiments, determining involves comparing one or more features of a sample or entity to a comparable reference.

Epitope: As used herein, the term "epitope" includes any moiety that is specifically recognized by an immunoglobulin (e.g., antibody or receptor) binding component in whole or in part. In some embodiments, an epitope is comprised of a plurality of chemical atoms or groups on an antigen. In some embodiments, such chemical atoms or groups are surface-exposed when the antigen adopts a relevant three-dimensional conformation. In some embodiments, such chemical atoms or groups are physically near to each other in space when the antigen adopts such a conformation. In some embodiments, at least some such chemical atoms are groups are physically separated from one another when the antigen adopts an alternative conformation (e.g., is linearized).

Excipient: As used herein, the term "excipient" refers to a non-therapeutic agent that may be included in a pharmaceutical composition, for example to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Expression: The term "expression", when used in reference to a nucleic acid herein, refers to one or more of the following events: (1) production of an RNA transcript of a DNA template (e.g., by transcription); (2) processing of an RNA transcript (e.g., by splicing, editing, 5' cap formation, and/or 3' end formation); (3) translation of an RNA into a polypeptide; and/or (4) post-translational modification of a polypeptide.

Fusion protein: As used herein, the term "fusion protein" refers to a protein encoded by a nucleic acid sequence engineered from nucleic acid sequences encoding at least a portion of two different (e.g., heterologous) proteins. As persons of skill are no doubt aware, to create a fusion protein nucleic acid sequences are joined such that the resulting reading does not contain an internal stop codon. In some embodiments, fusion proteins as described herein include an influenza HA polypeptide or fragment thereof.

H1N1 HA polypeptide: An "H1N1 HA polypeptide", as that term is used herein, is an HA polypeptide whose amino acid sequence includes at least one sequence element that is characteristic of H1N1 and distinguishes H1N1 from other HA subtypes. Representative sequence elements can be determined by alignments.

Host: The term "host" is used herein to refer to a system (e.g., a cell, organism, etc.) in which a polypeptide of interest is present. In some embodiments, a host is a system that is susceptible to infection with a particular infectious agent. In some embodiments, a host is a system that expresses a particular polypeptide of interest.

Host cell: As used herein, the phrase "host cell" refers to a cell into which exogenous DNA (recombinant or otherwise) has been introduced. For example, host cells may be used to produce the optimized influenza hemagglutinin polypeptides described herein by standard recombinant techniques. Persons of skill upon reading this disclosure will understand that such terms refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, host cells include any prokaryotic and eukaryotic cells suitable for expressing an exogenous DNA (e.g., a recombinant nucleic acid sequence). Exemplary cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6™ cell).

Immune response: As used herein, the term "immune response" refers to a response of a cell of the immune system, such as a B cell, T cell, dendritic cell, macrophage or polymorphonucleocyte, to a stimulus such as an antigen or vaccine. An immune response can include any cell of the body involved in a host defense response, including for example, an epithelial cell that secretes an interferon or a cytokine. An immune response includes, but is not limited to, an innate and/or adaptive immune response. As used herein, a protective immune response refers to an immune response that protects a subject from infection (prevents infection or prevents the development of disease associated with infection). Methods of measuring immune responses are well known in the art and include, for example, measuring proliferation and/or activity of lymphocytes (such as B or T cells), secretion of cytokines or chemokines, inflammation, antibody production and the like.

Immunogen: As used herein, the term "immunogen" refers to a compound, composition, or substance which is capable, under appropriate conditions, of stimulating an immune response, such as the production of antibodies or a T cell response in an animal, including compositions that are injected or absorbed into an animal. As used herein, an "immunogenic composition" is an administrable composition comprising an immunogen (such as an HA polypeptide). "Immunogenic compositions" include, for example, vaccines. As used herein, "immunize" means to render a subject protected from an infectious disease, such as by vaccination.

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Influenza vaccine: As used herein, the term "influenza vaccine" or "vaccine" refers to an immunogenic composition capable of stimulating an immune response, administered for the prophylaxis, prevention, amelioration, or treatment of influenza virus infection. An influenza vaccine may include, for example, attenuated or killed influenza virus, subunit preparations thereof (i.e., split-inactivated vaccines), virus-like particles (VLPs) and/or antigenic polypeptides (e.g., the computationally optimized hemagglutinins described herein) or DNA derived from them, or any recombinant versions of such immunogenic materials. Influenza vaccines as described herein may optionally contain one or more adjuvants.

Isolated: As used herein, the term "isolated" refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

Nucleic acid: As used herein, the phrase "nucleic acid", in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is single stranded; in some embodiments, a nucleic acid is double stranded. In some embodiments a nucleic acid has a nucleotide sequence comprising at least one element that encodes, or is the complement of a sequence that encodes, a polypeptide. In some embodiments, a nucleic acid has enzymatic activity.

Optimized influenza HA protein: As used herein, "optimized influenza HA protein," "optimized H1N1 influenza HA polypeptide," or "computationally optimized" refer to a non-naturally occurring HA protein consensus sequence generated by sequence alignments of human H1N1 influenza viruses isolates or human and swine H1N1 influenza virus isolates (as described in, for example, international publication WO2013/148164 and U.S. publication US2014/0147459 to Ross, T. M. et al., which are incorporated by reference herein in their entirety). Nucleotide sequences encoding optimized HA proteins are further optimized for expression in mammalian cells via codon-optimization and RNA optimization (such as to increase RNA stability). Optimized influenza HA proteins disclosed herein (and set forth herein as SEQ ID NO: 1, SEQ ID NO: 2, SEQ ID NO: 3, and SEQ ID NO: 4) are also referred to as "COBRA" (computationally-optimized broadly reactive antigen) sequences. Optimized HA polypeptides are designed to elicit broadly reactive immune responses in a subject. Their amino acid sequences have been designed by humans and/or their existence and production require action of humans. For example, the computationally optimized HA polypeptides described herein have an amino acid sequence that differs from the amino acid sequences of HA polypeptides found in natural influenza isolates. In the context of the present disclosure, "broadly reactive" means the protein sequence elicits an immune response in a subject that is sufficient to inhibit, neutralize or prevent infection of a broad range of H1N1 influenza viruses (such as most or all influenza viruses within a specific subtype). Co-administration of the optimized H1N1 influenza HA proteins are capable of eliciting an immune response, such as a protective immune response, against both pandemic and seasonal H1N1 influenza strains.

Operably linked: As used herein, the phrase "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism. For example, in prokaryotes, such control sequences generally include promoter, ribosomal binding site, and transcription termination sequence, while in eukaryotes, typically, such control sequences include promoters and transcription termination sequence. The term "control sequences" is intended to include components whose presence is essential for expression and processing, and can also include additional components whose presence is advantageous, for example, leader sequences and fusion partner sequences.

Outbreak: As used herein, an influenza virus "outbreak" refers to a collection of virus isolates from within a single country in a given year.

Pandemic strain: A "pandemic" influenza strain is one that has caused or has capacity to cause pandemic infection of human populations. In some embodiments, a pandemic strain has caused pandemic infection. In some embodiments, such pandemic infection involves epidemic infection across multiple territories; in some embodiments, pandemic infection involves infection across territories that are separated from one another (e.g., by mountains, bodies of water, as part of distinct continents, etc.) such that infections ordinarily do not pass between them. In some embodiments, a pandemic strain is A/California/07/2009 H1N1.

Pharmaceutically acceptable vehicles: The pharmaceutically acceptable carriers (vehicles) useful in this disclosure are conventional. Remington's Pharmaceutical Sciences, by E. W. Martin, Mack Publishing Co., Easton, Pa., 15$^{th}$ Edition (1975), describes compositions and formulations suitable for pharmaceutical delivery of one or more therapeutic compositions, such as one or more influenza vaccines, and additional pharmaceutical agents. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally. In some embodiments, the term "polypeptide" is used to refer to specific functional classes of polypeptides, such as, HA polypeptides, etc. In some embodiments, a useful polypeptide (e.g., a computationally optimized H1 HA polypeptide as described herein) may comprise or consist of a fragment of a parent polypeptide (e.g., an epitope). In some embodiments, a useful polypeptide as may comprise or consist of multiple (e.g., two, three, four, etc.) fragments (e.g., epitopes), each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide. Alternatively, in some embodiments, a useful polypeptide may comprise or consist of multiple (e.g., two, three, four, etc.) fragments (e.g., epitopes), each of which is found in different parent polypeptides than the polypeptide of interest (e.g., fragments that originate in different parent polypeptides, and/or fragments may be present in a different order in the polypeptide of interest than in the parent polypeptides), so that the polypeptide of interest is a derivative of its parent polypeptides.

Prevention: The term "prevention", as used herein, refers to prophylaxis, avoidance of disease manifestation, a delay of onset, and/or reduction in frequency and/or severity of one or more symptoms of a particular disease, disorder or condition (e.g., infection for example with influenza virus). In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition.

Pure: As used herein, an agent or entity is "pure" if it is substantially free of other components. For example, a preparation that contains more than about 90% of a particular agent or entity is typically considered to be a pure preparation. In some embodiments, an agent or entity is at least 91%, at least 92%, at least 93%, at least 94%, at least 95%, at least 96%, at least 97%, at least 98%, or at least 99% pure.

Recombinant: As used herein, the term "recombinant" is intended to refer to polypeptides (e.g., HA polypeptides as described herein) that are designed, engineered, prepared, expressed, created or isolated by recombinant means, such as polypeptides expressed using a recombinant expression vector transfected into a host cell, polypeptides isolated from a recombinant, combinatorial polypeptide library or polypeptides prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source. In some embodiments, one or more such selected sequence elements results from the combination of multiple (e.g., two or more) known sequence elements that are not naturally present in the same polypeptide (e.g., two epitopes from two separate H1 HA polypeptides).

Reference: The term "reference" is often used herein to describe a standard or control agent, individual, population, sample, sequence or value against which an agent, individual, population, sample, sequence or value of interest is compared. In some embodiments, a reference agent, individual, population, sample, sequence or value is tested and/or determined substantially simultaneously with the testing or determination of the agent, individual, population, sample, sequence or value of interest. In some embodiments, a reference agent, individual, population, sample, sequence or value is a historical reference, optionally embodied in a tangible medium. Typically, as would be understood by those skilled in the art, a reference agent, individual, population, sample, sequence or value is determined or characterized under conditions comparable to those utilized to determine or characterize the agent, individual, population, sample, sequence or value of interest.

Seasonal strain: A "seasonal" influenza strain is one that has caused or has capacity to cause a seasonal infection (e.g., annual epidemic) of human populations. In some embodiments, a seasonal strain has caused seasonal infection.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a given gene or protein will possess a relatively high degree of sequence identity when aligned using standard methods. Methods of alignment of sequences for comparison are well known in the art. Various programs and alignment algorithms are described in: Smith and Waterman, Adv. Appl. Math. 2:482, 1981; Needleman and Wunsch, J. Mol. Biol. 48:443, 1970; Pearson and Lipman, Proc. Natl. Acad. Sci. U.S.A. 85:2444, 1988; Higgins and Sharp, Gene 73:237-244, 1988; Higgins and Sharp, CABIOS 5:151-153, 1989; Corpet et al., Nucleic Acids Research 16:10881-10890, 1988; and Pearson and Lipman, Proc. Natl. Acad. Sci. U.S.A. 85:2444, 1988. Altschul et al., Nature Genet. 6:119-129, 1994. The NCBI Basic Local Alignment Search Tool (BLAST™) (Altschul et al., J. Mol. Biol. 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

Subject: As used herein, the term "subject" means any mammal, including mice, ferrets and humans. In certain embodiments of the present invention the subject is an adult, an adolescent or an infant. In some embodiments, terms "individual" or "patient" are used and are intended to be interchangeable with "subject". Also contemplated by the present invention are the co-administration of the optimized H1N1 influenza HA proteins and/or performance of the methods to swine.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Transformation: As used herein, refers to any process by which exogenous DNA is introduced into a host cell. Transformation may occur under natural or artificial conditions using various methods well known in the art. Transformation may rely on any known method for the insertion of foreign nucleic acid sequences into a prokaryotic or eukaryotic host cell. In some embodiments, a particular transformation methodology is selected based on the host cell being transformed and may include, but is not limited to, viral infection, electroporation, mating, lipofection. In some embodiments, a "transformed" cell is stably transformed in that the inserted DNA is capable of replication either as an autonomously replicating plasmid or as part of the host chromosome. In some embodiments, a transformed cell transiently expresses introduced nucleic acid for limited periods of time.

Vaccination: As used herein, the term "vaccination" refers to the administration of a composition (specifically co-administration of two or more of the computationally optimized H1N1 HA polypeptides disclosed herein) intended to generate an immune response, for example to a disease-causing agent such as influenza. Vaccination can be administered before, during, and/or after exposure to a disease-causing agent, and/or to the development of one or more symptoms, and in some embodiments, before, during, and/or shortly after exposure to the agent. Vaccines may elicit both prophylactic (preventative) and therapeutic responses. Methods of administration vary according to the vaccine, but may include inoculation, ingestion, inhalation or other forms of administration. Inoculations can be delivered by any of a number of routes, including parenteral, such as intravenous, subcutaneous or intramuscular. Vaccines may be administered with an adjuvant to boost the immune response. In some embodiments, vaccination includes multiple administrations, appropriately spaced in time, of a vaccinating composition.

Vector: As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors."

Virus-like particle (VLP): As used herein, the phrase "virus-like particle" or "VLP" refers to particles that resemble a virus yet lack any viral genetic material and, therefore, are not infectious. A "virus-like particle" or "VLP" may be produced by heterologous expression in a variety of cell culture systems including mammalian cell lines, insect cell lines, yeast, and plant cells. In addition, VLPs can be purified by methods known in the art. In some embodiments, influenza VLPs as described herein comprise hemagglutinin (HA) polypeptides and neuraminidase (NA) polypeptides. In some embodiments, influenza VLPs as described herein comprises HA polypeptides, NA polypeptides and/or viral structural polypeptides (e.g., an influenza structural protein such as influenza M1). In some certain embodiments, influenza VLPs as described herein comprises HA polypeptides, NA polypeptides and/or M1 polypeptides. In some embodiments, influenza VLPs as described herein comprises HA polypeptides, NA polypeptides and/or HIV gag polypeptides. As persons of skill are aware, other viral structural proteins may be used as alternatives to those exemplified herein. Influenza VLPs can be produced by transfection of host cells (e.g., mammalian cells) with plasmids encoding HA and NA proteins, and optionally HIV gag proteins. After incubation of the transfected cells for an appropriate time to allow for protein expression (such as for approximately 72 hours), VLPs can be isolated from cell culture supernatants. In some embodiments, influenza VLPs as described herein are produced by transient transfection in mammalian cells (e.g., human cells). In some embodiments, influenza VLPs are analyzed by the use of one or more assays. To give but a few examples, influenza VLPs may be analyzed for hemagglutinin activity, dynamic light scattering and hemagglutinin content quantitation by protein staining. Other assays will be readily apparent to persons of skill upon reviewing the present disclosure.

DETAILED DESCRIPTION OF CERTAIN EMBODIMENTS

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

Co-Administration of H1N1 Hemagglutinin Computationally Optimized Broadly Reactive Antigens (COBRAs)

Influenza A viruses belong to the family Orthomyxoviridae. They are classified on the basis of their hemagglutinin (HA) and neuraminidase (NA) proteins into 16 HA subtypes (H1-H16) and 9 NA subtypes (N1-N9). The HA protein plays an important role in mediating binding of the virus to cellular receptors and fusing of the viral and endosomal membranes. The NA protein promotes release of virus from infected cells by removing sialic acid from cellular and viral HA and NA proteins. The amino acid sequence of the major antigens of influenza, particularly HA, is highly variable across groups, subtypes and strains due to antigenic drift and, less frequently, antigenic shift. Disclosed herein are influenza vaccines that overcome the challenge of H1N1 antigenic diversity by generating universal, broadly-reactive, protective sterilizing immunity against a broad spectrum of H1N1 influenza strains, including both seasonal and pandemic strains.

Embodiments disclosed herein rely on a methodology of antigen design using multiple rounds of consensus generation termed computationally optimized broadly reactive antigen (COBRA). This method was designed to address the diversity within H1N1 HA and utilized global surveillance efforts to generate a vaccine with the potential to elicit increased breadth of antibody responses within this antigenically diverse polypeptide. Several H1N1 HA computationally optimized antigens (COBRAs) were designed based upon selected H1N1 viruses isolated from 1918-2012, including 1) human and swine influenza strains from 1933-2011 (P1), 2) human influenza strains from 1999-2012 (X6), 3) human influenza strains from 1978-2008 (X3), and 4) human influenza strains from 1918-2012.

Provided herein is co-administration of H1N1 COBRA HA that expands the breadth of antibody responses in a subject against different H1N1 influenza strains, including both seasonal and pandemic H1N1 strains. Co-administration of the present invention includes novel combinations or cocktails of H1N1 COBRA HA proteins, as well as prime-boost administration of H1N1 COBRA HA proteins The compositions described herein comprise combinations or cocktails of optimized hemagglutinin molecules of the H1N1 subtype that do not match naturally occurring strains. In combination, these molecules act synergistically to provide broader coverage to naturally occurring H1N1 strains (both seasonal and pandemic) than either molecule can provide individually. The synergy of the combinations/cocktails described herein is empirically verifiable. For example, as described in the accompanying Examples, each of the COBRA HA proteins were expressed on virus-like particles (VLPs) and purified as vaccine immunogens. Cocktails of the H1N1 COBRA HA VLPs were administered to mice and the humoral immune response to a panel of influenza strains spanning multiple decades was measured. Co-administration of certain seasonal H1N1 COBRA HA VLPs had an antagonistic effect on the antibody response to certain influenza strains. The addition of a pandemic H1N1 COBRA VLP to the cocktail elicited a strong antibody response to a pandemic influenza strain but also surprisingly expanded the breadth of antibody response to the seasonal influenza strains tested. Co-administration of the H1N1 COBRA VLPs in a prime-boost regimen, elicited broadly reactive HAI activity against H1N1 influenza strains depending on the combination of COBRAs used and the order of administration. Co-administration of the seasonal H1N1 COBRA VLPs resulted in little or no activity against a pandemic H1N1 strain or historical H1N1 strains (1934-1957). Combining the pandemic P1 COBRA VLP with a seasonal COBRA VLP resulted in strong antibody activity against the pandemic H1N1 strain and in certain instances synergistically expanded the breadth of antibody response to seasonal influenza strains. Priming with the P1 COBRA VLP generally elicited higher HIA titers than boosting with the P1 COBRA VLP. In other instances, changing the order of administration had antagonistic effects. Collectively, the findings demonstrate that co-administration of a pandemic H1N1 COBRA and a seasonal H1N1 COBRA synergistically expanded the breadth of immune response against a panel of historical influenza viruses and that the order of administering H1N1 COBRAs in a prime-boost regimen is important.

The amino acid sequences of the particular optimized HA polypeptides utilized in embodiments of the invention are set forth herein as SEQ ID NO: 1, SEQ ID NO: 2, SEQ ID NO: 3, and SEQ ID NO: 4.

TABLE 1

| | |
|---|---|
| Pandemic H1N1 COBRA (Human and Swine 1933-2011): P1 | MKARLLVLLCALAATDADTICIGYHANNSTDTVDTVLEKNVTVTHS VNLLEDSHNGKLCKLKGIAPLQLGKCNIAGWLLGNPECESLLSARS WSYIVETPNSENGTCYPGDFIDYEELREQLSSVSSFERFEIFPKESSW PNHNTTKGVTAACSHAGKSSFYRNLLWLTKKGGSYPKLSKSYVNNK |

TABLE 1 -continued

| | |
|---|---|
| | GKEVLVLWGVHHPSTSTDQQSLYQNENAYVSVVSSNYNRRFTPEI<br>AERPKVRGQAGRMNYYWTLLEPGDTIIFEATGNLIAPWYAFALSRG<br>SGSGIITSNASMHECNTKCQTPQGAINSSLPFQNIHPVTIGECPKYV<br>RSTKLRMVTGLRNIPSIQSRGLFGAIAGFIEGGWTGMIDGWYGYH<br>HQNEQGSGYAADQKSTQNAINGITNKVNSVIEKMNTQFTAVGKE<br>FNNLEKRMENLNKKVDDGFLDIWTYNAELLVLLENERTLDFHDSNV<br>KNLYEKVKSQLRNNAKEIGNGCFEFYHKCDNECMESVKNGTYDYP<br>KYSEESKLNREKIDGVKLESMGVYQILAIYSTVASSLVLLVSLGAISFW<br>MCSNGSLQCRICI (SEQ ID NO: 1) |
| Seasonal H1N1<br>COBRA (Human<br>1999-2012): X6 | MEARLLVLLCAFAATNADTICIGYHANNSTDTVDTVLEKNVTVTHS<br>VNLLEDSHNGKLCLLKGIAPLQLGNCSVAGWILGNPECELLISKESW<br>SYIVETPNPENGTCYPGYFADYEELREQLSSVSSFERFEIFPKESSWP<br>NHTVTGVSASCSHNGKSSFYRNLLWLTGKNGLYPNLSKSYANNKEK<br>EVLVLWGVHHPPNIGDQRALYHTENAYVSVVSSHYSRKFTPEIAKR<br>PKVRDQEGRINYYWTLLEPGDTIIFEANGNLIAPRYAFALSRGFGSGI<br>ITSNAPMDECDAKCQTPQGAINSSLPFQNVHPVTIGECPKYVRSAK<br>LRMVTGLRNIPSIQSRGLFGAIAGFIEGGWTGMVDGWYGYHHQN<br>EQGSGYAADQKSTQNAINGITNKVNSVIEKMNTQFTAVGKEFNKL<br>ERRMENLNKKVDDGFLDIWTYNAELLVLLENERTLDFHDSNVKNLY<br>EKVKSQLKNNAKEIGNGCFEFYHKCNNECMESVKNGTYDYPKYSEE<br>SKLNREKIDGVKLESMGVYQILAIYSTVASSLVLLVSLGAISFWMCSN<br>GSLQCRICI (SEQ ID NO: 2) |
| Seasonal H1N1<br>COBRA (Human<br>1978-2008): X3 | MEARLLVLLCAFAATNADTICIGYHANNSTDTVDTVLEKNVTVTHS<br>VNLLEDSHNGKLCRLKGIAPLQLGNCSVAGWILGNPECESLFSKES<br>WSYIAETPNPENGTCYPGYFADYEELREQLSSVSSFERFEIFPKESSW<br>PNHTVTKGVTASCSHNGKSSFYRNLLWLTEKNGLYPNLSKSYVNNK<br>EKEVLVLWGVHHPSNIGDQRAIYHTENAYVSVVSSHYSRRFTPEIAK<br>RPKVRDQEGRINYYWTLLEPGDTIIFEANGNLIAPWYAFALSRGFGS<br>GIITSNASMDECDAKCQTPQGAINSSLPFQNVHPVTIGECPKYVRST<br>KLRMVTGLRNIPSIQSRGLFGAIAGFIEGGWTGMIDGWYGYHHQN<br>EQGSGYAADQKSTQNAINGITNKVNSVIEKMNTQFTAVGKEFNKL<br>ERRMENLNKKVDDGFLDIWTYNAELLVLLENERTLDFHDSNVKNLY<br>EKVKSQLKNNAKEIGNGCFEFYHKCNNECMESVKNGTYDYPKYSEE<br>SKLNREKIDGVKLESMGVYQILAIYSTVASSLVLLVSLGAISFWMCSN<br>GSLQCRICI (SEQ ID NO: 3) |
| Seasonal H1N1<br>COBRA (Human<br>1918-2012): X1 | MEARLLVLLCAFAATNADTICIGYHANNSTDTVDTVLEKNVTVTHS<br>VNLLEDSHNGKLCRLKGIAPLQLGKCNIAGWILGNPECESSLSKRSW<br>SYIVETPNSENGTCYPGDFIDYEELREQLSSVSSFERFEIFPKESSWPN<br>HNTTKGVTAACSHAGKSSFYRNLLWLTKKNGSYPNLSKSYVNNKG<br>KEVLVLWGVHHPSNIEDQQSLYQNENAYVSVVSSNYNRRFTPEIAK<br>RPKVRDQEGRMNYYWTLLEPGDTIIFEANGNLIAPWYAFALSRGF<br>GSGIITSNASMHECDTKCQTPQGAINSSLPFQNIHPVTIGECPKYVR<br>STKLRMVTGLRNIPSIQSRGLFGAIAGFIEGGWTGMIDGWYGYHH<br>QNEQGSGYAADQKSTQNAINGITNKVNSVIEKMNTQFTAVGKEF<br>NNLEKRMENLNKKVDDGFLDIWTYNAELLVLLENERTLDFHDSNV<br>KNLYEKVKSQLKNNAKEIGNGCFEFYHKCNNECMESVKNGTYDYP<br>KYSEESKLNREKIDGVKLESMGVYQILAIYSTVASSLVLLVSLGAISFW<br>MCSNGSLQCRICI (SEQ ID NO: 4) |

Particularities concerning the design and production of these molecules have been described previously, particularly in International Publication WO2013/148164 and U.S. Publication 2014/0147459, which are incorporated herein by reference in their entirety. The optimized pandemic H1N1 HA polypeptide was developed through a series of HA protein alignments, and subsequent generation of consensus sequences based on 156 human influenza strains and 49 swine H1N1 influenza strains isolated between 1933-2011. The optimized seasonal X6 H1N1 HA polypeptide was developed through a series of HA protein alignments, and subsequent generation of consensus sequences based on 1273 human influenza strains isolated between 1999-2012. The optimized seasonal X3 H1N1 HA polypeptide was developed through a series of HA protein alignments, and subsequent generation of consensus sequences based on 1204 human influenza strains isolated between 1978-2008. The optimized seasonal X1 H1N1 HA polypeptide was developed through a series of HA protein alignments, and subsequent generation of consensus sequences based on 1448 human influenza strains isolated between 1918-2012.

Provided herein are non-naturally occurring variants of the optimized, recombinant influenza HA polypeptides. In certain embodiments, the recombinant, optimized influenza HA polypeptide comprises an amino acid sequence at least 98%, 98.5%, 99% or 99.5% identical to SEQ ID NO: 1. Also provided is a recombinant, optimized influenza HA polypeptide comprising an amino acid sequence at least 99% or 99.5% identical to SEQ ID NO: 2. Also provided is a recombinant, optimized influenza HA polypeptide comprising an amino acid sequence at least 99% or 99.5% identical to SEQ ID NO: 3. Also provided is a recombinant, optimized influenza HA polypeptide comprising an amino acid sequence at least 96%, 96.5%, 97%, 97.5%, 98%, 98.5%, 99%, or 99.5% identical to SEQ ID NO: 4.

In another embodiment, the recombinant, optimized influenza HA polypeptide comprises an amino acid sequence at least 98%, 98.5%, 99% or 99.5% identical to residues 2-566 of SEQ ID NO: 1. In another embodiment, the recombinant, optimized influenza HA polypeptide comprising an amino acid sequence at least 99% or 99.5% identical to residues 2-565 of SEQ ID NO: 2. In yet another embodiment, the recombinant, optimized influenza HA polypeptide comprises an amino acid sequence at least 99% or 99.5% identical to residues 2-566 of SEQ ID NO: 3. In another embodiment, the recombinant, optimized influenza HA polypeptide comprises an amino acid sequence at least 96%, 96.5%, 97%, 97.5%, 98%, 98.5%, 99%, or 99.5% identical to residues 2-566 of SEQ ID NO: 4.

In other embodiments, the amino acid sequence of the optimized influenza HA polypeptide comprises (i) no more than 8, no more than 7, no more than 6, no more than 5, nor more than 4, no more than 3, no more than 2 or no more than 1 amino acid substitution(s) relative to SEQ ID NO: 1; (ii) no more than 6, no more than 5, no more than 4, no more than 3, no more than 2 or no more than 1 amino acid substitution(s) relative to SEQ ID NO: 2; (iii) no more than 6, no more than 5, nor more than 4, no more than 3, no more than 2 or no more than 1 amino acid substitution(s) relative to SEQ ID NO: 3; (iv) no more than 10, no more than 9, no more than 8, no more than 7, no more than 6, no more than 5, nor more than 4, no more than 3, no more than 2 or no more than 1 amino acid substitution(s) relative to SEQ ID NO: 4.

In some embodiments, the optimized influenza HA polypeptide comprises or consists of the amino acid sequence of residues 2-566 of SEQ ID NO: 1, residues 2-565 of SEQ ID NO: 2, residues 2-566 of SEQ ID NO: 3, or residues 2-566 of SEQ ID NO: 4. In other embodiments, the optimized influenza HA polypeptide comprises or consists of the amino acid sequence of SEQ ID NO: 1, SEQ ID NO: 2, SEQ ID NO: 3, or SEQ ID NO: 4.

Further provided are isolated nucleic acid molecules encoding a recombinant influenza HA polypeptide disclosed herein. In some embodiments, the nucleic acid molecule is codon-optimized for expression in mammalian cells. The nucleic acid molecule is optionally further optimized for RNA stability.

In one embodiment, the nucleic acid molecule comprises a nucleic acid sequence encoding the amino acid sequence of SEQ ID NO: 1 or residues 2-566 of SEQ ID NO: 1. In another embodiment, the nucleic acid molecule comprises a nucleic acid sequence encoding the amino acid sequence of SEQ ID NO: 2 or residues 2-565 of SEQ ID NO: 2. In another embodiment, the nucleic acid molecule comprises a nucleic acid sequence encoding the amino acid sequence of SEQ ID NO: 3 or residues 2-566 of SEQ ID NO: 3. In another embodiment, the nucleic acid molecule comprises a nucleic acid sequence encoding the amino acid sequence of SEQ ID NO: 4 or residues 2-566 of SEQ ID NO: 4. Optimized influenza HA polypeptides encoded by the nucleic acid molecules, vectors comprising the nucleic acid molecules, and host cells containing the disclosed vectors are also provided herein.

Expression of nucleic acid molecules in accordance with the present invention may be regulated by a second nucleic acid sequence so that the molecule is expressed in a host transformed with the recombinant DNA molecule. For example, expression of the nucleic acid molecules of the invention may be controlled by a promoter and/or enhancer element, which are known in the art.

Nucleic acid constructs of the present invention are inserted into an expression vector or viral vector by methods known to the art, and nucleic acid molecules are operatively linked to an expression control sequence.

An expression vector containing a nucleic acid molecule is transformed into a suitable host cell to allow for production of the protein encoded by the nucleic acid constructs. Exemplary host cells include prokaryotes (e.g., *E. coli*) and eukaryotes (e.g., a COS, 293 or CHO cell). Host cells transformed with an expression vector are grown under conditions permitting production of an optimized HA polypeptide the present invention followed by recovery of an optimized HA polypeptide.

Vectors comprising the nucleic acid molecules encoding recombinant HA polypeptides are also provided by the present disclosure. The vector can be any suitable vector for expression of the HA polypeptide, such as a mammalian expression vector. In particular examples, the vector is the pTR600 expression vector (U.S. Patent Application Publication No. 2002/0106798, herein incorporated by reference; Ross et ah, Nat Immunol. 1(2): 102-103, 2000; Green et al., Vaccine 20:242-248, 2001). In some examples, the vector includes a promoter operably linked to the nucleic acid sequence encoding the HA polypeptide. In particular examples, the promoter is a CMV promoter.

Fusion proteins comprising one or more of the optimized influenza HA polypeptides as described herein (e.g., an HA polypeptide that appears in Table 1) are further provided by the present disclosure.

Provided herein are compositions (i.e., cocktails) comprising combinations of recombinant H1N1 influenza HA polypeptides having an optimized amino acid sequence for eliciting a broadly reactive immune response against H1N1 influenza. In some embodiments, the compositions described herein comprise (i) a first optimized influenza HA polypeptide comprising an amino acid sequence at least 98%, 98.5%, 99%, or 99.5% identical to SEQ ID NO: 1, and (ii) second optimized influenza HA polypeptide comprising an amino acid sequence at least 99% or at least 99.5% identical to SEQ ID NO: 2. In particular embodiments, the amino acid sequence of the first optimized influenza HA polypeptide that is at least 98%, 98.5%, 99%, or 99.5% identical to SEQ ID NO: 1 lacks the N-terminal methionine residue. In particular embodiments, the amino acid sequence of the second optimized influenza HA polypeptide that is at least 99% or at least 99.5% identical to SEQ ID NO: 2 lacks the N-terminal methionine residue. In some embodiments, the cocktails comprise a first optimized influenza HA polypeptide comprising an amino acid sequence at least 98%, 98.5%, 99%, or 99.5% identical to residues 2-566 of SEQ ID NO: 1 and a second optimized influenza HA polypeptide comprising an amino acid sequence at least 99% or at least 99.5% identical to residues 2-565 of SEQ ID NO: 2. In particular examples, the amino acid sequences of the first and second optimized influenza HA polypeptides comprise or consists of the amino acid sequence of residues 2-566 of SEQ ID NO: 1 and residues 2-565 of SEQ ID NO: 2, respectively. In some embodiments, the cocktails comprise a first optimized influenza HA polypeptide comprising an amino acid sequence at least 99.5% identical to residues 2-566 of SEQ ID NO: 1 and a second optimized influenza HA polypeptide comprising an amino acid sequence at least 99.5% identical to residues 2-565 of SEQ ID NO: 3. In some embodiments, the amino acid sequences of the optimized influenza HA polypeptides in the composition are at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, or at least 99.9% identical to SEQ ID NO: 1, SEQ ID NO: 2, residues 2-566 of SEQ ID NO: 1 or residues 2-565 of SEQ ID NO: 2. In some embodiments, the amino acid sequences of the optimized influenza HA polypeptides in the composition are 100% homologous to SEQ ID NO: 1, SEQ ID NO: 2, residues 2-566 of SEQ ID NO: 1 or residues 2-565 of SEQ ID NO: 2. In some embodiments, the compositions comprise at least two different optimized influenza HA polypeptides, wherein the amino acid sequence of the polypeptides comprises no more than two, or no more than one substitution relative to SEQ ID NO: 1 or SEQ ID NO: 2.

In some embodiments, the compositions described herein comprise (i) a first optimized influenza HA polypeptide comprising an amino acid sequence at least 98%, 98.5%, 99%, or 99.5% identical to SEQ ID NO: 1, and (ii) second optimized influenza HA polypeptide comprising an amino acid sequence at least 99% or 99.5% identical to SEQ ID NO: 3. In particular embodiments, the amino acid sequence of the first optimized influenza HA polypeptide that is at least 98%, 98.5%, 99%, or 99.5% identical to SEQ ID NO: 1 lacks the N-terminal methionine residue. In particular embodiments, the amino acid sequence of the second optimized influenza HA polypeptide that is at least 99% or 99.5% identical to SEQ ID NO: 3 lacks the N-terminal methionine residue. In particular embodiments, the amino acid sequence of the first optimized influenza HA polypeptide is at least 98%, 98.5%, 99%, or 99.5% identical to residues 2-566 of SEQ ID NO: 1. In particular embodiments, the amino acid sequence of the second optimized influenza HA polypeptide is at least 99% or 99.5% identical to residues 2-566 of SEQ ID NO: 3. In particular embodiments, the amino acid sequence of the first optimized influenza HA polypeptide comprises or consists of residues 2-566 of SEQ ID NO: 1. In particular embodiments, the amino acid sequence of the second optimized influenza HA polypeptide comprises or consists of residues 2-566 of SEQ ID NO: 3. In some embodiments, the amino acid sequences of the optimized influenza HA polypeptides in the composition are at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, or at least 99.9% identical to SEQ ID NO: 1, SEQ ID NO: 3, residues 2-566 of SEQ ID NO: 1 or residues 2-566 of SEQ ID NO: 3. In some embodiments, the amino acid sequences of the optimized influenza HA polypeptides in the composition are 100% homologous to SEQ ID NO: 1, SEQ ID NO: 3, residues 2-566 of SEQ ID NO: 1 or residues 2-566 of SEQ ID NO: 3. In some embodiments, the compositions comprise at least two different optimized influenza HA polypeptides, wherein the amino acid sequence of the polypeptides comprises no more than two, or no more than one substitution relative to SEQ ID NO: 1 or SEQ ID NO: 3.

In some embodiments, the compositions described herein comprise (i) a first optimized influenza HA polypeptide comprising an amino acid sequence at least 98%, 98.5%, 99%, or 99.5% identical to SEQ ID NO: 1, and (ii) second optimized influenza HA polypeptide comprising an amino acid sequence at least 96%, 96.5%, 97%, 97.5%, 98%, 98.5%, 99%, or 99.5% identical to SEQ ID NO: 4. In particular embodiments, the amino acid sequence of the first optimized influenza HA polypeptide that is at least 98%, 98.5%, 99%, or 99.5% identical to SEQ ID NO: 1 lacks the N-terminal methionine residue. In particular embodiments, the amino acid sequence of the second optimized influenza HA polypeptide that is at least 99% or 99.5% identical to SEQ ID NO: 4 lacks the N-terminal methionine residue. In particular embodiments, the amino acid sequence of the first optimized influenza HA polypeptide is at least 98%, 98.5%, 99%, or 99.5% identical to residues 2-566 of SEQ ID NO: 1. In particular embodiments, the amino acid sequence of the second optimized influenza HA polypeptide is at least 99% or 99.5% identical to residues 2-566 of SEQ ID NO: 4. In particular embodiments, the amino acid sequence of the first optimized influenza HA polypeptide comprises or consists of residues 2-566 of SEQ ID NO: 1. In particular embodiments, the amino acid sequence of the second optimized influenza HA polypeptide comprises or consists of residues 2-566 of SEQ ID NO: 4. In some embodiments, the amino acid sequences of the optimized influenza HA polypeptides in the composition are at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, or at least 99.9% identical to SEQ ID NO: 1, SEQ ID NO: 4, residues 2-566 of SEQ ID NO: 1 or residues 2-566 of SEQ ID NO: 4. In some embodiments, the amino acid sequences of the optimized influenza HA polypeptides in the composition are 100% homologous to SEQ ID NO: 1, SEQ ID NO: 4, residues 2-566 of SEQ ID NO: 1 or residues 2-566 of SEQ ID NO: 4. In some embodiments, the compositions comprise at least two different optimized influenza HA polypeptides, wherein the amino acid sequence of the polypeptides comprises no more than two, or no more than one substitution relative to SEQ ID NO: 1 or SEQ ID NO: 4.

In some embodiments, the compositions described herein comprise (i) a first optimized influenza HA polypeptide comprising an amino acid sequence at least 99% or at least 99.5% identical to SEQ ID NO: 2, and (ii) a second optimized influenza HA polypeptide comprising an amino acid sequence at least 99% or 99.5% identical to SEQ ID NO: 3. In particular embodiments, the amino acid sequence of the first optimized influenza HA polypeptide that is at least 99% or at least 99.5% identical to SEQ ID NO: 2 lacks the N-terminal methionine residue. In particular embodiments, the amino acid sequence of the second optimized influenza HA polypeptide that is at least 99% or 99.5% identical to SEQ ID NO: 3 lacks the N-terminal methionine residue. In particular embodiments, the amino acid sequence of the first optimized influenza HA polypeptide is at least 99% or at least 99.5% identical to residues 2-565 of SEQ ID NO: 2. In particular embodiments, the amino acid sequence of the second optimized influenza HA polypeptide is at least 99% or 99.5% identical to residues 2-566 of SEQ ID NO: 3. In particular embodiments, the amino acid sequence of the first optimized influenza HA polypeptide comprises or consists of residues 2-565 of SEQ ID NO: 2. In particular embodiments, the amino acid sequence of the second optimized influenza HA polypeptide comprises or consists of residues 2-566 of SEQ ID NO: 3. In some embodiments, the amino acid sequences of the optimized influenza HA polypeptides in the composition are at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, or at least 99.9% identical to SEQ ID NO: 2, SEQ ID NO: 3, residues 2-565 of SEQ ID NO: 2 or residues 2-566 of SEQ ID NO: 3. In some embodiments, the amino acid sequences of the optimized influenza HA polypeptides in the composition are 100% homologous to SEQ ID NO: 2, SEQ ID NO: 3, residues 2-565 of SEQ ID NO: 2 or residues 2-566 of SEQ ID NO: 3. In some embodiments, the compositions comprise at least two different optimized influenza HA polypeptides, wherein the amino acid sequence of the polypeptides comprises no more than two, or no more than one substitution relative to SEQ ID NO: 2 or SEQ ID NO: 3.

In some embodiments, the compositions described herein comprise (i) a first optimized influenza HA polypeptide comprising an amino acid sequence at least 99% or at least 99.5% identical to SEQ ID NO: 2, and (ii) a second optimized influenza HA polypeptide comprising an amino acid sequence at least 96%, 96.5%, 97%, 97.5%, 98%, 98.5%, 99%, or 99.5% identical to SEQ ID NO: 4. In particular embodiments, the amino acid sequence of the first optimized influenza HA polypeptide that is at least 99% or at least 99.5% identical to SEQ ID NO: 2 lacks the N-terminal methionine residue. In particular embodiments, the amino acid sequence of the second optimized influenza HA polypeptide that is at least 96%, 96.5%, 97%, 97.5%, 98%, 98.5%, 99%, or 99.5% identical to SEQ ID NO: 4 lacks the N-terminal methionine residue. In particular embodiments, the amino acid sequence of the first optimized influenza HA polypeptide is at least 99% or at least 99.5% identical to residues 2-565 of SEQ ID NO: 2. In particular embodiments, the amino acid sequence of the second optimized influenza HA polypeptide is at least 99% or 99.5% identical to residues 2-566 of SEQ ID NO: 4. In particular embodiments, the amino acid sequence of the first optimized influenza HA polypeptide comprises or consists of residues 2-565 of SEQ ID NO: 2. In particular embodiments, the amino acid sequence of the second optimized influenza HA polypeptide comprises or consists of residues 2-566 of SEQ ID NO: 4. In some embodiments, the amino acid sequences of the optimized influenza HA polypeptides in the composition are at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, or at least 99.9% identical to SEQ ID NO: 2, SEQ ID NO: 4, residues 2-565 of SEQ ID NO: 2 or residues 2-566 of SEQ ID NO: 4. In some embodiments, the amino acid sequences of the optimized influenza HA polypeptides in the composition are 100% homologous to SEQ ID NO: 2, SEQ ID NO: 4, residues 2-565 of SEQ ID NO: 2 or residues 2-566 of SEQ ID NO: 4. In some embodiments, the compositions comprise at least two different optimized influenza HA polypeptides, wherein the amino acid sequence of the polypeptides comprises no more than two, or no more than one substitution relative to SEQ ID NO: 2 or SEQ ID NO: 4.

In some embodiments, the compositions described herein comprise (i) a first optimized influenza HA polypeptide comprising an amino acid sequence at least 99% or 99.5% identical to SEQ ID NO: 3, and (ii) a second optimized influenza HA polypeptide comprising an amino acid sequence at least 96%, 96.5%, 97%, 97.5%, 98%, 98.5%, 99%, or 99.5% identical to SEQ ID NO: 4. In particular embodiments, the amino acid sequence of the first optimized influenza HA polypeptide that is at least 99% or 99.5% identical to SEQ ID NO: 3 lacks the N-terminal methionine residue. In particular embodiments, the amino acid sequence of the second optimized influenza HA polypeptide that is at least 96%, 96.5%, 97%, 97.5%, 98%, 98.5%, 99%, or 99.5% identical to SEQ ID NO: 4 lacks the N-terminal methionine residue. In particular embodiments, the amino acid sequence of the first optimized influenza HA polypeptide is at least 99% or 99.5% identical to residues 2-566 of SEQ ID NO: 3. In particular embodiments, the amino acid sequence of the second optimized influenza HA polypeptide is at least 99% or 99.5% identical to residues 2-566 of SEQ ID NO: 4. In particular embodiments, the amino acid sequence of the first optimized influenza HA polypeptide comprises or consists of residues 2-566 of SEQ ID NO: 3. In particular embodiments, the amino acid sequence of the second optimized influenza HA polypeptide comprises or consists of residues 2-566 of SEQ ID NO: 4. In some embodiments, the amino acid sequences of the optimized influenza HA polypeptides in the composition are at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, or at least 99.9% identical to SEQ ID NO: 3, SEQ ID NO: 4, residues 2-566 of SEQ ID NO: 3 or residues 2-566 of SEQ ID NO: 4. In some embodiments, the amino acid sequences of the optimized influenza HA polypeptides in the composition are 100% homologous to SEQ ID NO: 3, SEQ ID NO: 4, residues 2-566 of SEQ ID NO: 3 or residues 2-566 of SEQ ID NO: 4. In some embodiments, the compositions comprise at least two different optimized influenza HA polypeptides, wherein the amino acid sequence of the polypeptides comprises no more than two, or no more than one substitution relative to SEQ ID NO: 3 or SEQ ID NO: 4.

The optimized HA polypeptides may be expressed/produced in diverse eukaryotic-based expression systems, including microalgae (e.g. *Schizochytrium* sp.; see, e.g., Bayne, A-C.V. et al., *PLOS ONE,* 8(4):e61790, April 2013), plant-based systems (e.g., tobacco plants; see, e.g., Jul-Larsen, A., et al., *Hum Vaccin Immunother.,* 8(5):653-61, 2012), yeast (see, e.g., Athmaram, T. N. et al., *Virol J.,* 8:524, 2011), and fungi (see, e.g., Allgaier, S. et al., *Biologicals,* 37:128-32, 2009). Bacterial based expression systems are also encompassed by the present invention (see, e.g., Davis, A. R. et al., *Gene,* 21:273-284, 1983). These publications are incorporated herein by reference in their entirety.

Computationally optimized HA polypeptides of the present invention may be purified by any technique known in the art, including conventional ion exchange chromatography, hydrophobic interaction chromatography, reverse phase chromatography and/or gel filtration. Computationally optimized HA polypeptides of the present invention may also be recovered from conditioned media following secretion from eukaryotic or prokaryotic cells.

Influenza Virus-Like Particles (VLPs)

In some embodiments, the present invention provides for influenza virus-like particles (VLPs) and combinations thereof comprising one or more of the computationally optimized H1N1 influenza HA polypeptides (or immunogenic fragment thereof) as described herein (e.g., an HA polypeptide that appears in Table 1). The influenza VLPs are, in some embodiments, generally made up of HA, NA and virus structural (e.g., HIV gag) proteins. Production of influenza VLPs is known in the art and will be readily apparent to persons of skill upon reading the present disclosure. For example, influenza VLPs may be produced by transfection of host cells with plasmids encoding the HA, NA and HIV gag proteins. To give but one example, a suitable host cell includes a human cell (e.g., HEK293T). After incubation of the transfected cells for an appropriate time to allow for protein expression (such as for approximately 72 hours), VLPs may be isolated from cell culture supernatants. In some embodiments, influenza VLPs as disclosed herein may be used as influenza vaccines to elicit a broadly neutralizing immune response against H1N1 influenza viruses.

Whole Influenza Viruses

Also provided are whole recombinant influenza viruses comprising one or more of the computationally optimized recombinant HA polypeptides (or immunogenic fragment or fragments thereof) described herein. The recombinant influenza viruses can be produced by plasmid-based reverse genetics (see, e.g., Neumann, G. et la., *Reverse Genetics of Influenza Viruses, Methods Mol Biol.,* 2012, 865:193-206; incorporated by reference herein) and egg-based technologies; e.g. a recombinant virus comprising a computationally optimized H1 HA polypeptide as described herein, a wild-type NA polypeptide from an H1N1 influenza strain and a backbone of internal protein genes from a donor virus (e.g., influenza A/Puerto Rico/8/34 (PR8)) that confers a high yield in eggs. For example, six plasmids encoding the internal proteins of the high-growth influenza A/Puerto Rico/8/34 (PR8) donor virus can be co-transfected with two plasmids encoding a computationally optimized H1N1 HA polypeptide as described herein and a wild-type neuraminidase (NA) glycoprotein into qualified mammalian cells (e.g., Vero cells), followed by isolation of the recombinant virus. Recombinant viruses containing internal protein genes from the PR8 virus may be used to prepare live-attenuated and/or inactivated influenza virus vaccines (see, e.g., Fodor, E. et al. *Rescue of influenza A virus from Recombinant DNA. J. Virol.,* 1999, 73, 9679-9682; incorporated by reference herein).

It is possible to incorporate the computationally optimized H1N1 HA polypeptide as described herein into a live, attenuated influenza virus. Live, attenuated viruses can elicit a long-lasting and broad immune (humoral and cellular) response that represents a naturally occurring transient infection, particularly, in younger subjects whose immune system are not as fully developed. For example, a live attenuated influenza vaccines can be produced using NA genes from circulating viruses and computationally optimized H1N1 HA sequences on an attenuated, temperature-sensitive, cold adapted virus backbone (e.g., a 6:2 reassortant with six internal gene segments from an attenuated donor virus such as A/Ann Arbor/6/60 that confers temperature-sensitive and cold-adapted phenotypes and is attenuated for virulence). This backbone prevents replication at temperatures above a certain temperature (e.g., 33° C.), thereby restricting replication to the upper but not lower respiratory tract. Methods of making and using such live, attenuated, temperature sensitive (aka cold adapted) influenza viruses are well known in the art. See e.g., He et al., *Molecular Basis of Live-Attenuated Influenza Virus, PloS One.,* 2013, 8(3): e60413; Sridhar et al., *Influenza Vaccination Strategies: Comparing Inactivated and Live Attenuated Influenza Vaccines,* 2015, *Vaccines,* 2015, 3(2):373-89.

Distinct recombinant influenza viruses, each comprising a different recombinant HA polypeptide disclosed herein, can be separately produced and then combined into the combinations/cocktails. The recombinant influenza virus combinations/cocktails can be used as influenza vaccines to elicit a protective immune response against H1N1 influenza viruses, including human and swine H1N1 influenza viruses; for example, they can be administered as components of a live-attenuated or split-inactivated vaccine.

Thus, in some embodiments, the present invention provides inactivated H1N1 influenza vaccines comprising combinations or cocktails of the computationally optimized H1N1 influenza HA polypeptides (or immunogenic fragments thereof) as described herein (e.g., cocktails of the HA polypeptides that appear in Table 1), wherein the vaccines comprise one of three types of antigen preparation: inactivated whole virus, sub-virions where purified virus particles are disrupted with detergents or other reagents to solubilize the lipid envelope ("split" vaccine) or purified HA polypeptide ("subunit" vaccine). In some embodiments, virus can be inactivated by treatment with formaldehyde, beta-propiolactone, ether, ether with detergent (such as TWEEN-80®), cetyl trimethyl ammonium bromide (CTAB) and Triton N101, sodium deoxycholate and tri(n-butyl) phosphate. Inactivation can occur after or prior to clarification of allantoic fluid (from virus produced in eggs); the virions are isolated and purified by centrifugation (Nicholson et al., eds., 1998, *Textbook of Influenza,* Blackwell Science, Malden, Mass.; incorporated herein by reference). To assess the potency of the vaccine, the single radial immunodiffusion (SRD) test can be used (Schild et al., 1975, *Bull. World Health Organ.,* 52:43-50 & 223-31; Mostow et al., 1975, *J. Clin. Microbiol.,* 2:531; both of which are incorporated herein by reference).

In some embodiments, influenza virus for use in vaccines is grown in eggs, for example, in embryonated hen eggs, in which case the harvested material is allantoic fluid. Alternatively or additionally, influenza virus or optimized hemagglutinin polypeptides may be produced from any method using tissue culture to grow the virus. Suitable cell substrates for growing the virus or otherwise recombinantly producing the optimized hemagglutinin polypeptides include, for example, dog kidney cells such as MDCK or cells from a clone of MDCK, MDCK-like cells, monkey kidney cells such as AGMK cells including Vero cells, cultured epithelial cells as continuous cell lines, 293T cells, BK-21 cells, CV-1 cells, or any other mammalian cell type suitable for the production of influenza virus (including upper airway epithelial cells) for vaccine purposes, readily available from commercial sources (e.g., ATCC, Rockville, Md.). Suitable cell substrates also include human cells such as MRC-5 cells. Suitable cell substrates are not limited to cell lines; for example primary cells such as chicken embryo fibroblasts are also included.

Immunogenic Compositions

Also provided herein are immunogenic compositions (e.g., vaccines) comprising combinations or cocktails of the computationally optimized H1N1 influenza HA polypeptides (or immunogenic fragment thereof) as described herein (e.g., cocktails of the HA polypeptides that appear in Table 1), or a fusion protein or VLP or split or inactive virus comprising the optimized influenza HA proteins. In some embodiments, the compositions further comprise a pharmaceutically acceptable carrier.

In some embodiments, vaccines in accordance with the invention further comprise one or more adjuvants. For example, alum, aluminum salts (Baylor et al., 2002, *Vaccine,* 20:S18; incorporated herein by reference) and monophosphoryl lipid A (MPL; Ribi et al., 1986, *Immunology and Immunopharmacology of Bacterial Endotoxins,* Plenum Publ. Corp., NY, p. 407; incorporated herein by reference) can be used as adjuvants in human vaccines. Alternatively or additionally, new compounds are currently being tested as adjuvants in human vaccines, such as: MF59 (See, e.g., Ott et al., "MF59—*Design and Evaluation of a Safe and Potent Adjuvant for Human Vaccines" in Vaccine Design: The Subunit and Adjuvant Approach* (Powell, M. F. and Newman, M. J. eds.) Plenum Press, New York, 1995, pp. 277-296; incorporated herein by reference); CpG oligodeoxynudeotide (ODN) adjuvants such as CPG 7909 (Cooper et al., 2004, *Vaccine,* 22:3136; incorporated herein by reference); Monophosphoryl lipid A (MPL) adjuvants and lipid A mimetis including AS04 (Didierlaurent, A. M. et al, *J. Immunol.,* 2009, 183: 6186-6197; incorporated by reference herein), monophosphoryl lipid A (MPL, GSK) and glucopyranosyl lipid A GLA (Immune Design Corporation, IDC); AF03 (Klucker, M. F. et al, *J. Pharm Sci.,* 2012, 101: 4490-4500; incorporated herein by reference); the TLR-3 ligand polyinosinic:polycytidylic acid [poly(I:C)]; TLR9 adjuvants such as IC31 (Riedl, K. et al., *Vaccine,* 2008, 26: 3461-3468; incorporated herein by reference); imidazoquinolines (double cyclic organic molecules that act as TLR-7/8 agonists) such as imiquimod (R837) or resiquimod (R848); saponins such as QS21 (Ghochikyan et al., 2006, *Vaccine,* 24:2275; incorporated herein by reference), ISCOMATRIX adjuvant (Duewell, P., et al., *J. Immunol,* 2011, 187: 55-63; incorporated herein by reference), and Matrix-M™ (Novavax).

Additionally, some adjuvants are known in the art to enhance the immunogenicity of influenza vaccines, such as poly[di(carboxylatophenoxy)phosphazene] (PCCP; Payne et al., 1998, *Vaccine,* 16:92; incorporated herein by reference), interferon-γ (Cao et al., 1992, *Vaccine,* 10:238; incorporated herein by reference), block copolymer P1205 (CRL1005; Katz et al., 2000, *Vaccine,* 18:2177; incorporated herein by reference), interleukin-2 (IL-2; Mbwuike et al., 1990, *Vaccine,* 8:347; incorporated herein by reference), and polymethyl methacrylate (PMMA; Kreuter et al., 1981, *J. Pharm. Sci.,* 70:367; incorporated herein by reference).

In general, the immunogenic compositions will include one or more inactive agents such as a sterile, biocompatible carrier including, but not limited to, sterile water, saline, buffered saline, or dextrose solution. Alternatively or additionally, the composition can contain any of a variety of additives, such as stabilizers, buffers, excipients (e.g., sugars, amino acids, etc.), or preservatives. Pharmaceutically acceptable carriers used in particular embodiments include, but are not limited to, saline, buffered saline, dextrose, water, glycerol, ethanol, and combinations thereof. In some embodiments, the carrier and composition are sterile, and the formulation suits the mode of administration. In some embodiments, an immunogenic composition contains minor amounts of wetting or emulsifying agents, or pH buffering agents. In some embodiments, a pharmaceutical composition is a liquid solution, suspension, emulsion, tablet, pill, capsule, sustained release formulation, or powder. Oral formulations can include standard carriers such as pharmaceutical grades of mannitol, lactose, starch, magnesium stearate, sodium saccharine, cellulose, and magnesium carbonate. Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used with the compositions and methods provided herein are normal saline and sesame oil.

In some embodiments, an immunogenic composition is formulated for intradermal injection, intranasal administration or intramuscular injection. In some embodiments, injectables are prepared in conventional forms, either as liquid solutions or suspensions, solid forms suitable for solution or suspension in liquid prior to injection, or as emulsions. In some embodiments, injection solutions and suspensions are prepared from sterile powders, granules, and. General considerations in the formulation and manufacture of pharmaceutical agents for administration by these routes may be found, for example, in *Remington's Pharmaceutical Sciences,* 19$^{th}$ ed., Mack Publishing Co., Easton, Pa., 1995; incorporated herein by reference. At present the oral or nasal spray or aerosol route (e.g., by inhalation) are most commonly used to deliver therapeutic agents directly to the lungs and respiratory system. In some embodiments, compositions in accordance with the invention are administered using a device that delivers a metered dosage of composition (e.g., of an optimized HA polypeptide). Suitable devices for use in delivering intradermal pharmaceutical compositions described herein include short needle devices such as those described in U.S. Pat. Nos. 4,886,499, 5,190,521, 5,328,483, 5,527,288, 4,270,537, 5,015,235, 5,141,496, 5,417,662 (all of which are incorporated herein by reference).

Intradermal compositions may also be administered by devices which limit the effective penetration length of a needle into the skin, such as those described in WO1999/34850, incorporated herein by reference, and functional equivalents thereof. Also suitable are jet injection devices which deliver liquid vaccines to the dermis via a liquid jet injector or via a needle which pierces the stratum corneum and produces a jet which reaches the dermis. Jet injection devices are described for example in U.S. Pat. Nos. 5,480,381, 5,599,302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556, 4,790,824, 4,941,880, 4,940,460, WO1997/37705, and WO1997/13537 (all of which are incorporated herein by reference). Also suitable are ballistic powder/particle delivery devices which use compressed gas to accelerate vaccine in powder form through the outer layers of the skin to the dermis. Additionally, conventional syringes may be used in the classical mantoux method of intradermal administration.

Preparations for parenteral administration include sterile aqueous or nonaqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Co-Administration of Optimized H1N1 Influenza HA Polypeptides to Elicit an Immune Response Further provided are the use and methods of co-administration (e.g., immunogenic cocktail compositions or prime-boost regimens) described herein in the prophylactic or therapeutic treatment of H1N1 influenza infection; e.g., methods of generating or eliciting an immune response to influenza virus in a subject by co-administering optimized H1N1 influenza HA polypeptides, VLPs containing the optimized H1N1 influenza HA polypeptides, fusion protein, inactivated influenza virus (e.g., split-inactivated), or live attenuated influenza virus (e.g., temperature sensitive virus) as disclosed herein (e.g., cocktails of the HA polypeptides that appear in Table 1). In certain embodiments, the optimized H1N1 influenza HA polypeptides are co-administered to the subject as a combination or cocktail (i.e., at the same time). In other embodiments, the optimized H1N1 influenza HA polypeptides are co-administered sequentially either as individual polypeptides or as cocktails. For example, certain methods of eliciting an immune response in a subject comprise administering to the subject a first priming vaccine comprising a first optimized H1N1 influenza HA polypeptide as described herein followed by administering a second boosting vaccine comprising a second optimized H1N1 influenza HA polypeptide as described herein, where the second optimized H1N1 influenza HA polypeptide is different than the first optimized H1N1 influenza HA polypeptide. In some embodiments, the first priming vaccine comprises a live, attenuated virus (e.g., temperature sensitive virus) containing the first optimized H1N1 influenza HA polypeptide and the second boosting vaccine comprises the second optimized H1N1 influenza HA polypeptide, for example, a VLP containing the second optimized H1N1 influenza HA polypeptide.

In some embodiments, the HA protein, HA fusion protein, VLP or virus can be administered using any suitable route of administration, such as, for example, intramuscular, intranasal or oral. In some embodiments, the HA protein, fusion protein, VLP or virus is administered as a composition further comprising a pharmaceutically acceptable carrier and/or an adjuvant.

The uses and methods of the compositions described herein can include selecting a subject (e.g., a human subject) in need of treatment. Compositions comprising the optimized influenza HA polypeptides may be administered prior to or after development of one or more symptoms of an H1N1 influenza infection. Administration can be systemic or local. That is, in some embodiments, the compositions described herein may be administered prophylactically to prevent H1N1 influenza infection or ameliorate the symptoms of a potential H1N1 influenza infection. In some embodiments, a subject is at risk of H1N1 influenza virus infection if the subject will be in contact with other individuals or livestock (e.g., swine) known or suspected to have been infected with pandemic influenza virus and/or if the subject will be present in a location in which H1N1 influenza infection is known or thought to be prevalent or endemic. In some embodiments, the compositions are administered to a subject considered to be suffering from an H1N1 influenza infection, or the subject is displaying one or more symptoms commonly associated with influenza infection. In some embodiments, the subject is known or believed to have been exposed to the H1N1 influenza virus. In some embodiments, a subject is considered to be at risk or susceptible to an H1N1 influenza infection if the subject is known or believed to have been exposed to the influenza virus. In some embodiments, a subject is known or believed to have been exposed to the H1N1 influenza virus if the subject has been in contact with other individuals or livestock (e.g., swine) known or suspected to have been infected with pandemic influenza virus and/or if the subject is or has been present in a location in which H1N1 influenza infection is known or thought to be prevalent or endemic.

Immunogenic compositions in accordance with the invention may be administered in any dose appropriate to achieve a desired outcome. In some embodiments, the desired outcome is induction of a lasting adaptive immune response against a broad spectrum of H1N1 influenza strains, including both seasonal and pandemic strains. In some embodiments, the desired outcome is reduction in intensity, severity, and/or frequency, and/or delay of onset of one or more symptoms of influenza infection. The dose required may vary from subject to subject depending on the species, age, weight and general condition of the subject, the severity of the infection being treated, the particular composition being used and its mode of administration.

In some embodiments of the methods of eliciting an immune response or immunizing a subject, the subject is administered a composition comprising about 15 to about 45 µg of two or three of the optimized H1N1 influenza HA polypeptide as described herein (e.g., 15-45 µg each of the HA polypeptides that appear in Table 1). In particular examples, the subject is administered a composition comprising about 15 µg, about 20 µg, about 25 µg, about 30 µg, about 35 µg, about 40 µg, or about 45 µg of each of the optimized H1N1 influenza HA polypeptides in a given cocktail. For example, if a vaccine comprises a H1N1 influenza A HA antigen cocktail consisting of two of the HA polypeptides in Table 1, a subject may receive a total amount of 30-90 µg (15-45 µg for each of the two) of influenza A HA. In one specific non-limiting example, the subject is administered about 15 µg of each of the optimized H1N1 influenza HA polypeptides. In particular examples, the subject is administered a composition comprising a total hemagglutinin antigen component of about 45 to about 90 µg. Dosages may be measured by, for example, single radial immunodiffusion (SRD) (J. M. Wood, et al.: *An improved single radial immunodiffusion technique for the assay of influenza haemagglutinin antigen: adaptation for potency determination of inactivated whole virus and subunit vaccines, J. Biol. Stand.*, 1977, 5:237-247; J. M. Wood, et al., *International collaborative study of single radial diffusion and immunoelectrophoresis techniques for the assay of haemagglutinin antigen of influenza virus, J. Biol. Stand.*, 1981, 9:317-330).

In some embodiments, the present invention provides for the immunogenic compositions (e.g., vaccines) described herein to be administered to a human subject. In particular embodiments, a human subject is 6 months of age or older, is 6 months through 35 months of age, is 36 months through 8 years of age, or 9 years of age or older.

In some embodiments, immunogenic compositions in accordance with the invention are administered in single or multiple doses. In some embodiments, pharmaceutical compositions in accordance with the invention are administered in multiple doses administered on different days (e.g., prime-boost vaccination strategies). In some embodiments, pharmaceutical compositions in accordance with the invention are administered according to a continuous dosing regimen, such that the subject does not undergo periods of less than therapeutic dosing interposed between periods of therapeutic dosing. In some embodiments, pharmaceutical compositions in accordance with the invention are administered according to an intermittent dosing regimen, such that the subject undergoes at least one period of less than therapeutic dosing interposed between two periods of therapeutic dosing.

The methods and uses of the immunogenic compositions described herein include prime-boost vaccination strategies. Prime-boost vaccination comprises administering a priming vaccine and then, after a period of time has passed, administering to the subject a boosting vaccine. The immune response is "primed" upon administration of the priming vaccine, and is "boosted" upon administration of the boosting vaccine. The priming vaccine can include any of the immunogenic HA polypeptides, and/or compositions or cocktails thereof described herein. Likewise, the boosting vaccine can include any of the immunogenic HA polypeptides, and/or compositions or cocktails thereof described herein.

For example, the priming vaccine may comprise a combination of recombinant H1N1 influenza hemagglutinin (HA) polypeptides, wherein the combination comprises a first recombinant, optimized H1N1 influenza HA polypeptide comprising an amino acid sequence at least 98%, 98.5%, 99% or 99.5% identical to SEQ ID NO: 1 and a second recombinant, optimized H1N1 influenza HA polypeptide comprising an amino acid sequence selected from the group consisting of: 1) an amino acid sequence at least 99% or 99.5% identical to SEQ ID NO: 2, 2) an amino acid sequence at least 99% or 99.5% identical to SEQ ID NO: 3, and 3) an amino acid sequence at least 96%, 96.5%, 97%, 97.5%, 98%, 98.5%, 99%, or 99.5% identical to SEQ ID NO: 4. In certain embodiments, the priming vaccine comprises or consists of a first recombinant, optimized H1N1 influenza HA polypeptide comprising the amino acid sequence of SEQ ID NO: 1 and a second recombinant, optimized H1N1 influenza HA polypeptide comprising an amino acid sequence selected from the group consisting of: the amino acid sequence of SEQ ID NO: 2, SEQ ID NO: 3, and SEQ ID NO: 4. In some embodiments, the boosting vaccine comprises or consists of the same optimized H1N1 influenza HA polypeptide as the priming vaccine. In some embodiments, the priming vaccine comprises an adjuvant. In some embodiments, the boosting vaccine comprises an adjuvant.

In some embodiments, the priming vaccine comprises a combination of recombinant H1N1 influenza HA polypeptides, wherein the combination comprises a first recombinant, optimized H1N1 influenza HA polypeptide comprising an amino acid sequence at least 98%, 98.5%, 99%, or 99.5% identical to residues 2-566 of SEQ ID NO: 1 and a second recombinant, optimized H1N1 influenza HA polypeptide comprising an amino acid sequence selected from the group consisting of: 1) an amino acid sequence at least 99% or at least 99.5% identical to residues 2-565 of SEQ ID NO: 2; 2) an amino acid sequence at least 99% or at least 99.5% identical to residues 2-566 of SEQ ID NO: 3; and 3) an amino acid sequence at least 96%, 96.5%, 97%, 97.5%, 98%, 98.5%, 99%, or 99.5% identical to residues 2-566 of SEQ ID NO: 4. In certain embodiments, the priming vaccine comprises or consists of a first recombinant, optimized H1N1 influenza HA polypeptide comprising residues 2-566 of SEQ ID NO: 1 and a second recombinant, optimized H1N1 influenza HA polypeptide comprising an amino acid sequence selected from the group consisting of: 1) residues 2-565 of SEQ ID NO: 2; 2) residues 2-566 of SEQ ID NO: 3; and 3) residues 2-566 of SEQ ID NO: 4. The boosting vaccine may be the same as the priming vaccine or may contain a different cocktail of H1N1 influenza HA polypeptides as described herein. For example, in some embodiments the boosting vaccine comprises or consists of the same combination of optimized H1N1 influenza HA polypeptides as the priming vaccine. Various prime-boost cocktail combinations of embodiments of the invention are summarized in the table below:

| Same Cocktails in Prime/Boost | |
| --- | --- |
| Prime | Boost |
| X1/P1 | X1/P1 |
| X3/P1 | X3/P1 |
| X6/P1 | X6/P1 |

| Different Cocktails in Prime/Boost | |
| --- | --- |
| Prime | Boost |
| X1/P1 | X3/P1 |
| X1/P1 | X6/P1 |
| X3/P1 | X1/P1 |
| X6/P1 | X1/P1 |
| X3/P1 | X6/P1 |
| X6/P1 | X3/P1 |

In some embodiments, the priming vaccine cocktail comprises an adjuvant. In some embodiments, the boosting vaccine cocktail comprises an adjuvant.

Alternatively, the priming vaccine and boosting vaccine can each include a different optimized H1N1 influenza HA polypeptide as described herein. In certain embodiments, the priming vaccine can include a pandemic H1N1 optimized influenza HA protein described herein and the boosting vaccine can include a seasonal H1N1 optimized influenza HA protein described herein. For example, the priming vaccine may comprise a recombinant, optimized H1N1 influenza HA polypeptide comprising an amino acid sequence at least 98%, 98.5%, 99%, or 99.5% identical to SEQ ID NO: 1. The boosting vaccine may comprise a recombinant, optimized H1N1 influenza HA polypeptide comprising an amino acid sequence selected from the group consisting of: 1) an amino acid sequence at least 99% or 99.5% identical to SEQ ID NO: 2, 2) an amino acid sequence at least 99% or 99.5% identical to SEQ ID NO: 3, and 3) an amino acid sequence at least 96%, 96.5%, 97%, 97.5%, 98%, 98.5%, 99%, or 99.5% identical to SEQ ID NO: 4. In certain embodiments, the priming vaccine comprises or consists of a first recombinant, optimized H1N1 influenza HA polypeptide comprising the amino acid sequence of SEQ ID NO: 1 and the boosting vaccine comprises or consists of a second recombinant, optimized H1N1 influenza HA polypeptide comprising an amino acid sequence selected from the group consisting of: the amino acid sequence of SEQ ID NO: 2, SEQ ID NO: 3, and SEQ ID NO: 4.

In other embodiments, the priming vaccine may comprise a recombinant, optimized H1N1 influenza HA polypeptide comprising an amino acid sequence at least 98%, 98.5%, 99%, or 99.5% identical to residues 2-566 of SEQ ID NO: 1. The boosting vaccine may comprise a recombinant, optimized H1N1 influenza HA polypeptide comprising an amino acid sequence selected from the group consisting of: 1) an amino acid sequence at least 99% or 99.5% identical to residues 2-565 of SEQ ID NO: 2, 2) an amino acid sequence at least 99% or 99.5% identical to residues 2-566 of SEQ ID NO: 3, and 3) an amino acid sequence at least 96%, 96.5%, 97%, 97.5%, 98%, 98.5%, 99%, or 99.5% identical to residues 2-566 of SEQ ID NO: 4. In certain embodiments, the priming vaccine comprises or consists of a first recombinant, optimized H1N1 influenza HA polypeptide comprising residues 2-566 of SEQ ID NO: 1 and the boosting vaccine comprises or consists of a second recombinant, optimized H1N1 influenza HA polypeptide comprising an amino acid sequence selected from the group consisting of: 1) residues 2-565 of SEQ ID NO: 2, 2) residues 2-566 of SEQ ID NO: 3, and 3) residues 2-566 of SEQ ID NO: 4.

In some embodiments, the methods of eliciting an immune response or immunizing in a subject comprise:
administering a priming vaccine comprising a first recombinant, optimized H1N1 influenza HA polypeptide comprising an amino acid sequence at least 98%, 98.5%, 99%, or 99.5% identical to SEQ ID NO: 1; and administering a boosting vaccine comprising a second recombinant, optimizedH1N1 influenza HA polypeptide comprising an amino acid sequence at least 99% or 99.5% identical to SEQ ID NO: 2. In certain embodiments, the first recombinant, optimized H1N1 influenza HA polypeptide comprises an amino acid sequence at least 98%, 98.5%, 99%, or 99.5% identical to residues 2-566 of SEQ ID NO: 1 and the second recombinant, optimized H1N1 influenza HA polypeptide comprises an amino acid sequence at least 99% or 99.5% identical to residues 2-565 of SEQ ID NO: 2. In other embodiments, the first recombinant, optimized H1N1 influenza HA polypeptide comprises the amino acid sequence of SEQ ID NO: 1 or residues 2-566 of SEQ ID NO: 1 and the second recombinant, optimized H1N1 influenza HA polypeptide comprises the amino acid sequence of SEQ ID NO: 2 or residues 2-565 of SEQ ID NO: 2.

In some embodiments the methods of eliciting an immune response or immunizing in a subject comprise:

administering a priming vaccine comprising a first recombinant, optimized H1N1 influenza HA polypeptide comprising an amino acid sequence at least 98%, 98.5%, 99%, or 99.5% identical to SEQ ID NO: 1; and administering a boosting vaccine comprising a second recombinant, optimized H1N1 influenza HA polypeptide comprising an amino acid sequence at least 99% or 99.5% identical to SEQ ID NO: 3. In certain embodiments, the first recombinant, optimized H1N1 influenza HA polypeptide comprises an amino acid sequence at least 98%, 98.5%, 99%, or 99.5% identical to residues 2-566 of SEQ ID NO: 1 and the second recombinant, optimized H1N1 influenza HA polypeptide comprises an amino acid sequence at least 99% or 99.5% identical to residues 2-566 of SEQ ID NO: 3. In other embodiments, the first recombinant, optimized H1N1 influenza HA polypeptide comprises the amino acid sequence of SEQ ID NO: 1 or residues 2-566 of SEQ ID NO: 1 and the second recombinant, optimized H1N1 influenza HA polypeptide comprises the amino acid sequence of SEQ ID NO: 3 or residues 2-566 of SEQ ID NO: 3.

In some embodiments the methods of eliciting an immune response or immunizing in a subject comprise:

administering a priming vaccine comprising a first recombinant, optimized H1N1 influenza HA polypeptide comprising an amino acid sequence at least 98%, 98.5%, 99%, or 99.5% identical SEQ ID NO: 1; and administering a boosting vaccine comprising a second recombinant, optimized H1N1 influenza HA polypeptide comprising an amino acid sequence at least at least 96%, 96.5%, 97%, 97.5%, 98%, 98.5%, 99%, or 99.5% identical to SEQ ID NO: 4. In certain embodiments, the first recombinant, optimized H1N1 influenza HA polypeptide comprises an amino acid sequence at least 98%, 98.5%, 99%, or 99.5% identical to residues 2-566 of SEQ ID NO: 1 and the second recombinant, optimized H1N1 influenza HA polypeptide comprises an amino acid sequence at least 99% or 99.5% identical to residues 2-566 of SEQ ID NO: 4. In other embodiments, the first recombinant H1N1, optimized influenza HA polypeptide comprises the amino acid sequence of SEQ ID NO: 1 or residues 2-566 of SEQ ID NO: 1 and the second recombinant, optimized H1N1 influenza HA polypeptide comprises the amino acid sequence of SEQ ID NO: 4 or residues 2-566 of SEQ ID NO: 4.

In other embodiments, the order of administering the priming vaccine and boosting vaccine set forth above can be reversed. Thus, in certain embodiments, the priming vaccine may comprise a recombinant, optimized H1N1 influenza HA polypeptide comprising an amino acid sequence selected from the group consisting of: 1) an amino acid sequence at least 99% or 99.5% identical to SEQ ID NO: 2, 2) an amino acid sequence at least 99% or 99.5% identical to SEQ ID NO: 3, and 3) an amino acid sequence at least 96%, 96.5%, 97%, 97.5%, 98%, 98.5%, 99%, or 99.5% identical to SEQ ID NO: 4; and the boosting vaccine may comprise a recombinant, optimizedH1N1 influenza HA polypeptide comprising an amino acid sequence at least 98%, 98.5%, 99%, or 99.5% identical SEQ ID NO: 1. In certain embodiments, the priming vaccine comprises or consists of a first recombinant, optimized H1N1 influenza HA polypeptide comprising an amino acid sequence selected from the group consisting of: the amino acid sequence of SEQ ID NO: 2, SEQ ID NO: 3, and SEQ ID NO: 4; and the boosting vaccine comprises or consists of a second recombinant, optimized H1N1 influenza HA polypeptide comprising the amino acid sequence of SEQ ID NO: 1.

In other embodiments, the priming vaccine may comprise a recombinant, optimized H1N1 influenza HA polypeptide selected from the group consisting of: 1) an amino acid sequence at least 99% or 99.5% identical to residues 2-565 of SEQ ID NO: 2, 2) an amino acid sequence at least 99% or 99.5% identical to residues 2-566 of SEQ ID NO: 3, and 3) an amino acid sequence at least 96%, 96.5%, 97%, 97.5%, 98%, 98.5%, 99%, or 99.5% identical to residues 2-566 of SEQ ID NO: 4. The boosting vaccine may comprise a recombinant, optimized H1N1 influenza HA polypeptide comprising an amino acid sequence at least 98%, 98.5%, 99%, or 99.5% identical to residues 2-566 of SEQ ID NO: 1. In certain embodiments, the priming vaccine comprises or consists of a first recombinant, optimized H1N1 influenza HA polypeptide comprising an amino acid sequence selected from the group consisting of: 1) residues 2-565 of SEQ ID NO: 2, 2) residues 2-566 of SEQ ID NO: 3, and 3) residues 2-566 of SEQ ID NO: 4 and the boosting vaccine comprises or consists of a second recombinant, optimized H1N1 influenza HA polypeptide comprising residues 2-566 of SEQ ID NO: 1.

In some embodiments the methods of eliciting an immune response or immunizing in a subject comprise:

administering a priming vaccine comprising a first recombinant, optimized H1N1 influenza HA polypeptide comprising an amino acid sequence at least 99% or 99.5% identical to SEQ ID NO: 2; and administering a boosting vaccine comprising a second recombinant, optimizedH1N1 influenza HA polypeptide comprising an amino acid sequence at least 98%, 98.5%, 99%, or 99.5% identical to SEQ ID NO: 1. In certain embodiments, the first recombinant, optimizedH1N1 influenza HA polypeptide comprises an amino acid sequence at least 99% or 99.5% identical to residues 2-565 of SEQ ID NO: 2 and the second recombinant, optimized H1N1 influenza HA polypeptide comprises an amino acid sequence at least 98%, 98.5%, 99%, or 99.5% identical to residues 2-566 of SEQ ID NO: 1. In other embodiments, the first recombinant, optimized H1N1 influenza HA polypeptide comprises the amino acid sequence of SEQ ID NO: 2 or residues 2-565 of SEQ ID NO: 2 and the second recombinant, optimized H1N1 influenza HA polypeptide comprises the amino acid sequence of SEQ ID NO: 1 or residues 2-566 of SEQ ID NO: 1.

In some embodiments the methods of eliciting an immune response or immunizing in a subject comprise:

administering a priming vaccine comprising a first recombinant, optimized H1N1 influenza HA polypeptide comprising an amino acid sequence at least 99% or 99.5% identical to SEQ ID NO: 3; and administering a boosting vaccine comprising a second recombinant, optimized H1N1 influenza HA polypeptide comprising an amino acid sequence at least 98%, 98.5%, 99%, or 99.5% identical to SEQ ID NO: 1. In certain embodiments, the first recombinant, optimized H1N1 influenza HA polypeptide comprises an amino acid sequence at least 99% or 99.5% identical to residues 2-566 of SEQ ID NO: 3 and the second recombinant, optimized H1N1 influenza HA polypeptide comprises an amino acid sequence at least 98%, 98.5%, 99%, or 99.5% identical to residues 2-566 of SEQ ID NO: 1. In other embodiments, the first recombinant, optimized H1N1 influenza HA polypeptide comprises the amino acid sequence of SEQ ID NO: 3 or residues 2-566 of SEQ ID NO: 3 and the second recombinant, optimized H1N1 influenza HA polypeptide comprises the amino acid sequence of SEQ ID NO: 1 or residues 2-566 of SEQ ID NO: 1.

In some embodiments the methods of eliciting an immune response or immunizing in a subject comprise:

administering a priming vaccine comprising a first recombinant, optimized H1N1 influenza HA polypeptide comprising an amino acid sequence at least 99% or 99.5% identical to SEQ ID NO: 3; and administering a boosting vaccine comprising a second recombinant, optimized H1N1 influenza HA polypeptide comprising an amino acid sequence at least 99% or 99.5% identical to SEQ ID NO: 2. In certain embodiments, the first recombinant, optimized H1N1 influenza HA polypeptide comprises an amino acid sequence at least 99% or 99.5% identical to residues 2-566 of SEQ ID NO: 3 and the second recombinant, optimized H1N1 influenza HA polypeptide comprises an amino acid sequence at least 99% or 99.5% identical to residues 2-565 of SEQ ID NO: 2. In other embodiments, the first recombinant, optimized H1N1 influenza HA polypeptide comprises the amino acid sequence of SEQ ID NO: 3 or residues 2-566 of SEQ ID NO: 3, and the second recombinant, optimized H1N1 influenza HA polypeptide comprises the amino acid sequence of SEQ ID NO: 2 or residues 2-565 of SEQ ID NO: 2.

The booster vaccine is administered to the subject after the primer vaccine. Administration of the priming vaccine and the boosting vaccine can be separated by any suitable timeframe. For example, the booster vaccine can be administered 1 week, 2 weeks, 3 weeks, 4 weeks, 5 weeks, or 6 weeks, or a range defined by any two of the foregoing values, following administration of the priming vaccine. The dose of the priming vaccine and boosting vaccine administered to a subject depends on a number of factors, including the extent of any side-effects, the particular route of administration, and the like. In certain embodiments, the dose of the priming vaccine comprises about 15-45 µg (e.g., about 15, 20, 25, 30, 35, 40, or 45 µg) of the recombinant H1N1 influenza HA polypeptide. In certain embodiments, the dose of the boosting vaccine comprises about 15-45 µg (e.g., about 15, 20, 25, 30, 35, 40, or 45 µg) of the recombinant H1N1 influenza HA polypeptide. In some embodiments, the dose of the boosting vaccine is the same as the dose of the priming vaccine.

Immunogenic compositions of the present invention may be administered either alone or in combination with one or more other therapeutic agents including, but not limited to, other vaccines and/or antibodies. By "in combination with," it is not intended to imply that the agents must be administered at the same time or formulated for delivery together, although these methods of delivery are within the purview of the present invention. In general, each agent will be administered at a dose and on a time schedule determined for that agent. In some embodiments, pharmaceutical compositions in accordance with the invention and/or optimized HA polypeptides as described herein are administered in combination with one or more of an anti-viral agent (e.g., Oseltamivir [TAMIFLU®], Zanamavir [RELEZA®], etc.) and/or a sialidase.

In some embodiments, co-administration (e.g., immunogenic cocktail compositions or prime-boost regimens) elicit a protective immune response against at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 different H1N1 influenza strains. In particular embodiments, "eliciting a protective immune response" can be ascertained, for example, by using the generally known hemagglutination inhibition assay (HAI) as a surrogate measure of influenza vaccine efficacy. HAI assays may use chicken, turkey or horse erythrocytes for the detection of antibodies specific for H1N1. In particular embodiments, protective immune responses are demonstrated by eliciting an average HAI titer of greater than 1:40, which has been correlated with prevention and reduction of influenza illness. In some embodiments, the immunogenic compositions described herein elicit an HAI antibody titer of at least 1:30, 1:40, 1:50, 1:60, or within a range of 1:30-1:60 or 1:40-1:60, when administered to a subject for prophylaxis or treatment of influenza infection. HAI antibody titers of approximately 1:32 to 1:40 will generally protect about 50% of subjects from infection after immunization with inactivated human influenza virus vaccine. When converting log 2 data, a value slightly less than 5.5 corresponds to an HAI antibody titer of 1:40. However, serum HAI antibody titers as low as 1:8 have been shown to provide resistance to infection with human influenza viruses, which indicates that the levels of antibody required for protection may be fairly low (Treanor, J. & Wright, P. F. *Immune correlates of protection against influenza in the human challenge model. Dev. Biol. (Basel)*, 2003, 115:97-104; incorporated by reference herein).

In some embodiments, elicitation of a protective immune response can by identified by seroconversion rates. In particular embodiments, a protective level of seroconversion is defined as at least a 4-fold rise in HAI titer, for example, a pre-administration or vaccination HAI titer of less than 1:10 and a post vaccinate titer of greater than or equal to 1:40. In other words, successful rates of seroconversion may be defined as the percentage of subjects with either a pre-vaccination HAI titer less than about 1:10 and a post-vaccination HAI titer of greater than about 1:40 or a pre-vaccination HAI titer greater than about 1:10 and a minimum four-fold rise in post-vaccination HAI antibody titer. In particular embodiments, the immunogenic compositions described herein elicit a seroconversion rate of at least a 3-fold 4-fold, at least a 5-fold, at least a 6-fold, etc. rise in HAI titer when administered to a subject for prophylaxis or treatment of influenza infection. In particular embodiments, the immunogenic compositions improve seroconversion (measured by HAI) by at least 30%, at least 40%, at least 50%, at least 60%, at least 70%, at least 80% or at least 90% when administered to a subject for prophylaxis or treatment of influenza infection. In some embodiments, co-administration (e.g., immunogenic cocktail compositions or prime-boost regimens) generates a protective immune response that spans at least 5, at least 6, at least 7, at least 8, at least 9, at least 10 or at least 11 (e.g., 11) different strains of H1N1 influenza.

Animal Testing

The present invention provides methods for testing optimized HA polypeptides in accordance with the invention in an animal host. As used herein, an "animal host" includes any animal model suitable for influenza research. For example, animal hosts suitable for the invention can be any mammalian hosts, including primates, ferrets, cats, dogs, cows, horses, rodents such as, mice, hamsters, guinea pigs, rabbits, and rats. In some embodiments, an animal host used for the invention is a ferret. In particular, in some embodiments, an animal host is naïve to viral exposure or infection prior to administration of a binding agent in accordance with the invention (optionally in a composition in accordance with the invention). In some embodiments, the animal host is inoculated with, infected with, or otherwise exposed to influenza virus prior to or concurrent with co-administration (e.g., immunogenic cocktail compositions or prime-boost regimens) of the optimized H1N1 HA polypeptides described herein. An animal host used in the practice of the present invention can be inoculated with, infected with, or otherwise exposed to virus by any method known in the art. In some embodiments, an animal host may be inoculated with, infected with, or exposed to virus intranasally.

Naïve and/or inoculated animals may be used for any of a variety of studies. For example, such animal models may be used for virus transmission studies as in known in the art. It is contemplated that the use of ferrets in virus transmission studies may serve as a reliable predictor for virus transmission in humans. For example, air transmission of viral influenza from inoculated animals (e.g., ferrets) to naïve animals is known in the art (Tumpey et al., 2007, Science 315; 655-59; incorporated herein by reference). Virus transmission studies may be used to test computationally optimized HA polypeptides in accordance with the invention. For example, cocktails of computationally optimized HA polypeptides described herein or prime-boost regimens of different, individual COBRAs may be administered to a suitable animal host in order to determine the efficacy of said cocktails or prime-boost regimens in eliciting a broad immune response in the animal host. Using information gathered from studies in an animal host, one may predict the efficacy of said cocktails or prime-boost regimens to elicit broadly protective in a human host.

The present invention will be more fully understood by reference to the following Examples. All literature citations are incorporated by reference.

EXAMPLES

Example 1—Material and Methods

Design and Phylogenic Analyis of H1N1 COBRA has.

The design and characterization of the computationally optimized broadly reactive antigen (COBRA) has been described previously (see, e.g., US2014/0147459, WO2013/148164, and WO2012/036993; incorporated herein by reference). HA sequences were designed based upon different antigenic eras of H1N1 both chronologically, as well as by species each influenza virus was isolated. These designs took into account the evolution of H1N1 influenza viruses isolated in humans over about a 100 year span of time. Viruses isolated represent different antigenic eras of H1N1 HA sequences that result in a higher diversity of sequence variation. The COBRA design utilized these chronologically different eras of H1N1 HA sequences to account for the unique antigenic types of HA domains. The sequences used in the methodology included HA sequences isolated from humans between 1918-2012, 1978-2008 and 1999-2012, as well as swine HA sequences from viruses isolated from 1933-1998.

Primary consensus sequences specific were then aligned and the most common amino acid was chosen resulting in secondary consensus sequences. For each round of consensus generation, multiple alignment analysis was applied and the consensus sequence was generated using AlignX (Vector NTI). The final amino acid sequence, termed computationally optimized broadly reactive antigen (COBRA), was reverse translated and optimized for expression in mammalian cells, including codon usage and RNA optimization (GeneArt; Regensburg, Germany). Final consensus sequences are referred to by one of 4 H1N1 COBRA HA designations in Table. 1. X1 (SEQ ID NO: 4) encompassed HA sequences that represented about the last 100 years of H1N1 history (Table 1). X3 (SEQ ID NO: 3) does not contain pandemic H1N1 HA sequences, but X6 (SEQ ID NO: 2) does contain sequences representing the post-2009 pandemic H1N1 era. P1 (SEQ ID NO: 1) represents a unique set of H1N1 HA sequences isolated from both human and swine species. Phylogenetic analysis of the COBRA HA proteins indicated that each molecule clustered with different representative wild-type vaccine strains (data not shown). The P1 COBRA HA located on the tree with the swine-like viruses (CA/09, NJ/76, and SC/1918), and the X1 COBRA clustered with historical H1N1 viruses. The X3 and X6 H1N1 COBRA HA proteins clustered with modern seasonal HA proteins. Furthermore, a BLAST search using each of the COBRA HA sequences revealed that each sequence was a unique sequence that has not been isolated from the environment (data not shown).

In Vitro Expression.

H1N1 COBRA HA constructs were synthesized and inserted into a pTR600 expression vector. Human embryonic kidney (HEK) 293T cells ($1 \times 10^6$) were transiently transfected with 3 μg DNA expressing each COBRA or wild-type HA gene cassette. Cells were incubated for 72 h at 37° C. and then lysed with 1% Triton-X 100 and clarified supernatant harvested following centrifugation. Cell lysates were then electrophoresed on a 10% SDS-PAGE gel and transferred to a PVDF membrane. The blot was probed with pooled mouse antisera from infections with viruses expressing HA derived from H1N1. HA-antibody complexes were then detected using goat anti-mouse IgG HRP (Southern Biotech; Birmingham, Ala., USA). HRP activity was detected using chemiluminescent substrate (Pierce Biotechnology; Rockford Ill., USA) and exposed to X-ray film (ThermoFisher; Pittsburgh, Pa., USA).

Functional Characterization.

To determine receptor-binding characteristics, virus-like particles (VLPs) containing COBRA HA proteins were purified from the supernatants of mammalian cell lines as previously described. HEK 293T cells were transiently transfected with plasmids expressing HIV Gag, COBRA HA and neuraminidase (NA, A/Thailand/1(KAN-1)/2004) and incubated for 72 h at 37° C. Supernatants were collected and VLPs were purified via ultracentrifugation (100,000×g through 20% glycerol, weight per volume) for 4 h at 4° C. The pellets were subsequently resuspended in phosphate buffered saline PBS, pH 7.2 and stored at −80° C. until use. Protein concentration was determined by Micro BCA™ Protein Assay Reagent Kit (Pierce Biotechnology, Rockford, Ill., USA). COBRA HA VLPs were prepared in various amounts as measured by total HA protein and each individual preparation was two-fold serially diluted in v-bottom microtiter plates. An equal volume of 1% horse erythrocytes (RBC) (Lampire; Pipersville, Pa., USA) in PBS was added to the diluted VLPs and incubated for 60 minutes at room temperature. The HA titer was determined by the reciprocal dilution of the last well which contained agglutinated RBC.

Vaccine Preparation.

HEK 293T cells were transiently transfected with plasmids expressing M1 (A/Puerto Rico/8/1934, optimized for expression in mammalian cells), NA (A/Thailand/1(KAN-1)/2004, optimized for expression in mammalian cells) and COBRA HA or HA from wild-type H1N1 strains and incubated for 72 h at 37° C. (Medigen Inc, Rockville, Md., USA). Supernatants were collected and cell debris removed by low speed centrifugation followed by vacuum filtration through a 0.22 µm sterile filter. VLPs were purified via ultracentrifugation (100,000×g through 20% glycerol, weight per volume) for 4 h at 4° C. The pellets were subsequently resuspended in PBS pH 7.2 and stored in single use aliquots at −80° C. until use. Total protein concentration was determined by Micro BCA™ Protein Assay Reagent Kit (Pierce Biotechnology, Rockford, Ill., USA).

HA specific content was determined by western blot and densitometry. Purified recombinant COBRA HA and purified VLPs were prepared in standard total protein amounts and were electrophoresed on a 10% SDS-PAGE gel and transferred to a PVDF membrane. The blot was probed with mouse polyclonal antisera and the HA-antibody complexes were detected using a goat anti-mouse IgG conjugated to horse radish peroxidase (HRP) (Southern Biotech; Birmingham, Ala., USA). HRP was detected by chemiluminescent substrate (Pierce Biotechnology; Rockford Ill., USA) and exposed to X-ray film (ThermoFisher; Pittsburgh, Pa., USA). Density of bands was determined using Image) software (NIH). Density of recombinant HA bands were used to calculate a standard curve and the density of the purified VLPs was interpolated using the results from the recombinant HA. Monovalent inactivated influenza, split virus vaccines (Sanofi-Pasteur, Swiftwater, Pa., USA) representing A/New Caledonia/20/1999, A/Brisbane/59/2007, or A/California/07/2009 H1N1 viruses. Experiments were performed in triplicate and multiple exposure times were analyzed for all iterations.

Mouse Studies.

BALB/c mice (Mus musculis, females, 6-8 weeks) were purchased from Jackson Laboratories, (Bar Harbor, Me., USA) and housed in microisolator units and allowed free access to food and water and were cared for under USDA guidelines for laboratory animals. Mice (16 mice per group) were vaccinated with purified VLPs (3.0 µg) based upon HA content from the densitometry assay or they were vaccinated with the monovalent inactivated split influenza vaccine (IIV), via intramuscular injection at week 0 and then boosted with a different vaccine at the same dose at weeks 4 and 8. In addition, some mice were administered a cocktail of H1N1 COBRA VLP vaccines (1.5 µg dose of each of the two vaccines). Vaccines at each dose were formulated with either with AFO3 or Imject® alum adjuvant (Pierce Biotechnology; Rockford, Ill., USA) according to the manufacturer's protocol or phosphate buffered saline alone as a mock vaccination. Twenty-eight days after each vaccination, blood was collected from anesthetized mice via the retro-orbital plexus and transferred to a microfuge tube. Tubes were centrifuged and serum samples were removed and frozen at −20±5° C.

Four weeks after final vaccination, mice were challenged intranasally with $5\times10^6$ plaque forming units (PFU) of the A/California/07/2009 (H1N1) in a volume of 50 µl. After infection, mice were monitored daily for weight loss, disease signs and death for 14 days after infection. At days 2 and 3 post-infection, 5 mice were sacrificed per time point for determination of viral lung titers. Individual body weights and death were recorded for each group on each day after inoculation. Experimental endpoint was defined as greater than 20% weight loss. All procedures were in accordance with the NRC Guide for the Care and Use of Laboratory Animals, the Animal Welfare Act, and the CDC/NIH Biosafety in Microbiological and Biomedical Laboratories.

ELISA assay. The ELISA assay was used to assess total antibody titer and IgG isotype titer to the HA. High binding, 96-well polystyrene plates (Costar; Lowell, Mass., USA) were coated overnight with 50 ng/well of recombinant HA. Coating antigens were derived from the following representative viral isolates: A/California/07/2009 (H1N1). Plates were blocked with 5% milk diluted in PBS with 0.05% Tween 20 (blocking buffer). Serum samples were diluted in blocking buffer and added to plates. Serum was two-fold serially diluted and allowed to incubate for 1 hour at room temperature. Plates were washed and HRP-conjugated polyclonal goat anti-murine IgG were diluted in blocking buffer and added to plates. Plates were incubated for 1 h at room temperature, washed and HRP activity detected with TMB substrate (Sigma-Aldrich; St. Louis, Mo., USA). Plates were incubated in the dark for 15 minutes and then the reaction was stopped with $2N\ H_2SO_4$. Optical densities at a wavelength of 450 nm (OD450) were read by a spectrophotometer (BioTek; Winooski, Vt., USA) and end point dilution titers were determined. End point titers were determined as the reciprocal dilution of the last well, which had an OD450 above the mean OD450 plus two standard deviations of naïve animal sera.

Hemagglutination Inhibition (HAI) Assay.

The HAI assay was used to assess functional antibodies to the HA able to inhibit agglutination of horse erythrocytes. The protocol was adapted from the CDC laboratory-based influenza surveillance manual. To inactivate non-specific inhibitors, sera were treated with receptor destroying enzyme (RDE; Denka Seiken, Co., Japan) prior to being tested. Briefly, three parts RDE was added to one part sera and incubated overnight at 37° C. RDE was inactivated by incubation at 56° C. for about 30 min. RDE treated sera was two-fold serially diluted in v-bottom microtiter plates. An equal volume of each H1N1 virus, adjusted to approximately 8 HAU/50 µl, was added to each well. The plates were covered and incubated at room temperature for 20 min followed by the addition of 1% chicken erythrocytes (RBC) (Lampire Biologicals, Pipersville, Pa., USA) in PBS. Red blood cells were stored at 4° C. and used within 72 h of preparation. The plates were mixed by agitation, covered, and the RBCs were allowed to settle for 1 h at room temperature. The HAI titer was determined by the reciprocal dilution of the last well that contained non-agglutinated RBC. Positive and negative serum controls were included for each plate. All mice were negative (HAI less than or equal to 1:10) for pre-existing antibodies to currently circulating human influenza viruses prior to vaccination.

Plaque Assay.

Madin-Darby Canine Kidney (MDCK) cells were plated ($5\times10^5$) in each well of a 6-well plate. Samples were diluted (final dilution factors of $10^0$ to $10^{-6}$) and overlayed onto the cells in 100 µl of DMEM supplemented with penicillin-streptomycin and incubated for 1 hr. Samples were removed, cells were washed twice and media was replaced with 2 ml of L15 medium plus 0.8% agarose (Cambrex; East Rutherford, N.J., USA) and incubated for 72 h at 37° C. with 5% CO2. Agarose was removed and discarded. Cells were fixed with 10% buffered formalin, and then stained with 1% crystal violet for 15 min. Following thorough washing in dH2O to remove excess crystal violet, plates were allowed to dry, plaques counted, and the plaque forming units (PFU)/ml were calculated.

Statistical Analysis.

Statistical significance of the antibody data was determined using a two-way analysis of variance (ANOVA) with Bonferroni's post-test to analyze differences between each vaccine group for the different test antigens (multiparametric). Differences in weight loss, sickness score, and viral titers were analyzed by two-way ANOVA, followed by Bonferroni's post-test for each vaccine group at multiple time points. Significance was defined as $p<0.05$. Statistical analyses were done using GraphPad Prism® software.

Example 2—Binding of Monoclonal Antibodies to the Influenza HA Head and Stalk Domains Each trimerized COBRA or wild-type HA proteins were purified from 293T cells and used to test the binding of 4 previously characterized monoclonal antibodies. The monoclonal antibody, C179, binds to a conformational region in the stalk of H1N1 HA proteins. The C179 bound all wild-type and COBRA HA proteins with varying efficiencies. In contrast, the three HA head-specific monoclonal antibodies bound to some, but not all, COBRA and wild-type HA proteins. The CH65 monoclonal antibody bound to the HA from A/New Caledonia/20/1999 (NC/99), but not the HA from CA/09 or PR/34. The 5J8 and 4K8 monoclonal antibodies both bound to CA/09, but not the other two wild-type HA proteins. In contrast, the 5J8 antibody bound to each of the P1, X6, X3, and X1 COBRA antigens. The CH65 antibody bound to the P1, X6, and X3 COBRA antigens but not the X1 COBRA antigen. Monoclonal antibody 4K8 only bound to X1. Overall, the pattern of monoclonal antibody binding indicates that each of the COBRA HA proteins are exposing different epitopes and therefore different structures.

Example 3—Prime-Boost H1N1 COBRA HA VLP Vaccines Elicit Broadly Reactive Antibody Responses BALB/c mice were vaccinated with different combinations of the COBRA VLPs in a prime-boost strategy, with sera collected at day 56. Mice were vaccinated with one of 4 H1N1 COBRA VLP vaccines (X1, X3, X6, and P1) in multiple prime-boost combinations and serum samples were analyzed at week 8 post-vaccination. Mice vaccinated with prime-boost combinations of the X1 and X6 COBRA VLPs had little HAI activity against any of the 15 viruses in the panel (FIGS. 1A and D), where as mice primed with X3 and boosted with X6 had HAI activity against Sing/86, Bei/95, NC/99, and SI/06 (FIG. 1B). Other combinations elicited little or low HAI activity (FIG. 1C-F). There was little or no activity against pandemic H1N1 (2009-2013) or historical H1N1 strains (1934-1957) by any prime-boost administration that lacked P1.

Figure 1H:
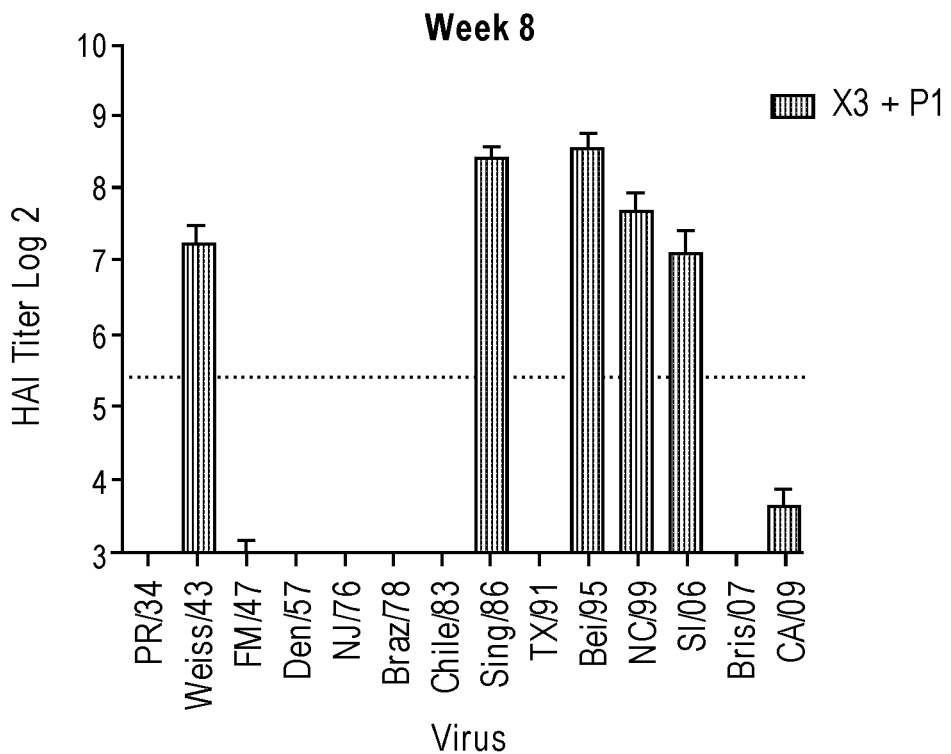

Mice vaccinated with combinations containing the P1 VLP elicited antibodies that recognized different sets of H1N1 viruses. Mice primed with P1 VLPs and then boosted with either X3 or X6 VLPs had high HAI activity against 4 seasonal (Weiss/43, Sing/86, Bie/95, NC/99) and the 1 pandemic H1N1 viruses (FIGS. 1G and I). When X3 VLPs were used to prime mice and those mice were boosted with P1, HAI activity against the same 4 seasonal viruses were detected, but there was no HAI detected against the pandemic virus (FIG. 1H). Interestingly, priming with P1 VLPs elicits higher HAI titers than boosting with P1 VLPs. Priming with P1 and boosting with X1 elicited HAI activity against the pandemic strains only (FIG. 1K) and there was no detectable HAI activity when mice were primed with X1 VLPs and boosted with any other COBRA VLP vaccine. Interestingly, mice primed with P1 and boosted with X3 VLPs had similar HAI activity as prime-boost administration of P1 and X6 VLPs. Notably P1 and X1 combinations were quite poor.

Figure 1I:
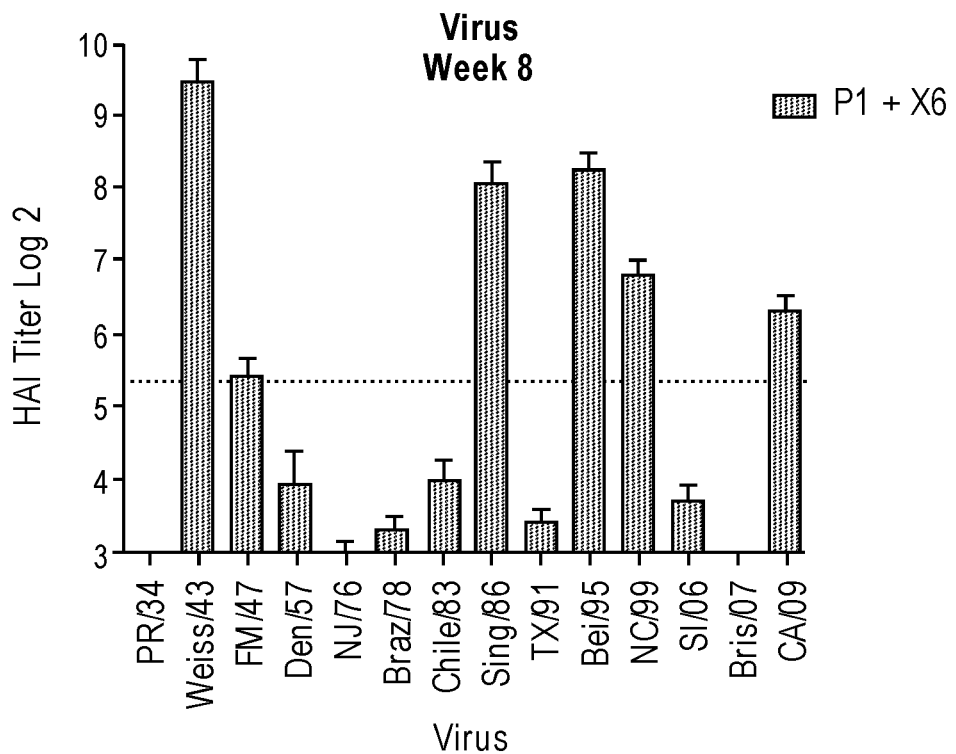
Figure 1J:
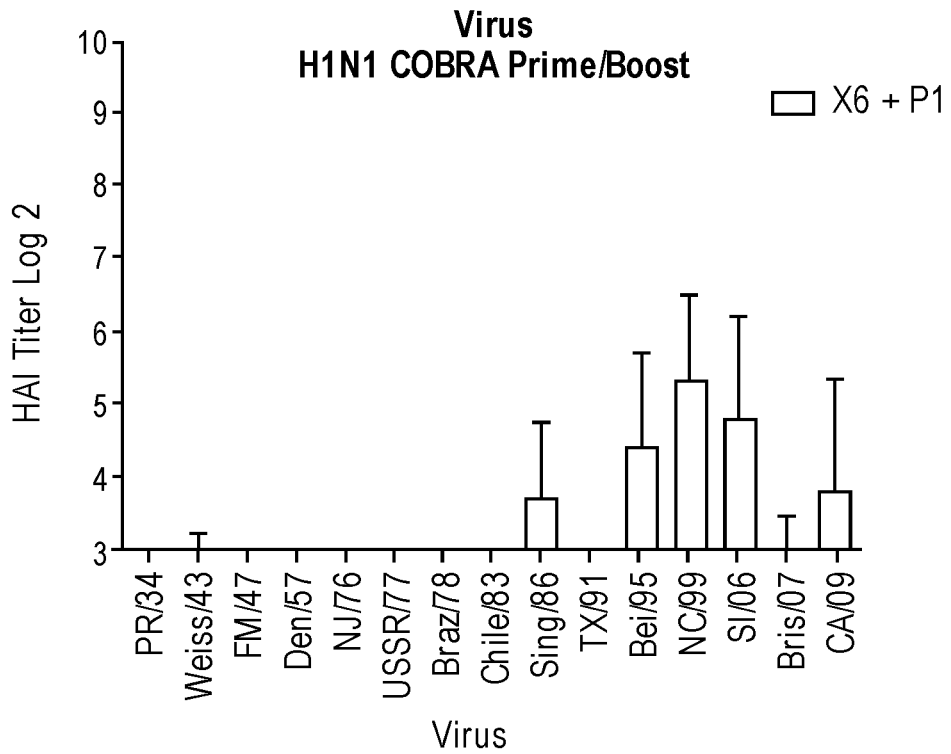
Figure 1K:
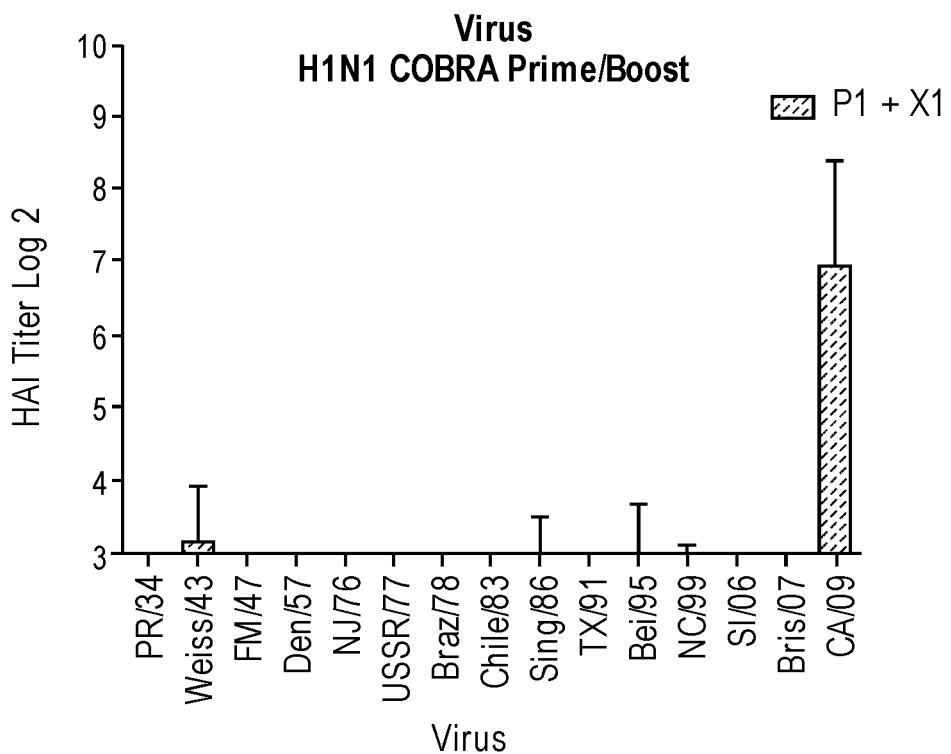
Figure 1L:
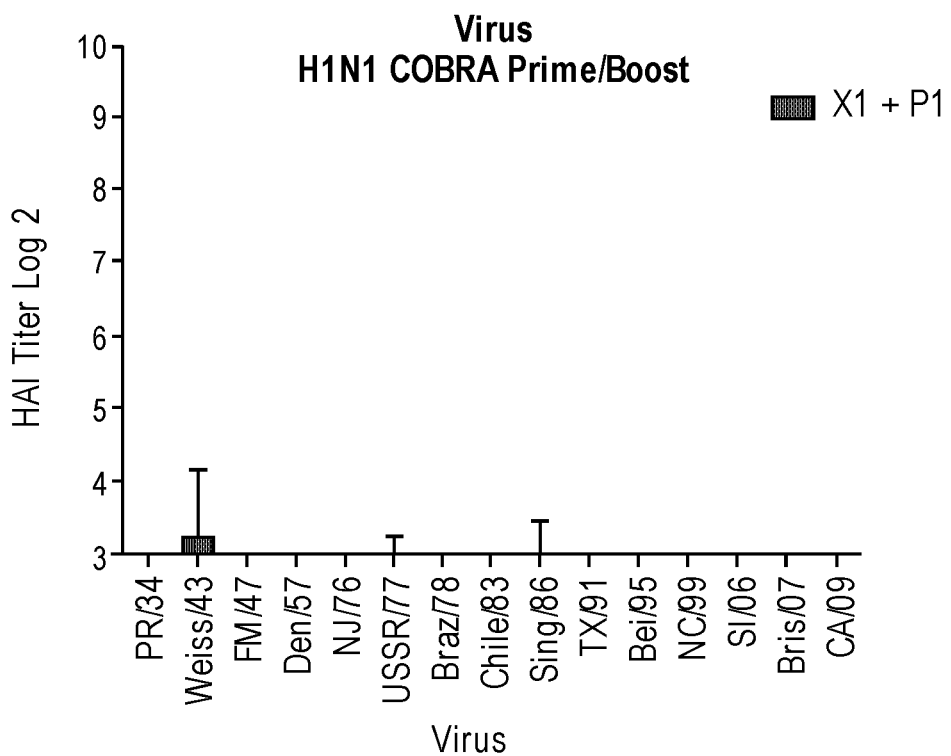

Mice vaccinated with prime-boost combinations of P1 and X6 VLPs exhibited a much broader response against H1N1 viruses, including a pandemic virus (Cal/09) and a broad temporal distribution of seasonal influenza viruses (FIGS. 1I and 1J). Although the X6 COBRA was designed using the alignment of HA sequence from 1999-2012, the co-administration of the P1 and X6 COBRAs unexpectedly showed broad HAI activity, including activity against numerous H1N1 influenza strains isolated before 1999.

Priming with P1 VLPs and boosting with X6 VLPs elicits higher HAI titers against both pandemic and seasonal strains than priming with X6 VLPs and boosting with P1 VLPs, once again highlighting the importance of the order of administering the prime-boost regimen (FIG. 1I-J). Prime-boost combinations of P1 and X3 VLPs also elicited high HAI titers against both pandemic and seasonal strains (FIG. 1G-H). Notably, priming with P1 and boosting with X3 VLPs yielded strong HAI activity against the Cal/09 strain, whereas priming with X3 and boosting with P1 VLPs yielded little to no activity against this same strain (FIG. 1G-H). Thus, while the order of administration of these H1N1 COBRAs is important, it is difficult to predict how the order will affect the breadth of response against different H1N1 influenza strains.

Figures 2A, 2B:
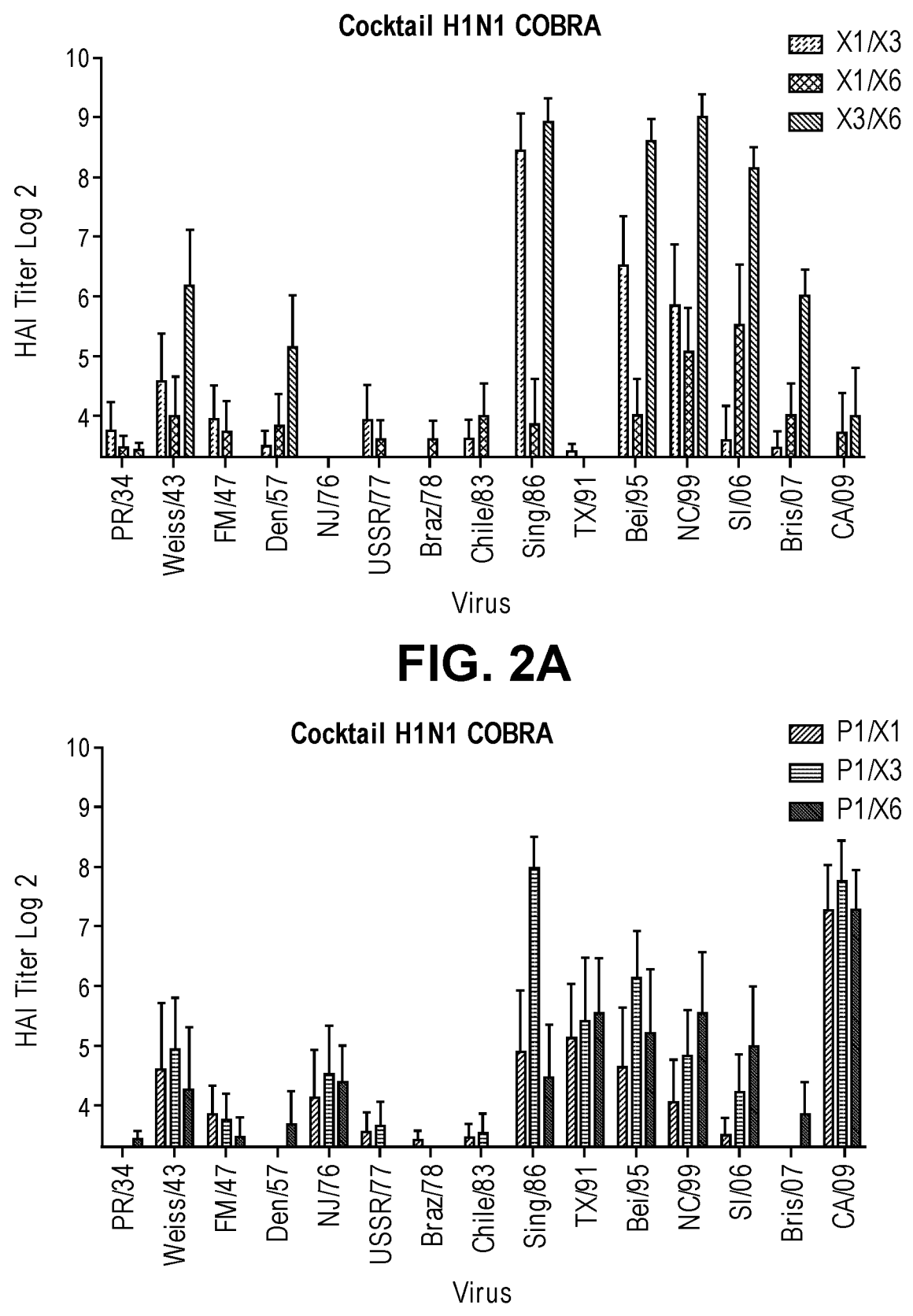

Example 4—Cocktail Mixtures of H1N1 COBRA HA VLP Vaccines Elicit Broadly Reactive HAI Activity Against Wild-Type H1N1 Strains Cocktails of COBRA HA VLP vaccines were mixed together and tested for HAI activity against a panel of 15 H1N1 isolates. Mice were vaccinated with different combinations of two H1N1 COBRA HA VLP vaccines simultaneously (1.5 µg dose of each VLP vaccine). Mice vaccinated with a cocktail of X1 and X3 VLPs had HAI activity against three viruses in the panel (Sing/86, Bei/95, and NC/99) and mice vaccinated with a cocktail of X1 and X6 VLPs only recognized NC/99 and SI/06 (FIG. 2A). However, mice vaccinated with X3 and X6 VLPs simultaneously had HAI activity against 6 seasonal H1N1 influenza viruses (FIG. 2A). The cocktail of X1 and X6 appeared to have an antagonistic effect against certain strains, particularly Sing/86 and Bei/95, highlighting the unpredictability of co-administering the H1N1 COBRA HA vaccines. When mice were vaccinated with cocktails containing the P1 VLPs, all mice had high HAI activity against CA/09 (FIG. 2B). Cocktails of P1 and X1, X3 or X6 elicited antibodies with HAI activity against viruses from 1986-2006, but little or no activity against earlier H1N1 strains or Bris/07. Surprisingly, adding the pandemic P1 COBRA to the X1, X3, or X6 COBRA expanded the breadth of protection against the seasonal H1N1 seasonal strains, particularly the NJ/76 and TX/91 strains, against which none of the X1/X3, X1/X6, or X3/X6 combinations showed any HAI activity (compare FIG. 2A with FIG. 2B). Similar results were observed with mice vaccinated with a triple cocktail of X1, X3, and P1 (FIG. 2C). Interestingly, the group of mice primed with a cocktail of P1/X3 VLP vaccines and boosted with a cocktail of P1/X6 VLP vaccines had high HAI activity against Sing/86, Bei/95, NC/99, SI/06, and CA/09 (FIG. 2D). This HAI activity pattern is similar to mice primed with X3 VLPs and boosted with P1 VLPs, with the exception of high HAI activity against CA/09 and a reduction in HAI activity against Weiss/43 (FIG. 1H).

Figure 3A:
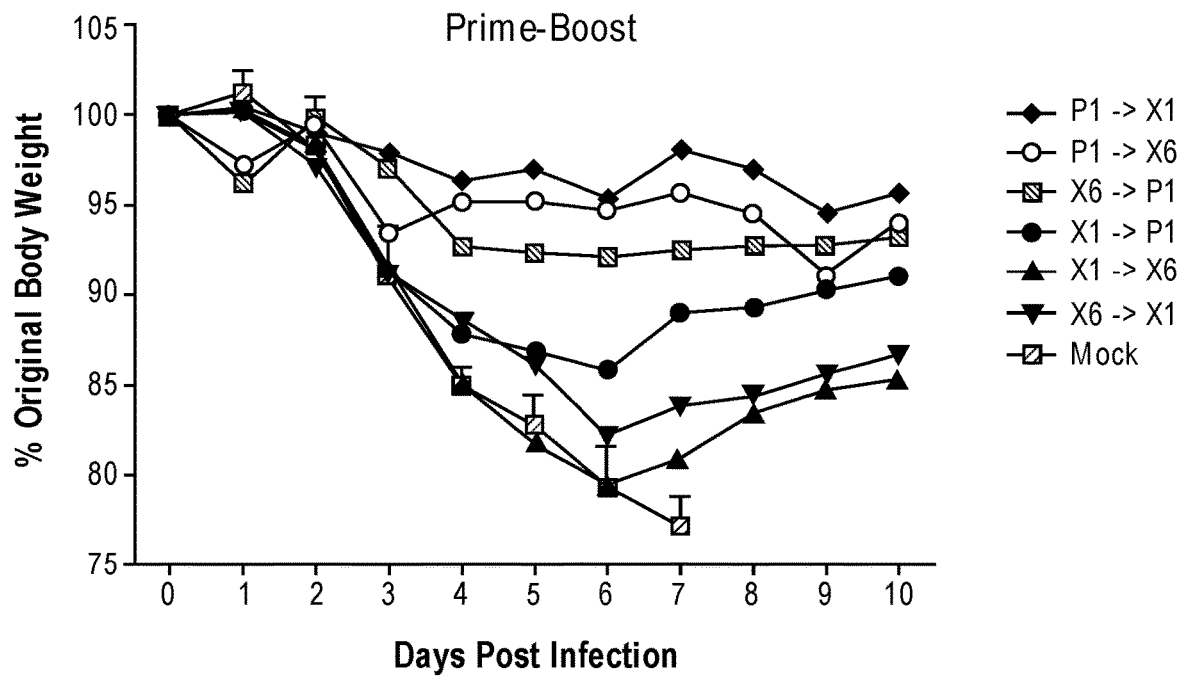
FIGS. 3A-C show the % weight loss induced by H1N1 influenza virus challenge of mice vaccinated with prime-boost regimens (A and B) or cocktails (C) of COBRA VLP vaccines. BALB/c mice (11 mice/group) vaccinated at weeks 0 and 4 with each vaccine plus adjuvant (AFO3 or Imject alum) were infected with $1 \times 10^6$ pfu of the H1N1 isolate A/California/07/2009 (CA/09). Mice were monitored daily for weight loss over a 14 day observation period. Three mice were sacrificed on day 2 and another 3 on day 3 post-infection to assess lung titers, therefore, the weights for 5 mice were recorded for the entire 14 days.
Figure 3B:
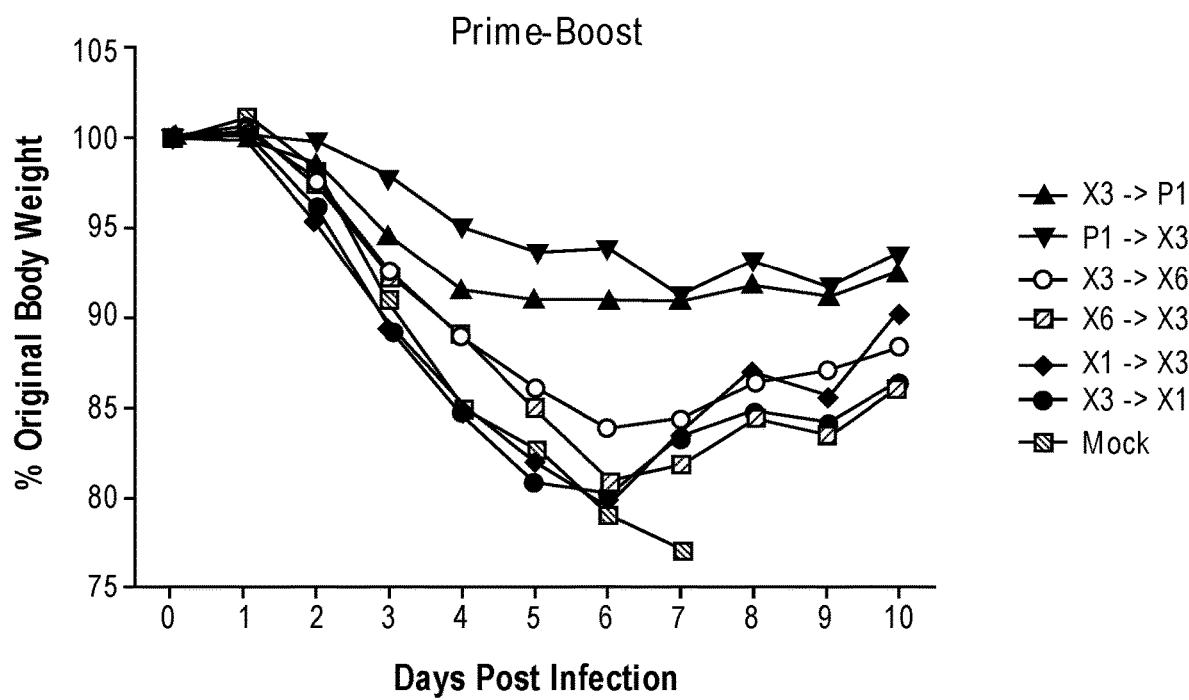

Example 5—Combination of H1N1 COBRA Vaccines Protect Mice Against Challenge with CA/09 Virus Mice were vaccinated with a prime-boost regimen of two different H1N1 COBRAs and challenged with CA/09 influenza virus ($5 \times 10^6$ PFU). Mice vaccinated with any prime-boost combination including the P1 VLP had an average weight loss of less than 7%, except for mice primed with X1 and boosted with P1, which lost 13% of their original weight by day 6 post-infection (FIGS. 3A and B). All other prime-boost vaccinated mice lost between 10-20% of body weight by days 6-7 post-infection, with some mice reaching the experimental endpoint and the other remaining mice then slowly began to recover weight. All mock-vaccinated mice lost greater than 20% body weight and all were humanely sacrificed by day 7 post-infection.

Figure 3C:
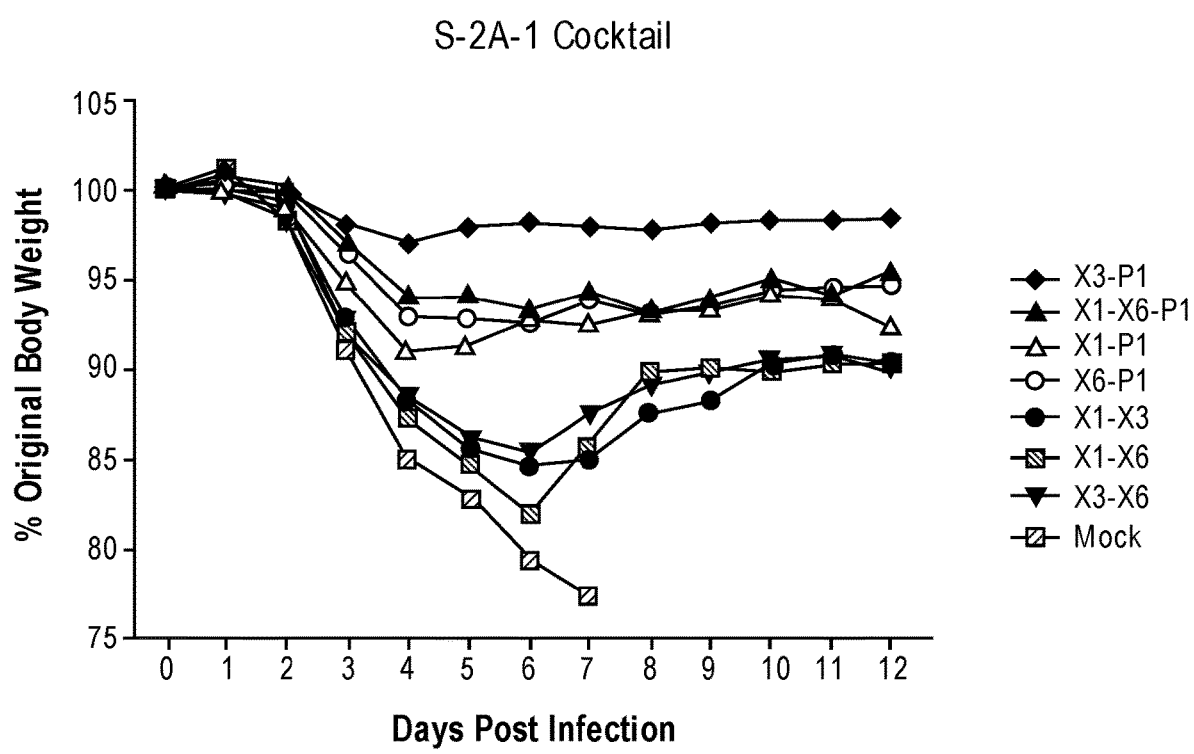

For cocktail vaccinated mice, again vaccine regimens containing P1 VLPs were better protected against CA/09 challenge than mice vaccinated with other COBRA VLP vaccine cocktails (FIG. 3C). Mice vaccinated with a cocktail of P1 and X3 VLPs had no signs of morbidity and weight loss, whereas mice vaccinated with other cocktails containing P1 VLPs lost on average 5-7% body weight. Mice vaccinated with cocktails not containing P1 VLPs lost between 15-20% body weight (FIG. 3C).

Figure 4A:
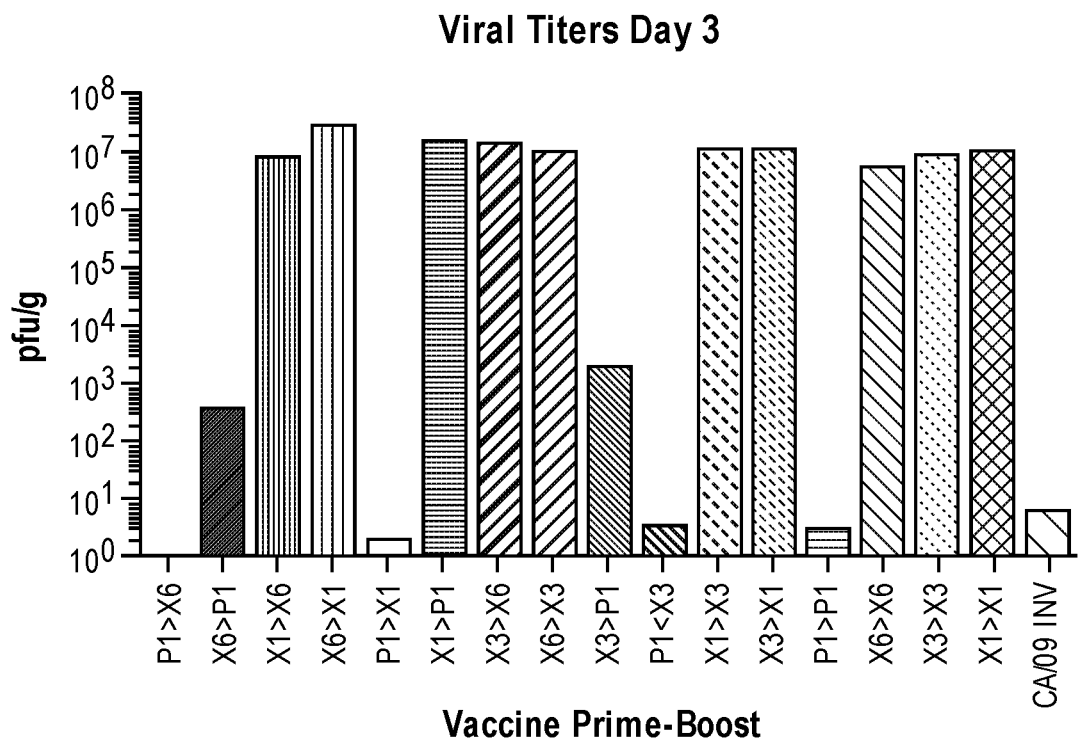
FIGS. 4A-B show viral lung titers in mice (day 3 post infection) vaccinated with COBRA VLP prime boost regimens (A) or COBRA VLP cocktails (B).
Figure 4B:
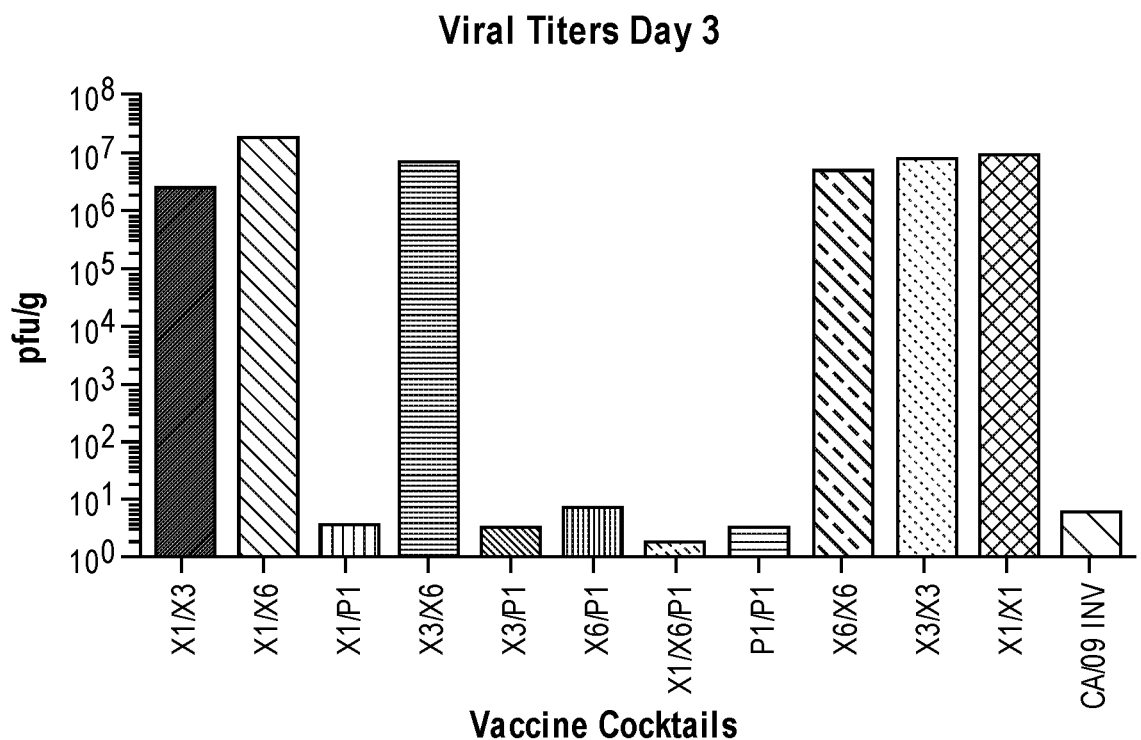

At day 3 post-infection, all mice primed with P1 VLPs had little or no detectable viral titers in their lungs (FIG. 4A), which was similar to mice vaccinated with CA/09 IIV. Mice primed with X3 or X6 COBRA VLPs and boosted with P1 VLPs had moderate viral lung titers ($10^2$-$10^3$ pfu/g of lung tissue). Mice vaccinated with any other prime-boost regimen of COBRA VLPs had viral lung titers greater than $10^6$ pfu/g, which was similar to mock vaccinated mice (FIG. 4A). In contrast, mice vaccinated with any cocktail containing P1 VLPs had virtually no detectable viral titers in their lungs (FIG. 4B). Viral lung titers were greater than $10^6$ pfu/g in mice vaccinated with any other cocktail regimen.

Example 6—Protective Effect of H1N1 COBRA Vaccines in Naïve Ferrets

Fitch ferrets (*Mustela putorius* faro, female, 6-12-months of age), influenza naive and de-scented, can be purchased from Marshall Farms (Sayre, Pa., USA). Ferrets are pair housed in stainless steel cages (Shor-line, Kansas City, Kans., USA) containing Sani-chips Laboratory Animal Bedding (P. J. Murphy Forest Products, Montville, N.J., USA). Ferrets are provided with Teklad Global Ferret Diet (Harlan Teklad, Madison, Wis., USA) and fresh water ad libitum. The COBRA HA VLPs are diluted in PBS, pH 7.2 to achieve final concentration. Ferrets are vaccinated with purified X1, X3, X6, or P1 COBRA VLPs at one of two doses (15 µg, 3 µg), based upon HA content as determined by densitometry assay, via intramuscular injection in the quadriceps muscle in a volume of 0.25 ml at week 0 and then boosted with the same dose of a different COBRA VLPs selected from X1, X3, X6, or P1 at week 3. For example, ferrets are vaccinated with the P1 COBRA VLP (15 µg or 3 µg) and then boosted with the X1, X3, or X6 COBRA VLPs (15 µg or 3 µg).

Alternatively, ferrets are vaccinated with a cocktail of two of the following X1, X3, X6, or P1 COBRA VLPs at one of two doses (7.5 µg, 1.5 µg for each VLP), based upon HA content as determined by densitometry assay, via intramuscular injection in the quadriceps muscle in a volume of 0.25 ml at week 0 and then boosted with the same dose of the same cocktail. For example, ferrets are vaccinated with a cocktail of the P1 COBRA VLP (7.5 µg or 1.5 µg) and one of the X1, X3, or X6 COBRA VLPs (7.5 µg or 1.5 µg) and then boosted with the same cocktail.

Vaccines are stored at −80° C. prior to use and formulated with alum adjuvant (Imject Alum; Pierce Biotechnology, Rockford, Ill., USA) immediately prior to use. Animals are monitored for adverse events including weight loss, temperature, decrease in activity, nasal discharge, sneezing and diarrhea weekly during the vaccination regimen. Prior to vaccination, animals are confirmed by HAI assay to be seronegative for circulating influenza A and influenza B viruses. Fourteen to twenty-one days after each vaccination, blood is collected from anesthetized ferrets via the anterior vena cava and transferred to a microfuge tube. Tubes are centrifuged and sera is removed and frozen at −80±5° C. HAI serum antibody titer for each vaccine group is determined at week 5 using representative reassortant viruses or COBRA HA VLPs.

Three weeks after final vaccination, ferrets are challenged intranasally with a highly pathogenic H1N1 virus in a volume of 1 ml. After infection, ferrets are monitored daily for weight loss, disease signs and death for 14 days after infection. Individual body weights, sickness scores, and death are recorded for each group on each day after inoculation. Nasal washes are performed by instilling 3 ml of PBS into the nares of anesthetized ferrets each day for 7 days after inoculation. Washes are collected and stored at −80° C. until use.

Example 7—Protective Effect of H1N1 COBRA Vaccines in Pre-Immune Ferrets

Fitch ferrets (*Mustela putorius* faro, female, 6-12-months of age), influenza naive and de-scented, can be purchased from Marshall Farms (Sayre, Pa., USA). Ferrets are pair housed in stainless steel cages (Shor-line, Kansas City, Kans., USA) containing Sani-chips Laboratory Animal Bedding (P. J. Murphy Forest Products, Montville, N.J., USA). Ferrets are provided with Teklad Global Ferret Diet (Harlan Teklad, Madison, Wis., USA) and fresh water ad libitum.

Ferrets are pre-infected with seasonal H1N1 influenza viruses ($1 \times 10^6$ PFU) intranasally at 12-week intervals. Animals are monitored weekly during the infection regimen for adverse events, including weight loss, temperature, loss of activity, nasal discharge, sneezing, and diarrhea. Blood is harvested from all anesthetized ferrets via the anterior vena cava subclavin vein at days 14, 28, 56, and 84 after each infection. Serum is transferred to a centrifuge tube. Tubes are centrifuged, and serum is removed and frozen at −20±5° C.

Four weeks after final preinfection, ferrets are challenged with purified X1, X3, X6, or P1 COBRA VLPs at one of two doses (15 µg, 3 µg), based upon HA content as determined by densitometry assay, via intramuscular injection in the quadriceps muscle in a volume of 0.25 ml at week 0 and then boosted with the same dose of a different COBRA VLPs selected from X1, X3, X6, or P1 at week 3. For example, ferrets are vaccinated with the P1 COBRA VLP (15 μg or 3 μg) and then boosted with the X1, X3, or X6 COBRA VLPs (15 μg or 3 μg).

Alternatively, ferrets are challenged with a cocktail of two of the following X1, X3, X6, or P1 COBRA VLPs at one of two doses (7.5 μg, 1.5 μg for each VLP), based upon HA content as determined by densitometry assay, via intramuscular injection in the quadriceps muscle in a volume of 0.25 ml at week 0 and then boosted with the same dose of the same cocktail. For example, ferrets are vaccinated with a cocktail of the P1 COBRA VLP (7.5 μg or 1.5 μg) and one of the X1, X3, or X6 COBRA VLPs (7.5 μg or 1.5 μg) and then boosted with the same cocktail.

Vaccines are stored at −80° C. prior to use and formulated with alum adjuvant (Imject Alum; Pierce Biotechnology, Rockford, Ill., USA) immediately prior to use. Animals are monitored for adverse events including weight loss, temperature, decrease in activity, nasal discharge, sneezing and diarrhea weekly during the vaccination regimen. Fourteen to twenty-one days after each vaccination, blood is collected from anesthetized ferrets via the anterior vena cava and transferred to a microfuge tube. Tubes are centrifuged and sera is removed and frozen at −80±5° C. HAI serum antibody titer for each vaccine group is determined at week 5 using representative reassortant viruses or COBRA HA VLPs.

Three weeks after final vaccination, ferrets are challenged intranasally with a highly pathogenic H1N1 virus in a volume of 1 ml. After infection, ferrets are monitored daily for weight loss, disease signs and death for 14 days after infection. Individual body weights, sickness scores, and death are recorded for each group on each day after inoculation. Nasal washes are performed by instilling 3 ml of PBS into the nares of anesthetized ferrets each day for 7 days after inoculation. Washes are collected and stored at −80° C. until use.

Example 8—Protective Effect of H1N1 COBRA Vaccines in Naive Ferrets

To evaluate the immunogenicity of H1N1 COBRAs in a heterologous prime/boost setting, naïve ferrets were infected on Day 0 with the indicated live virus (i.e., A/Singapore/6/1986, A/Brisbane/59/2007, A/California/07/09, COBRA P1 and COBRA X3). FIG. 5A-F. The COBRA P1 and COBRA X3 polypeptides were incorporated into an attenuated, high yield PR8 background to make live virus. This Day 0 infection was also called the priming infection. Infected ferrets were then immunized on days 84 and 168 with 15 μg of VLPs carrying the HA protein from A/California/2009 (CA/09) or COBRA P1 in combination with the AF03 adjuvant. CA/09 HA represents the HA included in the current H1 standard of care and was, thus, chosen to evaluate the HAI breadth elicited by these H1N1 COBRAs. 14 days after the final immunization (D182), HAI responses were evaluated against a panel of H1 viruses (i.e., SC/1918, A/Weiss/1/1943, A/FM/1/47, A/Denver/1/57, A New Jersey/8/76, A/USSR/90/77, A/Brazil/1/78, A/Chile/1/83, A/Singapore/06/86, A/Texas/36/91, A/Beijing/262/95, A/New Caledonia/20/99, A/Solomon Islands/6/06, A/Brisbane/59/07, A/California/07/09, and A/Philadelphia/1/13), and the $Log_2$ transformed HAI titers were plotted. The dotted line indicates a titer of 1:40, which correlates with a seroprotective titer against infection with the indicated strain. FIG. 5A-F.

In the absence of the priming infection (FIG. 5A), there was very limited immunogenicity induced by the VLPs, even after 2 doses. Following a priming infection (FIG. 5B-F), the COBRA P1 consistently induced higher seroprotective titers and against a greater number of viral strains than CA/09 HA. Among the non-COBRA viruses used as the priming infection, Singapore/6/1986 yielded the broadest response following immunization (FIG. 5B), but CA/09 induced a seroprotective response against only 7/16 strains tested. In contrast, COBRA P1 induced a seroprotective titer against 14 of 16 viruses tested, and trended towards a higher magnitude HAI response as compared to that induced by CA/09 for all strains tested.

Figure 5A:
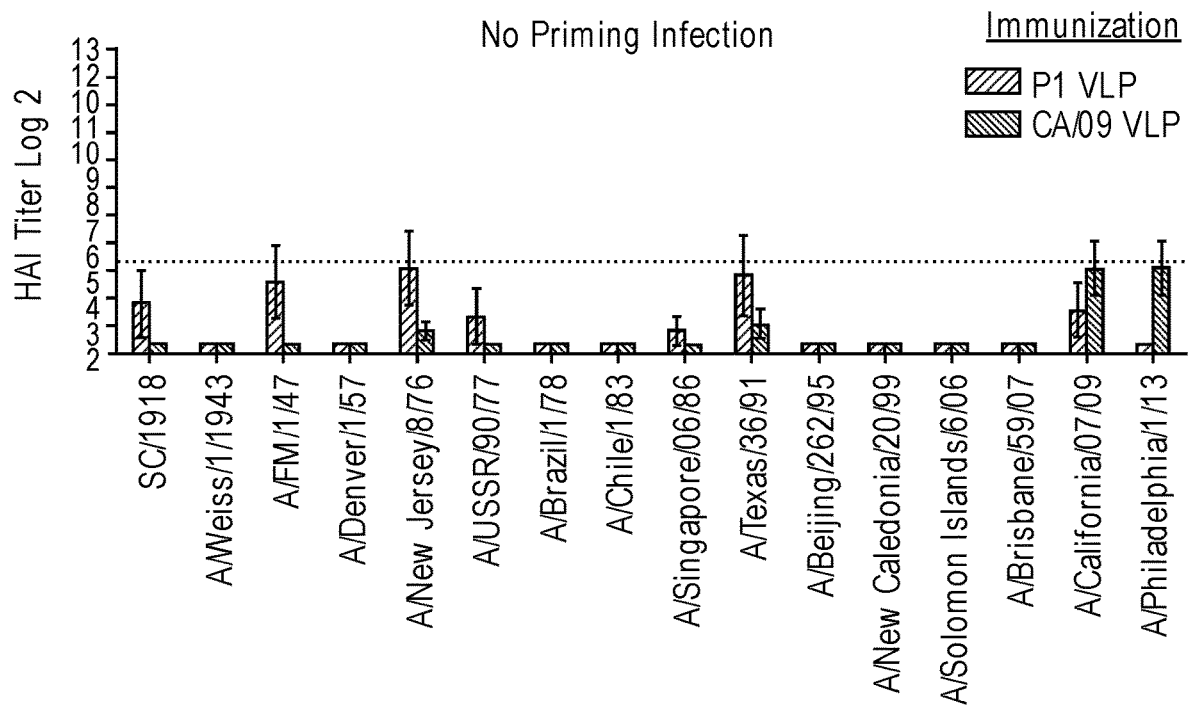
FIGS. 5A-F show viral lung titers in naive ferrets vaccinated with the following primer boost regimens: no priming infection and P1 VLP or CA09 VLP boost (A); A/Singapore6/1986 priming infection and P1 VLP or CA09 VLP boost (B); A/Brisbane/59/2007 priming infection and P1 VLP or CA09 VLP boost (C); A/California/07/09 priming infection and P1 VLP or CA09 VLP boost (D); COBRA P1 priming infection and P1 VLP or CA09 VLP boost (E); COBRA X3 priming infection and P1 VLP or CA09 VLP boost (F). HAI titers were evaluated against the panel of H1 viruses listed on the X axis.
Figure 5B:
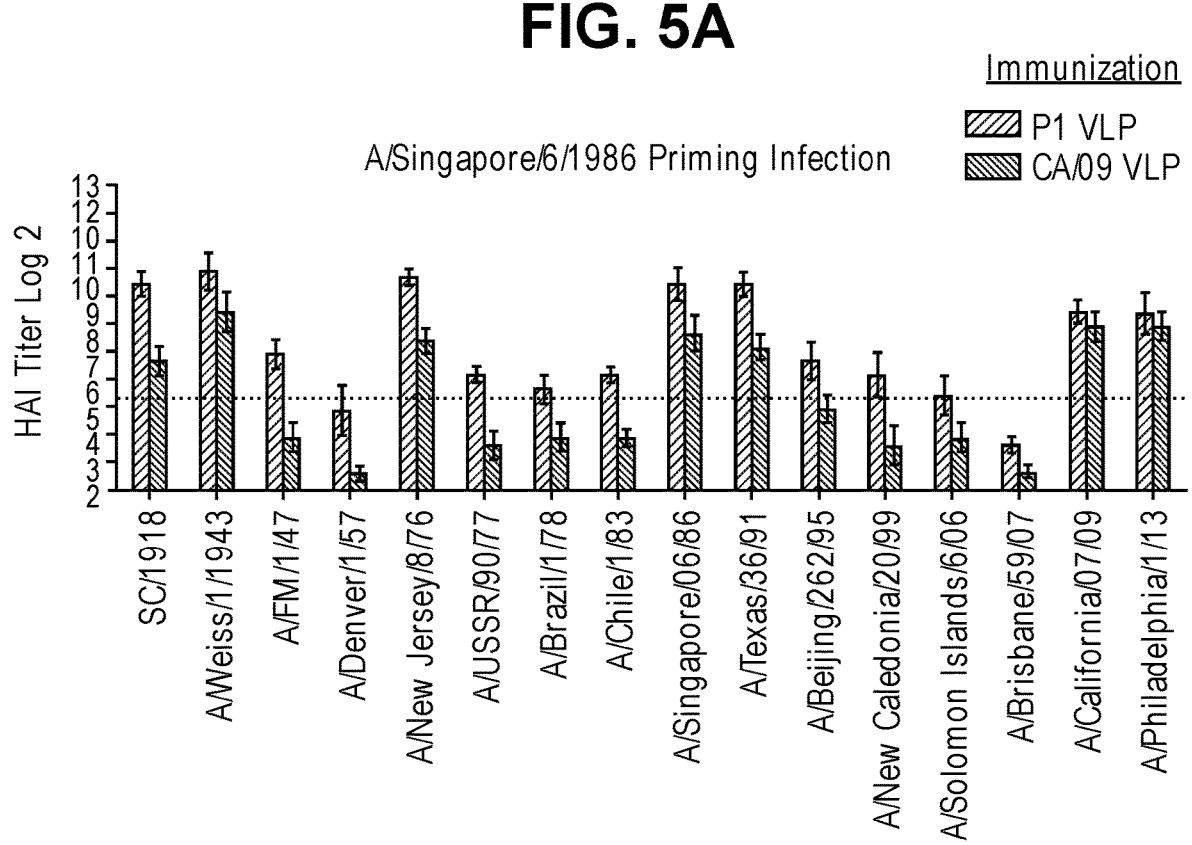
Figure 5C:
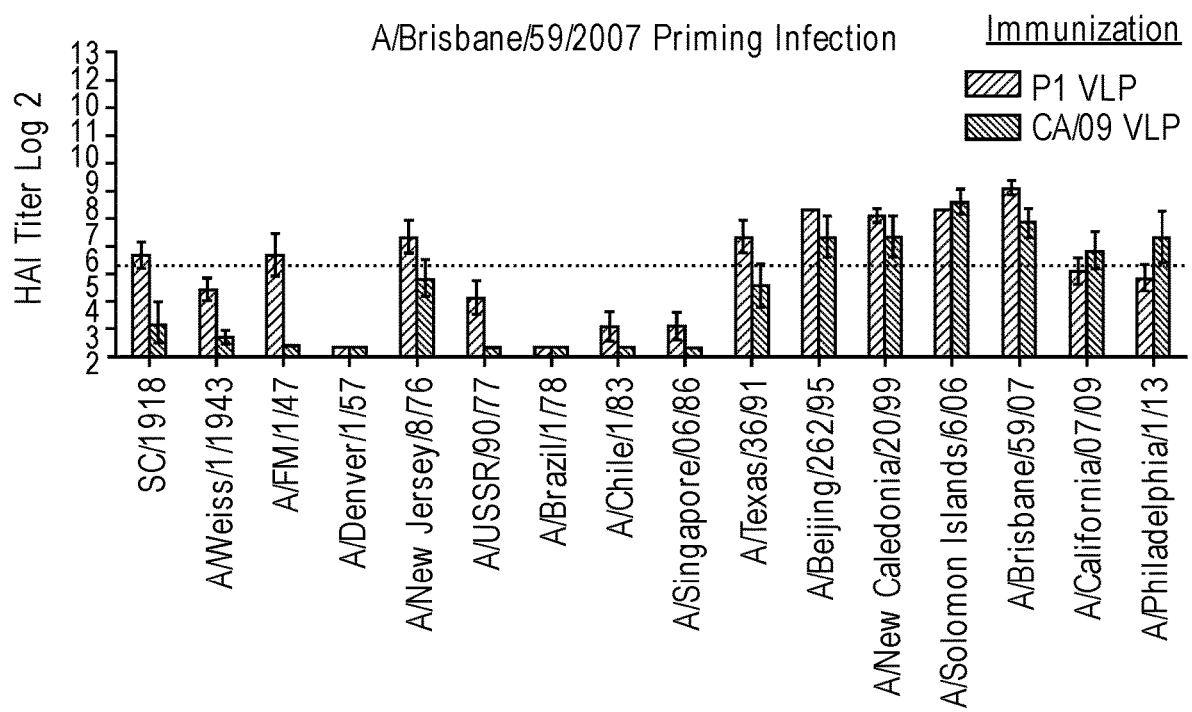
Figure 5D:
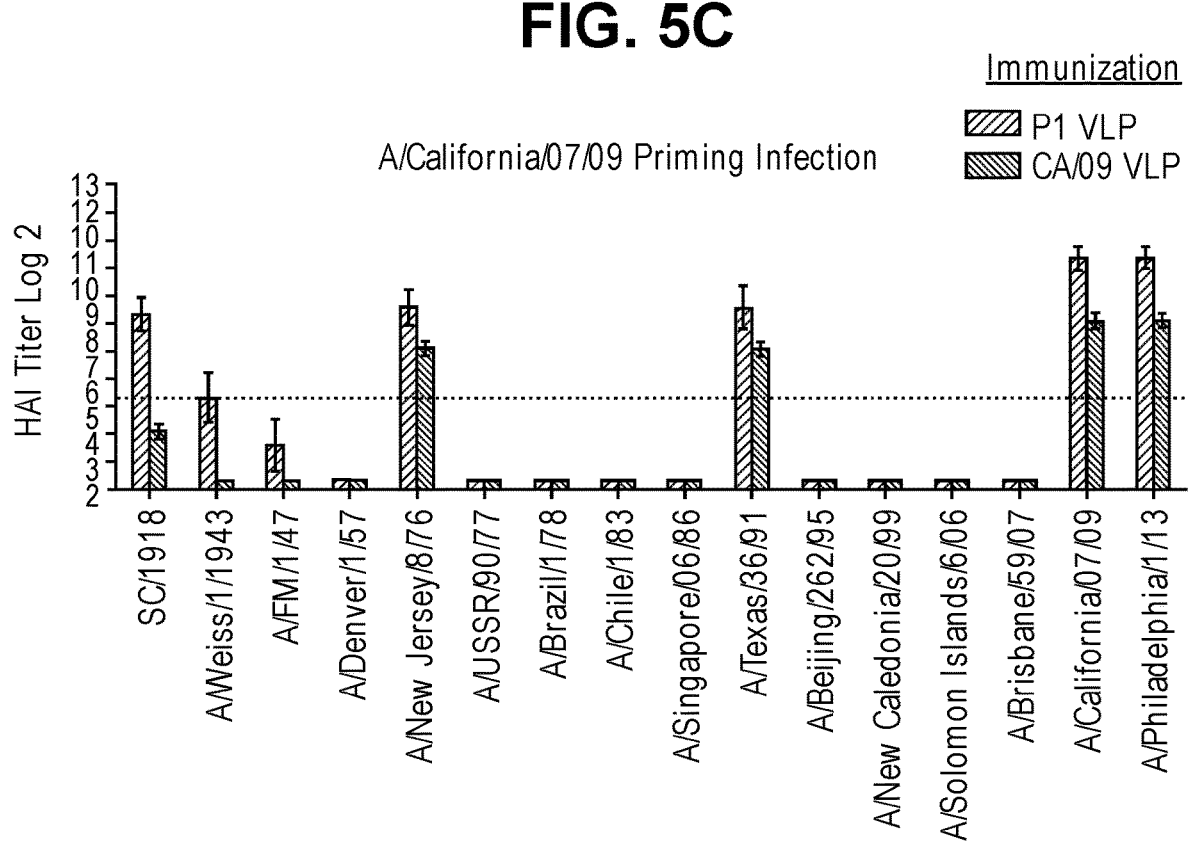
Figure 5E:
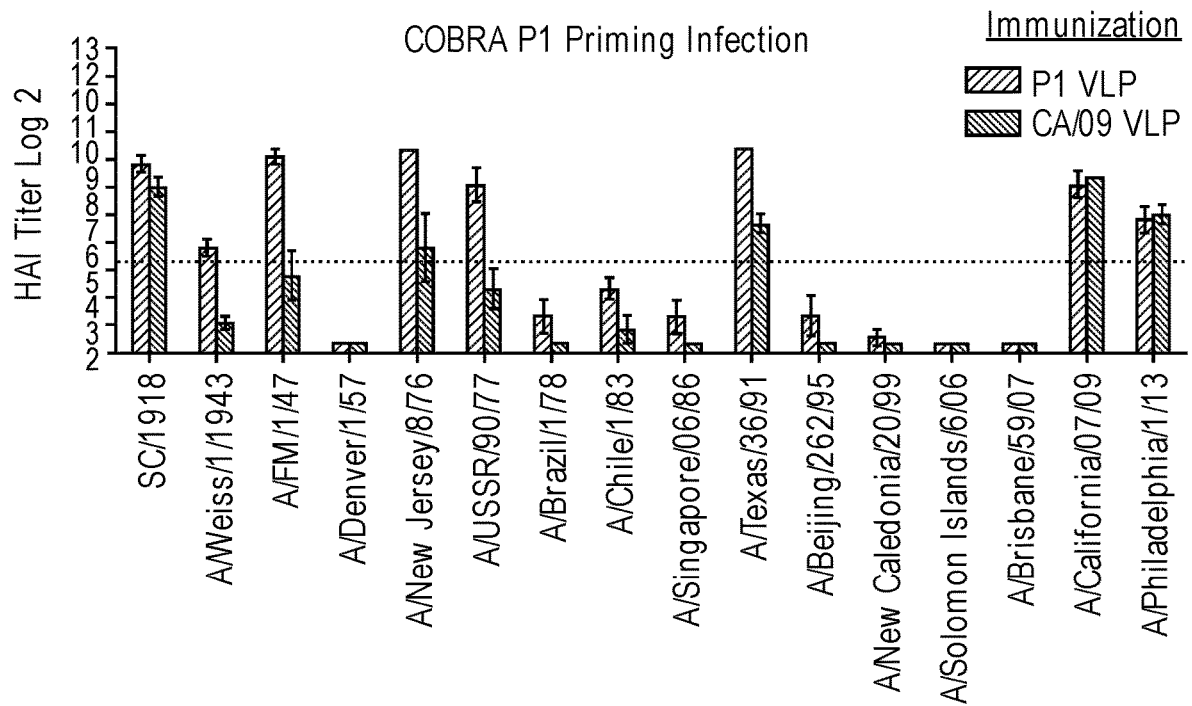
Figure 5F:
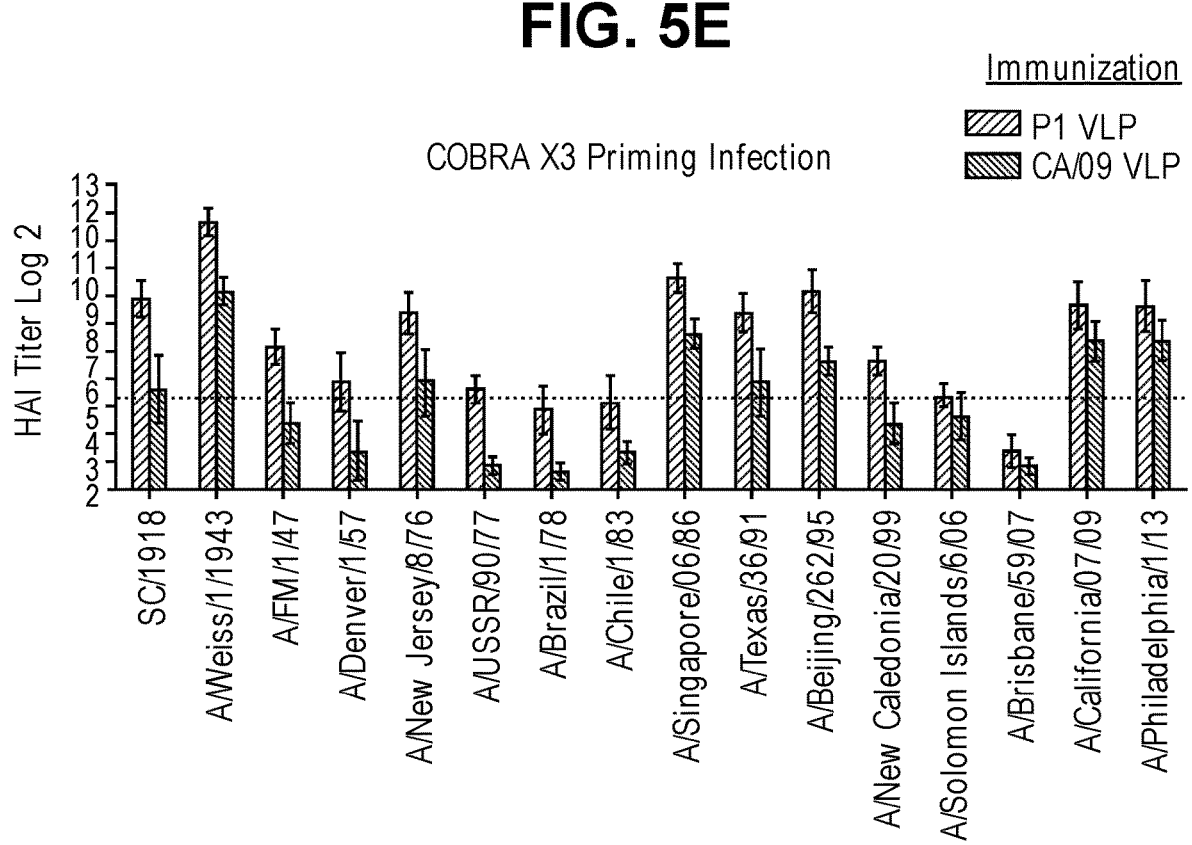

A similar trend was observed for all other priming infections, with COBRA P1 HA driving a seroprotective response against more strains than CA/09 HA in the context of A/Brisbane/59/2007 priming (8/16 for COBRA P1 vs 6/16 for CA/09; FIG. 5C), A/California/07/2009 priming (5 of 16 for COBRA P1 vs 4/16 for CA/09; FIG. 5D), COBRA P1 priming (8/16 for COBRA P1 vs 5/16 for CA/09; FIG. 5E), and COBRA X3 priming (13/16 for COBRA P1 vs 8/16 for CA/09; FIG. 5F). In all instances there was a trend towards COBRA P1 VLPs inducing a higher magnitude response against strains that were also induced by CA/09 VLPs. These data show that COBRA P1 induces broader immunity than that elicited by the current CA/09 standard of care, demonstrating the utility of the H1N1 COBRAs disclosed herein as a broadly reactive antigen for use in influenza vaccines. Further, these results show that heterologous prime/boost regimens can be used to expand the breadth and magnitude of HAI responses to influenza antigens.

EQUIVALENTS

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

We claim:

1. An immunogenic composition comprising a combination of at least two recombinant H1N1 influenza hemagglutinin (HA) polypeptides, wherein the combination comprises a first recombinant, optimized H1N1 influenza HA polypeptide comprising an amino acid sequence at least 98% identical to SEQ ID NO: 1 and a second recombinant, optimized H1N1 influenza HA polypeptide comprising an amino acid sequence selected from the group consisting of: an amino acid sequence at least 99% identical to SEQ ID NO: 2, an amino acid sequence at least 99% identical to SEQ ID NO: 3, and an amino acid sequence at least 96% identical to SEQ ID NO: 4.

2. The immunogenic composition of claim 1, wherein the composition comprises (i) a first recombinant, optimized H1N1 influenza HA polypeptide comprising an amino acid sequence at least 98.5% identical to SEQ ID NO: 1, and (ii) a second recombinant, optimized H1N1 influenza HA polypeptide comprising an amino acid sequence at least 99 identical to SEQ ID NO: 2.

3. The immunogenic composition of claim 1, wherein the composition comprises at least two different recombinant, optimized H1N1 influenza HA polypeptides, wherein the amino acid sequence of the polypeptides comprises no more than two, or no more than one substitution relative to SEQ ID NO: 1 or SEQ ID NO: 2.

4. The immunogenic composition of claim 1, wherein the first and/or second recombinant, optimized H1N1 influenza HA polypeptide lacks the N-terminal methionine residue.

5. The immunogenic composition of claim 1, wherein the composition comprises (i) a first recombinant, optimized H1N1 influenza HA polypeptide comprising an amino acid sequence of SEQ ID NO: 1 or residues 2-566 of SEQ ID NO: 1, and (ii) a second recombinant, optimized H1N1 influenza HA polypeptide comprising an amino acid sequence of SEQ ID NO: 2 or residues 2-565 of SEQ ID NO: 2.

6. The immunogenic composition of claim 1, wherein the composition comprises (i) a first recombinant, optimized H1N1 influenza HA polypeptide comprising an amino acid sequence at least 98.5% identical to SEQ ID NO: 1, and (ii) a second recombinant, optimized H1N1 influenza HA polypeptide comprising an amino acid sequence at least 99% identical to SEQ ID NO: 3.

7. The immunogenic composition of claim 1, wherein the composition comprises at least two different recombinant, optimized H1N1 influenza HA polypeptides, wherein the amino acid sequence of the polypeptides comprises no more than two, or no more than one substitution relative to SEQ ID NO: 1 or SEQ ID NO: 3.

8. The immunogenic composition of claim 1, wherein the composition comprises (i) a first recombinant, optimized H1N1 influenza HA polypeptide comprising an amino acid sequence of SEQ ID NO: 1 or residues 2-566 of SEQ ID NO: 1, and (ii) a second recombinant, optimized H1N1 influenza HA polypeptide comprising an amino acid sequence of SEQ ID NO: 3 or residues 2-566 of SEQ ID NO: 3.

9. The immunogenic composition of claim 1, wherein the composition comprises (i) a first recombinant, optimized H1N1 influenza HA polypeptide comprising an amino acid sequence at least 98.5% identical to SEQ ID NO: 1, and (ii) a second recombinant, optimized H1N1 influenza HA polypeptide comprising an amino acid sequence at least 96% identical to SEQ ID NO: 4.

10. The immunogenic composition of claim 1, wherein the composition comprises at least two different recombinant, optimized H1N1 influenza HA polypeptides, wherein the amino acid sequence of the polypeptides comprises no more than two, or no more than one substitution relative to SEQ ID NO: 1 or SEQ ID NO: 4.

11. The immunogenic composition of claim 1, wherein the composition comprises (i) a first recombinant, optimized H1N1 influenza HA polypeptide comprising an amino acid sequence of SEQ ID NO: 1 or residues 2-566 of SEQ ID NO: 1, and (ii) a second recombinant, optimized H1N1 influenza HA polypeptide comprising an amino acid sequence of SEQ ID NO: 4 or residues 2-566 of SEQ ID NO: 4.

12. The immunogenic composition of claim 1, wherein the composition comprises a combination of recombinant H1N1 influenza HA polypeptides consisting of a first recombinant, optimized H1N1 influenza HA polypeptide comprising an amino acid sequence at least 98.5% identical to residues 2-566 of SEQ ID NO: 1 and a second recombinant, optimized influenza HA polypeptide comprising an amino acid sequence at least 99% identical to residues 2-565 of SEQ ID NO: 2.

13. The immunogenic composition of claim 1, wherein the composition comprises a combination of recombinant H1N1 influenza HA polypeptides consisting of a first recombinant, optimized influenza HA polypeptide comprising an amino acid sequence at least 98.5% identical to residues 2-566 of SEQ ID NO: 1 and a second recombinant, optimized influenza HA polypeptide comprising an amino acid sequence at least 99% identical to amino acids 2-566 of SEQ ID NO: 3.

14. The immunogenic composition of claim 1, wherein the composition comprises a combination of recombinant H1N1 influenza HA polypeptides consisting of a first recombinant, optimized influenza HA polypeptide comprising an amino acid sequence at least 98.5% identical to residues 2-566 of SEQ ID NO: 1 and a second recombinant, optimized influenza HA polypeptide comprising an amino acid sequence at least 96% identical to amino acids 2-566 of SEQ ID NO: 4.

15. The immunogenic composition of claim 1, wherein the composition consists of (i) a first recombinant, optimized H1N1 influenza HA polypeptide comprising an amino acid sequence of SEQ ID NO: 1 or residues 2-566 of SEQ ID NO: 1, and (ii) a second recombinant, optimized H1N1 influenza HA polypeptide comprising an amino acid sequence of SEQ ID NO: 2 or residues 2-565 of SEQ ID NO: 2.

16. The immunogenic composition of claim 1, wherein the composition consists of (i) a first recombinant, optimized H1N1 influenza HA polypeptide comprising an amino acid sequence of SEQ ID NO: 1 or residues 2-566 of SEQ ID NO: 1, and (ii) a second recombinant, optimized H1N1 influenza HA polypeptide comprising an amino acid sequence of SEQ ID NO: 3 or residues 2-566 of SEQ ID NO: 3.

17. The immunogenic composition of claim 1, wherein the composition consists of (i) a first recombinant, optimized H1N1 influenza HA polypeptide comprising an amino acid sequence of SEQ ID NO: 1 or residues 2-566 of SEQ ID NO: 1, and (ii) a second recombinant, optimized H1N1 influenza HA polypeptide comprising an amino acid sequence of SEQ ID NO: 4 or residues 2-566 of SEQ ID NO: 4.

18. An isolated nucleic acid molecule encoding one or more of the recombinant H1N1 influenza HA polypeptides of claim 1.

19. A vector comprising the nucleic acid molecule of claim 18.

20. An isolated cell comprising the vector of claim 19.

21. A recombinant influenza virus comprising one or more of the recombinant H1N1 influenza HA polypeptides of claim 1.

22. An influenza virus-like particle (VLP) comprising one or more of the recombinant H1N1 influenza HA polypeptides of claim 1.

23. An inactivated influenza virus or virion comprising one or more of the recombinant H1N1 influenza HA polypeptides of claim 1.

24. A fusion protein comprising one or more of the recombinant H1N1 influenza HA polypeptides of claim 1.

25. The immunogenic composition of claim 1, wherein the composition further comprises an adjuvant.

26. An immunogenic composition of at least two recombinant H1N1 influenza hemagglutinin (HA) polypeptides, wherein the combination comprises a first recombinant, optimized H1N1 influenza HA polypeptide comprising an amino acid sequence at least 98.5% identical to residues 2-566 of SEQ ID NO: 1 and a second recombinant, optimized H1N1 influenza HA polypeptide comprising an amino acid sequence selected from the group consisting of: an amino acid sequence at least 99% identical to residues 2-565 of SEQ ID NO: 2, an amino acid sequence at least 99% identical to residues 2-566 of SEQ ID NO: 3, and an amino acid sequence at least 96% identical to residues 2-566 of SEQ ID NO: 4.

27. A method of immunizing a subject against H1N1 influenza virus, the method comprising: administering to the subject a priming vaccine comprising a first optimized H1N1 influenza HA polypeptide followed by a boosting vaccine comprising a second optimized H1N1 influenza HA polypeptide, wherein:
the priming vaccine comprises a recombinant, optimized H1N1 influenza HA polypeptide at least 98% identical to SEQ ID NO: 1, and the boosting vaccine comprises a recombinant, optimized H1N1 influenza HA polypeptide at least 99% identical to SEQ ID NO: 2, at least 99% identical to SEQ ID NO: 3 or at least 96% identical to SEQ ID NO: 4, or
the priming vaccine comprises a recombinant, optimized H1N1 influenza HA polypeptide at least 99% identical to SEQ ID NO: 2, and the boosting vaccine comprises a recombinant, optimized H1N1 influenza HA polypeptide at least 98% identical to SEQ ID NO: 1, at least 99% identical to SEQ ID NO: 3 or at least 96% identical to SEQ ID NO: 4, or
the priming vaccine comprises a recombinant, optimized H1N1 influenza HA polypeptide at least 99% identical to SEQ ID NO: 3, and the boosting vaccine comprises a recombinant, optimized H1N1 influenza HA polypeptide at least 98% identical to SEQ ID NO: 1, at least 99% identical to SEQ ID NO: 2 or at least 96% identical to SEQ ID NO: 4.

28. The method of claim 27, wherein the subject is human.

* * * * *